US012168097B2

(12) United States Patent
Miller et al.

(10) Patent No.: US 12,168,097 B2
(45) Date of Patent: Dec. 17, 2024

(54) BREATHING ASSISTANCE APPARATUS

(71) Applicant: Fisher & Paykel Healthcare Limited, Auckland (NZ)

(72) Inventors: Rachel Adeline Miller, Auckland (NZ); Andrew Paul Maxwell Salmon, Auckland (NZ); Andre van Schalkwyk, Auckland (NZ); Ella Marie Meisel, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 227 days.

(21) Appl. No.: 17/848,765

(22) Filed: Jun. 24, 2022

(65) Prior Publication Data
US 2023/0144814 A1 May 11, 2023

Related U.S. Application Data

(63) Continuation of application No. 15/851,570, filed on Dec. 21, 2017, now Pat. No. 11,400,247.
(Continued)

(51) Int. Cl.
*A61M 16/10* (2006.01)
*A61M 16/00* (2006.01)
(Continued)

(52) U.S. Cl.
CPC .... *A61M 16/0672* (2014.02); *A61M 16/0069* (2014.02); *A61M 16/021* (2017.08);
(Continued)

(58) Field of Classification Search
CPC ..... A61M 16/10; A61M 16/109; A61M 16/16
See application file for complete search history.

(56) References Cited

U.S. PATENT DOCUMENTS

| | | |
|---|---|---|
| 863,189 A | 8/1907 | Lauritzen |
| 2,115,482 A | 4/1938 | Crewe |

(Continued)

FOREIGN PATENT DOCUMENTS

| | | |
|---|---|---|
| AU | 2010257238 | 1/2011 |
| DE | 10323754 | 12/2004 |

(Continued)

OTHER PUBLICATIONS

MyAIRVO 2 Technical Manual, Fisher & Paykel Healthcare Limited, Aug. 2016, in 32 pages.

*Primary Examiner* — Margaret M Luarca
(74) *Attorney, Agent, or Firm* — VIA LLP

(57) ABSTRACT

An apparatus for delivering a flow of gas has a housing, a cover, and a magnetic coupling system arranged to magnetically couple the cover—to the housing. Each of the housing and cover having complementary locating features, the locating features being adapted to locate and align the cover and the apparatus relative to each other to allow for the magnetic coupling. The apparatus also has a handle movably connected to the housing and is movable from a first position to a second position. The housing and the handle comprise complementary interlock features arranged to engage with each other when upward force is applied to the handle in the second position, and the interlock features are disengaged from each other when the handle is in the second position but upward force is not applied to the handle.

18 Claims, 31 Drawing Sheets

Related U.S. Application Data

(60) Provisional application No. 62/596,454, filed on Dec. 8, 2017, provisional application No. 62/438,206, filed on Dec. 22, 2016, provisional application No. 62/438,099, filed on Dec. 22, 2016.

(51) Int. Cl.
*A61M 16/06* (2006.01)
*A61M 16/16* (2006.01)
*A61M 16/08* (2006.01)

(52) U.S. Cl.
CPC ........ *A61M 16/022* (2017.08); *A61M 16/109* (2014.02); *A61M 16/1095* (2014.02); *A61M 16/16* (2013.01); *A61M 2016/0027* (2013.01); *A61M 2016/0039* (2013.01); *A61M 16/0683* (2013.01); *A61M 16/0875* (2013.01); *A61M 16/161* (2014.02); *A61M 2202/0208* (2013.01); *A61M 2205/3368* (2013.01); *A61M 2205/502* (2013.01)

(56) References Cited

U.S. PATENT DOCUMENTS

| | | |
|---|---|---|
| 3,809,086 A | 5/1974 | Deuschle |
| 4,098,853 A | 7/1978 | Brown et al. |
| 4,722,334 A | 2/1988 | Blackmer et al. |
| 4,852,032 A | 7/1989 | Matsuda et al. |
| 4,901,261 A | 2/1990 | Fuhs |
| 5,007,420 A | 4/1991 | Bird |
| 5,061,405 A | 10/1991 | Stanek et al. |
| 5,212,021 A | 5/1993 | Smith et al. |
| 5,573,713 A | 11/1996 | Tomasiak et al. |
| 5,640,951 A | 6/1997 | Huddart et al. |
| 5,741,305 A | 4/1998 | Vincent et al. |
| 5,943,473 A | 8/1999 | Levine |
| 6,050,260 A | 4/2000 | Daniell et al. |
| 6,158,430 A | 12/2000 | Pfeiffer et al. |
| 6,349,724 B1 | 2/2002 | Burton et al. |
| 6,397,841 B1 | 6/2002 | Kenyon et al. |
| 6,398,197 B1 | 6/2002 | Dickinson et al. |
| 6,520,021 B1 | 2/2003 | Wixey et al. |
| 6,648,664 B1 | 11/2003 | McHugh et al. |
| 6,661,649 B2 | 12/2003 | Tanaka et al. |
| 6,935,337 B2 | 8/2005 | Virr et al. |
| 7,111,624 B2 | 9/2006 | Thudor et al. |
| 7,137,388 B2 | 11/2006 | Virr et al. |
| 7,144,473 B2 | 12/2006 | Baecke |
| 7,188,621 B2 | 3/2007 | DeVries et al. |
| 7,320,321 B2 | 1/2008 | Pranger et al. |
| 7,413,173 B2 | 8/2008 | DiMatteo et al. |
| 7,431,753 B2 | 10/2008 | Yoshida et al. |
| 7,516,743 B2 | 4/2009 | Hoffman |
| 7,614,398 B2 | 11/2009 | Virr et al. |
| 7,677,246 B2 | 3/2010 | Kepler et al. |
| 7,721,736 B2 | 5/2010 | Urias et al. |
| 7,736,132 B2 | 6/2010 | Bliss et al. |
| 7,942,380 B2 | 5/2011 | Bertinetti et al. |
| 8,006,691 B2 | 8/2011 | Kenyon et al. |
| 8,011,362 B2 | 9/2011 | Adams |
| 8,020,551 B2 | 9/2011 | Virr et al. |
| 8,020,557 B2 | 9/2011 | Bordewick et al. |
| 8,028,693 B2 | 10/2011 | Trevor-Wilson et al. |
| 8,042,535 B2 | 10/2011 | Kenyon et al. |
| 8,151,792 B2 | 4/2012 | Ishizaki et al. |
| 8,267,084 B2 | 9/2012 | Kwok |
| 8,297,279 B2 | 10/2012 | DeVries et al. |
| 8,316,848 B2 | 11/2012 | Kwok et al. |
| 8,337,145 B2 | 12/2012 | Frater et al. |
| 8,365,726 B2 | 2/2013 | Snow et al. |
| 8,375,945 B2 | 2/2013 | Kepler et al. |
| 8,453,640 B2 | 6/2013 | Martin et al. |
| RE44,453 E | 8/2013 | Virr et al. |
| 8,517,017 B2 | 8/2013 | Bowditch et al. |
| 8,544,465 B2 | 10/2013 | Smith et al. |
| 8,567,397 B2 | 10/2013 | Bowman et al. |
| 8,631,789 B2 | 1/2014 | Virr et al. |
| 8,677,997 B2 | 3/2014 | O'Connor et al. |
| 8,702,379 B2 | 4/2014 | Frater et al. |
| 8,733,349 B2 | 5/2014 | Bath et al. |
| 8,770,198 B2 | 7/2014 | Yee et al. |
| 8,789,525 B2 | 7/2014 | Snow et al. |
| 8,800,560 B2 | 8/2014 | Alfieri et al. |
| 8,894,751 B2 | 11/2014 | Galbraith et al. |
| 8,925,544 B2 | 1/2015 | Flickinger |
| 9,010,324 B2 | 4/2015 | Martin et al. |
| 9,038,629 B2 | 5/2015 | Smith et al. |
| 9,038,631 B2 | 5/2015 | Bath et al. |
| 9,038,632 B2 | 5/2015 | Crumblin et al. |
| 9,044,561 B2 | 6/2015 | Adams |
| 9,044,564 B2 | 6/2015 | Dravitzki et al. |
| 9,072,543 B2 | 7/2015 | Miller et al. |
| 9,072,860 B2 | 7/2015 | Lithgow et al. |
| 9,162,035 B2 | 10/2015 | Kwok |
| 9,182,062 B2 | 11/2015 | Kwok et al. |
| 9,199,055 B2 | 12/2015 | Galbraith et al. |
| 9,227,035 B2 | 1/2016 | Crumblin et al. |
| 9,314,579 B2 | 4/2016 | McDaniel et al. |
| 9,358,359 B2 | 6/2016 | Lithgow et al. |
| RE46,079 E | 7/2016 | Virr et al. |
| 9,393,377 B2 | 7/2016 | Smith et al. |
| 9,402,970 B2 | 8/2016 | Virr et al. |
| 9,539,409 B2 | 1/2017 | Crumblin et al. |
| 9,545,493 B2 | 1/2017 | Mayer et al. |
| 9,555,211 B2 | 1/2017 | Mayer et al. |
| 9,610,420 B2 | 4/2017 | Lithgow et al. |
| 9,649,459 B2 | 5/2017 | Taylor et al. |
| 9,656,034 B2 | 5/2017 | Kepler et al. |
| 9,717,873 B2 | 8/2017 | Dimatteo et al. |
| 9,737,682 B2 | 8/2017 | Maurer et al. |
| RE46,543 E | 9/2017 | Trevor-Wilson et al. |
| RE46,571 E | 10/2017 | Virr et al. |
| 9,782,552 B1 | 10/2017 | Adams |
| 9,802,022 B2 | 10/2017 | Smith et al. |
| 9,839,757 B2 | 12/2017 | Galbraith |
| 9,861,778 B2 | 1/2018 | Bath et al. |
| 9,872,703 B2 | 1/2018 | Miller et al. |
| 9,974,918 B2 | 5/2018 | Armstrong et al. |
| 10,058,666 B2 | 8/2018 | Kwok et al. |
| 10,112,025 B2 | 10/2018 | Bowditch et al. |
| 10,195,378 B2 | 2/2019 | Truschel et al. |
| 10,265,490 B2 | 4/2019 | Barlow et al. |
| 10,682,331 B2 | 6/2020 | Flickinger |
| 10,898,664 B2 | 1/2021 | Taylor et al. |
| 2003/0066526 A1 | 4/2003 | Thudor et al. |
| 2004/0035424 A1 | 2/2004 | Wiesmann et al. |
| 2006/0237005 A1 | 10/2006 | Virr et al. |
| 2006/0287013 A1 | 12/2006 | Kim |
| 2007/0045152 A1 | 3/2007 | Kwok et al. |
| 2007/0079826 A1 | 4/2007 | Kramer et al. |
| 2007/0277827 A1 | 12/2007 | Bordewick et al. |
| 2008/0000474 A1 | 1/2008 | Jochle et al. |
| 2008/0099017 A1 | 5/2008 | Bordewick et al. |
| 2008/0302361 A1 | 12/2008 | Snow |
| 2009/0007911 A1 | 1/2009 | Clearly et al. |
| 2009/0071478 A1 | 3/2009 | Kalfon |
| 2010/0116272 A1 | 5/2010 | Row et al. |
| 2010/0147301 A1 | 6/2010 | Kwok |
| 2010/0192094 A1 | 7/2010 | Jeha et al. |
| 2010/0218764 A1 | 9/2010 | Kwok et al. |
| 2011/0203587 A1 | 8/2011 | Bertinetti et al. |
| 2011/0247620 A1 | 10/2011 | Armstrong et al. |
| 2011/0283999 A2 | 11/2011 | Smith et al. |
| 2011/0307194 A1 | 12/2011 | Wickham et al. |
| 2012/0266880 A1 | 10/2012 | Young |
| 2012/0319313 A1 | 12/2012 | Davis |
| 2012/0325227 A1* | 12/2012 | Robinson ............ A61M 16/108 131/328 |
| 2013/0037027 A1 | 2/2013 | Schuller |
| 2013/0118492 A1 | 5/2013 | Snow et al. |
| 2013/0174843 A1 | 7/2013 | Smith et al. |
| 2013/0206140 A1 | 8/2013 | Kepler et al. |
| 2013/0239961 A1 | 9/2013 | Ross, Jr. et al. |

(56) References Cited

U.S. PATENT DOCUMENTS

| | | |
|---|---|---|
| 2013/0263854 A1 | 10/2013 | Taylor et al. |
| 2013/0269696 A1 | 10/2013 | Mayer et al. |
| 2013/0280055 A1 | 10/2013 | Daly et al. |
| 2014/0202460 A1 | 7/2014 | Bath et al. |
| 2014/0230244 A1 | 8/2014 | Frater et al. |
| 2014/0264975 A1 | 9/2014 | Bath et al. |
| 2014/0290655 A1 | 10/2014 | Snow et al. |
| 2015/0059745 A1 | 3/2015 | Barker |
| 2015/0079098 A1 | 3/2015 | Felder |
| 2015/0120067 A1 | 4/2015 | Wing et al. |
| 2015/0136127 A1 | 5/2015 | DiMatteo et al. |
| 2015/0136129 A1 | 5/2015 | Mahadevan et al. |
| 2015/0190605 A1 | 7/2015 | Martin et al. |
| 2015/0224494 A1 | 8/2015 | Gray et al. |
| 2015/0231358 A1 | 8/2015 | Smith et al. |
| 2015/0283339 A1 | 10/2015 | Mahadevan et al. |
| 2015/0335838 A1 | 11/2015 | Truschel et al. |
| 2015/0373526 A1 | 12/2015 | Bukurak et al. |
| 2015/0374950 A1 | 12/2015 | DeVries et al. |
| 2016/0008560 A1 | 1/2016 | Kwok |
| 2016/0022954 A1 | 1/2016 | Bath et al. |
| 2016/0199612 A1 | 7/2016 | Foote et al. |
| 2016/0022935 A1 | 10/2016 | Yutaka et al. |
| 2016/0303343 A1 | 10/2016 | Virr et al. |
| 2016/0310691 A1 | 10/2016 | Bath et al. |
| 2016/0317775 A1 | 10/2016 | Smith et al. |
| 2016/0317392 A1 | 11/2016 | Harris et al. |
| 2017/0087327 A1 | 3/2017 | Crumblin et al. |
| 2017/0136198 A1 | 5/2017 | Delangre et al. |
| 2017/0182270 A1 | 6/2017 | Kenyon et al. |
| 2017/0232221 A1 | 8/2017 | Kepler et al. |
| 2017/0326329 A1 | 11/2017 | Maurer et al. |
| 2018/0008795 A1 | 1/2018 | Smith et al. |
| 2018/0132894 A1 | 5/2018 | Miller et al. |
| 2018/0142690 A1 | 5/2018 | Row et al. |
| 2019/0038865 A1 | 2/2019 | Smith et al. |

FOREIGN PATENT DOCUMENTS

| | | |
|---|---|---|
| DE | 102005000819 | 7/2006 |
| DE | 10017193 | 5/2007 |
| DE | 102007026565 | 12/2007 |
| DE | 102012100939 | 8/2013 |
| EP | 989875 | 4/2000 |
| EP | 1359963 | 11/2003 |
| EP | 1648544 | 4/2006 |
| EP | 1669098 | 6/2006 |
| EP | 1824542 | 8/2007 |
| EP | 1855749 | 11/2007 |
| EP | 1924311 | 5/2008 |
| EP | 1933910 | 6/2008 |
| EP | 1968673 | 9/2008 |
| EP | 1858233 | 4/2010 |
| EP | 2345449 | 7/2011 |
| EP | 2098260 | 4/2012 |
| EP | 2475168 | 12/2012 |
| EP | 2572747 | 3/2013 |
| EP | 2854916 | 4/2015 |
| EP | 2910271 | 8/2015 |
| EP | 2392375 | 1/2016 |
| EP | 2968829 | 1/2016 |
| EP | 2992921 | 3/2016 |
| EP | 3013402 | 5/2016 |
| EP | 3082920 | 10/2016 |
| EP | 2465565 | 11/2016 |
| EP | 2335761 | 4/2017 |
| EP | 3148419 | 4/2017 |
| EP | 3149696 | 4/2017 |
| EP | 3254722 | 12/2017 |
| EP | 2337604 | 1/2018 |
| EP | 3148418 | 1/2018 |
| EP | 3311869 | 4/2018 |
| EP | 3311871 | 4/2018 |
| EP | 3153762 | 4/2019 |
| FR | 2901998 | 12/2007 |
| JP | 3060967 | 9/1999 |
| WO | WO 1998/033433 | 8/1998 |
| WO | WO 1998/057691 | 12/1998 |
| WO | WO 1999/047197 | 9/1999 |
| WO | WO 2000/012197 | 3/2000 |
| WO | WO 2000/049722 | 8/2000 |
| WO | WO 2003/064009 | 8/2003 |
| WO | WO 2004/084981 | 10/2004 |
| WO | WO 2004/112873 | 12/2004 |
| WO | WO 2005/013879 | 2/2005 |
| WO | WO 2006/092001 | 9/2006 |
| WO | WO 2007/019624 | 2/2007 |
| WO | WO 2007/019625 | 2/2007 |
| WO | WO 2007/019627 | 2/2007 |
| WO | WO 2007/076570 | 7/2007 |
| WO | WO 2007/123899 | 11/2007 |
| WO | WO 2007/149446 | 12/2007 |
| WO | WO 2008/074058 | 6/2008 |
| WO | WO 2010/031126 | 3/2010 |
| WO | WO 2010/044039 | 4/2010 |
| WO | WO 2010/054323 | 5/2010 |
| WO | WO 2010/080709 | 7/2010 |
| WO | WO 2012/094230 | 7/2012 |
| WO | WO 2012/160477 | 11/2012 |
| WO | WO 2014/138804 | 9/2014 |
| WO | WO 2014/205513 | 12/2014 |
| WO | WO 2016/041718 | 3/2016 |
| WO | WO 2016/097928 | 6/2016 |
| WO | WO 2016/207838 | 12/2016 |
| WO | WO 2017/006189 | 1/2017 |
| WO | WO 2017/165749 | 9/2017 |

\* cited by examiner

BREATHING ASSISTANCE APPARATUS

TECHNICAL FIELD

The present disclosure relates to a flow therapy apparatus for delivering gas to patients.

BACKGROUND ART

Breathing assistance apparatuses are used in various environments such as hospital, medical facility, residential care, or home environments to deliver a flow of gas to users or patients.

SUMMARY

The applicant has identified potential difficulties in inserting and/or retaining and/or removing a cover of a breathing assistance apparatus, particularly for users with limited mobility.

The applicant has also identified potential difficulties in inserting and/or retaining and/or removing a liquid chamber in and/or from a liquid chamber bay of a breathing assistance apparatus, particularly for users with limited mobility. Full or correct insertion and/or retention may be required to ensure that a satisfactory seal is obtained and maintained between the liquid chamber and other component(s) that form part of the gasflow path.

The applicant has further identified potential strength limitations in handles that are movably connected to breathing assistance apparatus housings.

It would be desirable to provide a cover for an apparatus for delivering a flow of gas that has one or more features that assist with cleaning the cover and/or apparatus.

It would be desirable to provide an apparatus for delivering a flow of gas that has one or more features that assist with inserting and/or retaining and/or removing a cover from a breathing assistance apparatus.

It would be desirable to provide an apparatus for delivering a flow of gas that has one or more features that assist with inserting and/or retaining and/or removing a liquid chamber in and/or from a liquid chamber bay.

It would be desirable to provide an apparatus for delivering a flow of gas that has a movable handle that can better accommodate loadings that are encountered when the handle is used to carry the apparatus.

It is an object of one or more of the disclosed embodiments to provide an apparatus for delivering a flow of gas that has one or more features that assist with the use, functioning, or configuration of the apparatus or improves the safety of the apparatus, or that will at least provide the public or a medical professional with a useful choice.

Thus, in accordance with certain features, aspects and advantages of at least one of the embodiments disclosed herein, an apparatus for delivering a flow of gas, comprises: a housing and a cover, a magnetic coupling system arranged to magnetically couple the cover to the housing, each of the housing and cover having complementary locating features, the locating features being adapted to locate and align the cover and the housing relative to each other to allow for said magnetic coupling.

In accordance with certain features, aspects and advantages of at least one of the embodiments disclosed herein, there is provided a cover for an apparatus for delivering a flow of gas, the cover comprising locating features for engaging with complementary locating features of the apparatus the locating features being adapted to locate and align the cover and the apparatus relative to each other to allow for magnetic coupling between the cover and the apparatus.

In some embodiments the magnetic coupling system comprises at least one magnet associated with one of the housing or cover and at least one ferrous part associated with the other of the housing or cover.

In some embodiments the magnetic coupling system comprises multiple magnets associated with one of the housing or cover.

In some embodiments the magnetic coupling system comprises multiple ferrous parts associated with the other of the housing or cover.

In some embodiments the magnetic coupling system comprises at least one magnet associated with the housing and at least one other magnet associated with the cover.

In some embodiments the magnetic coupling system comprises multiple magnets associated with the housing and multiple magnets associated with the cover.

In some embodiments the at least one magnet is attached by interference fit and/or adhesive.

In some embodiments the cover or apparatus has at least one upstand to hold the at least one magnet.

In some embodiments the apparatus comprises multiple magnets associated with at least one of the cover and the housing, and wherein at least one magnet associated with the cover and at least one magnet associated with the housing are arranged such that they attract when the cover is coupled to the housing in a predetermined orientation of the cover relative to the housing and repel when the cover is offered to the housing in at least one orientation other than said predetermined orientation.

In some embodiments the at least one magnet is embedded in the cover or housing.

In some embodiments the at least one magnet is covered by a surface of the cover or housing.

In some embodiments the locating features of the housing and the cover are interlocking features adapted to form an interlock.

In some embodiments the locating feature of one of the cover or housing comprises at least one projection and the locating feature of the other of the cover or housing comprises at least one recess, the projection and recess forming the interlock.

In some embodiments the at least one projection comprises angled rear and front faces and the at least one recess comprises complementary angled rear and front faces.

In some embodiments the rear face of the projection is of a shorter length than the length of the front face of the projection.

In some embodiments the front face of the projection is of a shorter length than the length of the rear face of the projection.

In some embodiments the locating features are adapted to prevent relative movement between the cover and the housing.

In some embodiments the locating features comprise side walls, and optionally back walls, of the cover.

In some embodiments the locating features comprise the lower surface of the side walls.

In some embodiments, the locating features comprise the lower surface of the side walls.

In some embodiments the interlocking features are adapted to prevent relative movement between the cover and the housing, optionally the interlocking features prevent relative movement between the cover and the housing in an axis substantially parallel with the side wall of the cover.

In some embodiments the interlocking features prevent relative movement between the cover and the housing in an axis substantially parallel to a direction in which the removable elbow is removed.

In some embodiments the cover has a back wall. In some embodiments the cover has a front wall. The back wall and/or front wall may be recessed from an edge of the cover.

In some embodiments the cover covers, retains, assists with retention and/or positions a component of the apparatus.

In some embodiments the component is a removable component.

In some embodiments the component is part of a flow path, for example, a removable elbow.

In some embodiments the component has a pneumatic and/or an electrical connection.

In some embodiments the cover has an aperture to allow for passage of component.

In some embodiments the cover has a lead-in feature to engage part of the component upon initial engagement, to ensure correct alignment between the cover, the breathing apparatus, and the component.

In some embodiments the lead-in feature engages with one or more of the pneumatic or electrical connection features of the removable elbow.

In some embodiments the locating features associated with the housing and the cover allow the cover and housing to be assembled together in a predetermined orientation of the cover relative to the housing and prevent the cover and housing being assembled together when the cover is offered to the housing in at least one orientation other than said predetermined orientation.

In some embodiments the side walls of the cover are asymmetrical about a transverse axis.

In some embodiments the cover comprises an aperture extending through the top of the cover.

In accordance with certain features, aspects and advantages of at least one of the embodiments disclosed herein, there is provided an apparatus for delivering a flow of gas, comprising: a housing and a cover, a magnetic coupling system arranged to magnetically couple the cover to the housing.

In some embodiments the magnetic coupling system comprises at least one magnet, optionally multiple magnets, associated with one of the housing or cover and at least one ferrous part, optionally multiple ferrous parts, associated with the other of the housing or cover.

In some embodiments the magnetic coupling system comprises at least one magnet, optionally multiple magnets, associated with the housing and at least one other magnet, optionally multiple magnets, associated with the cover.

In some embodiments the at least one magnet is attached by interference fit and/or adhesive.

In some embodiments the cover or apparatus has at least one upstand to hold the at least one magnet.

In some embodiments the apparatus comprises multiple magnets associated with at least one of the cover and the housing, and wherein at least one magnet associated with cover and at least one magnet associated with the housing are arranged such that they attract when the cover is coupled to the housing in a predetermined orientation of the cover relative to the housing and repel when the cover is offered to the housing in at least one orientation other than said predetermined orientation.

In some embodiments the at least one magnet is embedded in the cover or housing and optionally covered by a surface of the cover or housing.

In some embodiments the cover covers, retains, assists with retention and/or positions a component, optionally a removable component, of the apparatus.

In some embodiments the component is part of a flow path.

In some embodiments the cover has an aperture to allow for passage of the component.

In some embodiments the cover has a lead-in feature to engage part of the component upon initial engagement, to ensure correct alignment between the cover, the breathing apparatus, and the component.

In some embodiments the lead-in feature engages with one or more of the pneumatic or electrical connection features of the removable elbow.

In accordance with certain features, aspects and advantages of at least one of the embodiments disclosed herein, there is provided an apparatus for delivering a flow of gas, comprising: a housing and a cover, each of the housing and cover having complementary locating features, the locating features being adapted to locate and align the cover and the housing relative to each other.

In some embodiments the locating features of the housing and the cover are interlocking features adapted to form an interlock.

In some embodiments the locating feature of one of the cover or housing comprises at least one projection and the locating feature of the other of the cover or housing comprises at least one recess, the projection and recess forming the interlock.

In some embodiments the at least one projection comprises angled rear and front faces and the at least one recess comprises complementary angled rear and front faces.

In some embodiments the rear face of the projection is of a shorter length than the length of the front face of the projection or the front face of the projection is of a shorter length than the length of the rear face of the projection.

In some embodiments the locating features comprise side walls, and optionally back walls, of the cover.

In some embodiments the interlocking features are adapted to prevent relative movement between the cover and the housing, optionally the interlocking features prevent relative movement between the cover and the housing in an axis substantially parallel with the side wall of the cover.

In some embodiments the interlocking features prevent relative movement between the cover and the housing in an axis substantially parallel to a direction in which the elbow is removed.

In some embodiments the cover covers, retains, assists with retention and/or positions a component, optionally a removable component, of the apparatus.

In some embodiments the component is part of a flow path.

In some embodiments the cover has an aperture to allow for passage of the component.

In some embodiments the cover has a lead-in feature to engage part of the component upon initial engagement, to ensure correct alignment between the cover, the breathing apparatus, and the component.

In some embodiments the lead-in feature engages with one or more of the pneumatic or electrical connection features of the removable elbow.

In some embodiments the locating features associated with the housing and the cover allow the cover and housing to be assembled together in a predetermined orientation of the cover relative to the housing and prevent the cover and housing being assembled together when the cover is offered to the housing in at least one orientation other than said predetermined orientation.

In some embodiments the side walls of the cover are asymmetrical about a transverse axis.

In some embodiments the cover comprises an aperture extending through the top of the cover.

In accordance with certain features, aspects and advantages of at least one of the embodiments disclosed herein, there is provided an apparatus for delivering a flow of gas, comprising: a housing, a component of the apparatus, and a cover that assists with retaining of the component, a component coupling that substantially inhibits the component from moving relative to the housing in a first direction, and a cover coupling that substantially inhibits the cover from moving relative to the housing in a second direction.

In some embodiments the cover coupling is or comprises a magnetic coupling.

In some embodiments the cover coupling is or comprises each of the housing and cover having complementary locating features.

In some embodiments the locating features of the housing and the cover are interlocking features adapted to form an interlock.

In some embodiments the first and second direction are substantially perpendicular.

In some embodiments the second direction is substantially horizontal.

In some embodiments the first direction is substantially vertical.

In accordance with certain features, aspects and advantages of at least one of the embodiments disclosed herein, an apparatus for delivering a flow of gas is disclosed, the apparatus comprising: a housing and a handle, wherein the handle is movably connected to the housing and is movable from a first position to a second position, wherein the housing and the handle comprise complementary interlock features, and wherein the complementary interlock features are arranged such that the interlock features engage with each other when the handle is in the second position and upward force is applied to the handle relative to the housing, and such that the interlock features are disengaged from each other when the handle is in the second position but upward force is not applied to the handle relative to the housing.

In some configurations, the first position is a lowered position and the second position is a raised position. In alternative configurations, the first and/or second position are different position(s). For example, one or both of the first and second positions could be an intermediate position between the lowered position and the raised position.

In some configurations, the interlock features are disengaged from each other when the handle is in an intermediate position between the lowered position and the raised position. In some configurations, the interlock features are disengaged from each other when the handle is in any of a plurality of intermediate positions between the lowered position and the raised position.

In some configurations, the interlock features are engaged with each other when the handle is in an intermediate position between the lowered position and the raised position.

In some configurations, the interlock features comprise a projection on one of the handle and the housing, and a complementary recess on the other of the handle and the housing. In some configurations, at least one of the projection and the recess comprise an angled face to assist with engagement and/or disengagement of the projection and the recess. In some configurations, the angled face(s) comprise forward face(s) of the projection and/or the recess.

In some configurations, the interlock features comprise a plurality of projections on one of the handle and the housing, and a plurality of complementary recesses on the other of the handle and the housing.

In some configurations, the handle comprises an additional interlock feature that is arranged to engage with the interlock feature of the housing when the handle is in the first position. In some configurations, the additional interlock feature has the same form as one of the interlock features on the handle.

In some configurations, the apparatus comprises a heater and a liquid chamber bay for receipt of a liquid chamber. In some configurations, the handle encloses a portion of the liquid chamber bay when the handle is in the first position.

In some configurations, liquid tube(s) can be fed through a space between the handle and the housing when the handle is in the second position.

In some configurations, the handle is pivotally connected to the housing. In some configurations, only one side of the handle is pivotally connected to the housing. In some alternative configurations, two sides of the handle are pivotally connected to the housing.

In some configurations, the handle is pivotally and translationally connected to the housing. In some configurations, only one side of the handle is pivotally and translationally connected to the housing. In some alternative configurations, two sides of the handle are pivotally and translationally connected to the housing.

In some configurations, the apparatus comprises a handle retainer that is fixed to part of the housing, wherein the handle retainer and part of the housing together provide pivoting and translational movement of the handle relative to the housing.

In some configurations, the handle is configured to move relative to the housing with a varying radius of movement.

In some configurations, the handle comprises a first pivot that is configured to move along a first pivot cavity, and the handle comprises a second pivot that is configured to move along a second pivot cavity. In some configurations, the first pivot cavity is generally J-shaped.

In some configurations, a portion of the first pivot cavity is arranged to enable upward movement of the first pivot when the handle is in the second position and the handle is used to lift the apparatus.

In some configurations, the second pivot cavity is oriented in a substantially forward-rearward direction of the apparatus.

In some configurations, the second pivot cavity is arcuate.

In some configurations, a portion of the second pivot cavity is arranged to enable upward movement of the second pivot when the handle is in the second position and the handle is used to lift the apparatus.

In some configurations, the handle comprises a body, a first pivot protrusion extending from the body, and a second pivot protrusion extending from the body, wherein the first and second pivot protrusions each have an exposed axial length and a transverse dimension, wherein the transverse dimension is greater than the axial length. In some configurations, the transverse dimension is at least twice the axial length.

In some configurations, the handle comprises an arm on said one side of the handle, wherein the arm is pivotally, or pivotally and translationally, connected to the housing. In some configurations, the handle comprises a cross-member that is connected to the arm.

In some configurations, there is a space between the housing and the cross-member on a side of the handle opposite to the arm, when the handle is in the second position.

In some configurations, a terminal end of the handle is arranged to be positioned generally above a centre of mass of the apparatus, when the handle is in the second position.

In some configurations, the handle and/or housing comprise one or more magnets to retain the handle in the lowered position.

Additionally, in accordance with certain features, aspects and advantages of at least one of the embodiments disclosed herein, an apparatus for delivering a flow of gas is disclosed, the apparatus comprising: a housing and a handle, wherein the handle is movably connected to the housing and is movable from a first position to a second position, wherein the housing and the handle comprise complementary interlock features, and wherein the complementary interlock features are arranged such that the interlock features engage with each other when the handle is in the second position and upward force is applied to the handle relative to the housing, and such that the interlock features engage with each other when the handle is in the first position.

In some configurations, the first position is a lowered position and the second position is a raised position. In alternative configurations, the first and/or second position are different position(s). For example, one or both of the first and second positions could be an intermediate position between the lowered position and the raised position.

In some configurations, the interlock features are disengaged from each other when the handle is in an intermediate position between the lowered position and the raised position. In some configurations, the interlock features are disengaged from each other when the handle is in any of a plurality of intermediate positions between the lowered position and the raised position.

In some configurations, the interlock features are disengaged from each other when the handle is in an intermediate position between the lowered position and the raised position. In some configurations, the interlock features are disengaged from each other when the handle is in any of a plurality of intermediate positions between the lowered position and the raised position.

In some configurations, the interlock features comprise a plurality of projections on one of the handle and the housing, and a plurality of complementary recesses on the other of the handle and the housing. In some configurations, at least one of the projections and the recesses comprise an angled face to assist with engagement of the projection(s) and the recess(es). In some configurations, the angled face(s) comprise forward face(s) of the projection(s) and/or the recess(es).

In some configurations, the apparatus comprises a heater and a liquid chamber bay for receipt of a liquid chamber. In some configurations, the handle encloses a portion of the liquid chamber bay when the handle is in the first position.

In some configurations, the handle is pivotally connected to the housing. In some configurations, only one side of the handle is pivotally connected to the housing. In some alternative configurations, two sides of the handle are pivotally connected to the housing.

In some configurations, the handle is pivotally and translationally connected to the housing. In some configurations, only one side of the handle is pivotally and translationally connected to the housing. In some alternative configurations, two sides of the handle are pivotally and translationally connected to the housing.

In some configurations, the apparatus comprises a handle retainer that is fixed to part of the housing, wherein the handle retainer and part of the housing together provide pivoting and translational movement of the handle relative to the housing.

In some configurations, the handle is configured to move relative to the housing with a varying radius of movement.

In some configurations, the handle comprises a first pivot that is configured to move along a first pivot cavity, and the handle comprises a second pivot that is configured to move along a second pivot cavity. In some configurations, the first pivot cavity is generally J-shaped.

In some configurations, a portion of the first pivot cavity is arranged to enable upward movement of the first pivot when the handle is in the second position and the handle is used to lift the apparatus.

In some configurations, the second pivot cavity is oriented in a substantially forward-rearward direction of the apparatus.

In some configurations, the second pivot cavity is arcuate.

In some configurations, a portion of the second pivot cavity is arranged to enable upward movement of the second pivot when the handle is in the second position and the handle is used to lift the apparatus.

In some configurations, the handle comprises a body, a first pivot protrusion extending from the body, and a second pivot protrusion extending from the body, wherein the first and second pivot protrusions each have an exposed axial length and a transverse dimension, wherein the transverse dimension is greater than the axial length. In some configurations, the transverse dimension is at least twice the axial length.

In some configurations, the handle comprises an arm on said one side of the handle, wherein the arm is pivotally, or pivotally and translationally, connected to the housing. In some configurations, the handle comprises a cross-member that is connected to the arm.

In some configurations, there is a space between the housing and the cross-member on a side of the handle opposite to the arm, when the handle is in the second position.

In some configurations, a terminal end of the handle is arranged to be positioned generally above a centre of mass of the apparatus, when the handle is in the second position.

In some configurations, the handle and/or housing comprise one or more magnets to retain the handle in the first position.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Features from one or more embodiments may be combined with features of one or more other embodiments. Additionally, more than one embodiment may be used together during a process of respiratory support of a patient.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It should be understood that alternative embodiments may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Figure 1:
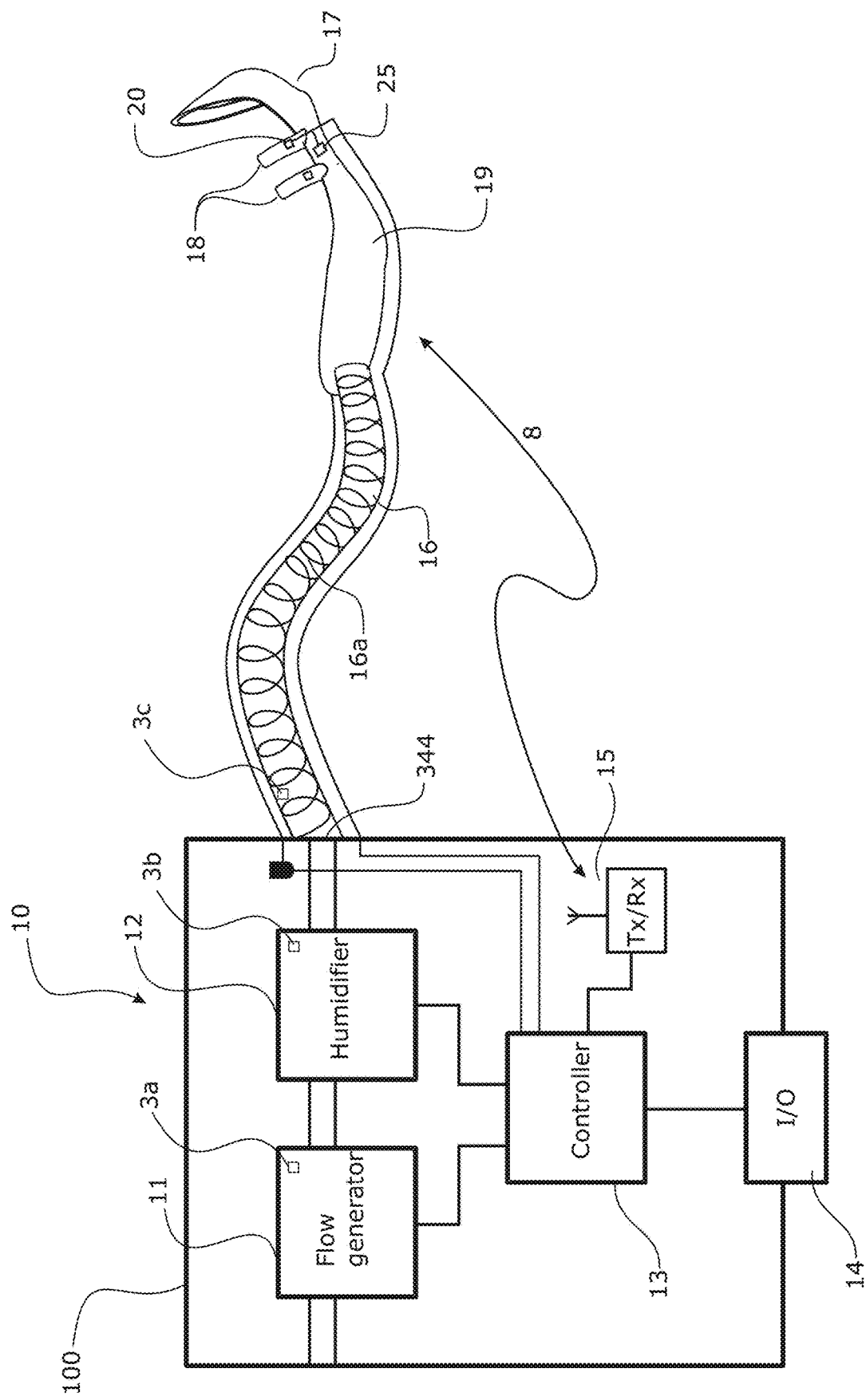
FIG. 1 shows in diagrammatic form a breathing assistance apparatus in the form of a flow therapy apparatus.

A flow therapy apparatus 10 is shown in FIG. 1. In general terms, the apparatus 10 comprises a main housing 100 that contains a flow generator 11 in the form of a motor/impeller arrangement, an optional humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gasflow) for delivery to a patient, operating the humidifier 12 (if present) to humidify and/or heat the generated gasflow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gasflow output 344 in the housing 100 of the flow therapy apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gasflow, which may be humidified, that is generated by the flow therapy apparatus 10 is delivered to the patient via the patient breathing conduit 16 through the cannula 17. The patient breathing conduit 16 can have a heater wire 16a to heat gasflow passing through to the patient. The heater wire 16a is under the control of the controller 13. The patient breathing conduit 16 and/or patient interface 17 can be considered part of the flow therapy apparatus 10, or alternatively peripheral to it. The flow therapy apparatus 10, breathing conduit 16, and patient interface 17 together form a flow therapy system.

General operation of a flow therapy breathing apparatus 10 will be known to those skilled in the art, and need not be described in detail here. However, in general terms the controller 13 controls the flow generator 11 to generate a gasflow of the desired flow rate, controls one or more valves to control the mix of air and oxygen or other alternative gas, and controls the humidifier 12 if present to humidify the gasflow and/or heat the gasflow to an appropriate level. The gasflow is directed out through the patient breathing conduit 16 and cannula 17 to the patient. The controller 13 can also control a heating element in the humidifier 12 and/or the heating element 16a in the patient breathing conduit 16 to heat the gas to a desired temperature that achieves a desired level of therapy and/or comfort for the patient. The controller 13 can be programmed with or can determine a suitable target temperature of the gasflow.

Operation sensors 3a, 3b, 3c, 20, 25 such as flow, temperature, humidity, and/or pressure sensors can be placed in various locations in the flow therapy apparatus 10 and/or the patient breathing conduit 16 and/or cannula 17. Output from the sensors can be received by the controller 13, to assist it to operate the flow therapy apparatus 10 in a manner that provides optimal therapy. In some configurations, providing optimal therapy includes meeting a patient's inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

The flow therapy apparatus 10 may comprise a high flow therapy apparatus. As used herein, "high flow" therapy refers to administration of gas to the airways of a patient at a relatively high flow rate that meets or exceeds the peak inspiratory demand of the patient. The flow rates used to achieve "high flow" may be any of the flow rates listed below. The flow therapy apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. 'High flow therapy' as used in this disclosure may refer to delivery of gases to an adult patient at a flow rate of greater than or equal to about 10 liters per minute (10 LPM), or to a neonatal, infant, or child patient at a flow rate of greater than or equal to about 1 liters per minute (1 LPM). In some configurations, for an adult patient 'high flow therapy' may refer to the delivery of gases to a patient at a flow rate of greater than or equal to about 10 litres per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and about 25 LPM. Therefore, a high flow therapy apparatus for use with either an adult patient or a neonatal, infant, or child patient, may deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%. High flow therapy has been found effective in meeting or exceeding the patient's inspiratory demand, increasing oxygenation of the patient and/or reducing the work of breathing. Additionally, high flow therapy may generate a flushing effect in the nasopharynx such that the anatomical dead space of the upper airways is flushed by the high incoming gas flows.

This creates a reservoir of fresh gas available of each and every breath, while minimising re-breathing of carbon dioxide, nitrogen, etc.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As shown in FIGS. 2 to 48 and described below, the flow therapy apparatus 10 has various features to assist with the functioning, use, and/or configuration of the apparatus 10.

As shown in FIGS. 2 to 4, and 27 to 30, the flow therapy apparatus 10 comprises a main housing 100. The main housing 100 has a main housing upper chassis 102 and a main housing lower chassis 202.

The main housing upper chassis 102 has a peripheral wall arrangement 106. The peripheral-wall arrangement 106 defines a humidifier or liquid chamber bay 108 for receipt of a removable liquid chamber 300. The removable liquid chamber 300 contains a suitable liquid such as water for humidifying gases that will be delivered to a patient.

In the form shown, the peripheral wall arrangement 106 of the main housing upper chassis 102 comprises a short substantially vertical left side outer wall 110 that is oriented in a front-to-rear direction of the main housing 100, a substantially vertical left side inner wall 112 that is oriented in a front-to-rear direction of the main housing 100, and an interconnecting wall 114 that extends between and interconnects the upper ends of the left side inner and outer walls 110, 112. The main housing upper chassis 102 further comprises a short substantially vertical right side outer wall 116 that is oriented in a front-to-rear direction of the main housing 100, a substantially vertical right side inner wall 118 that is oriented in a front-to-rear direction of the main housing 100, and an interconnecting wall 120 that extends between and interconnects the upper ends of the right side inner and outer walls 116, 118. The interconnecting walls 114, 120 are angled towards respective outer edges of the main housing 100, but could alternatively be substantially horizontal or inwardly angled.

The main housing upper chassis 102 further comprises a short substantially vertical rear outer wall 122. An upper part of the main housing upper chassis 102 comprises a forwardly angled surface 124. The surface 124 has a recess for receipt of a display and user interface module. An interconnecting wall 128 extends between and interconnects the upper end of the rear outer wall 122 and the rear edge of the surface 124.

The liquid chamber bay 108 has a substantially vertical wall portion 134 that terminates at a substantially horizontal floor portion 136 of the liquid chamber bay 108. The left side inner wall 112, right side inner wall 118, wall portion 134, and floor portion 136 together define the liquid chamber bay 108. The floor portion 136 of the liquid chamber bay 108 has a recess to receive a heater arrangement such as a heater plate 140 or other suitable heating element(s) for heating liquid in the liquid chamber 300 for use during a humidification process.

The floor portion 136 of the liquid chamber bay 108 terminates short of the front edge of the left side inner wall 112 and the right side inner wall 118 to form a downwardly extending lip 142. The lip 142 comprises a recess that enables a user to insert their finger under the front part of a handle portion 506 of a handle/lever 500 to lift the handle from a lowered position. The handle/lever 500 is for use in assisting with insertion of the liquid chamber 300 and for carrying the apparatus 10, as will be described further below. The liquid chamber bay 108 further comprises opposed guide features in the form of left side and right side horizontally extending guide rails 144, 146 which extend toward a centre of the bay 108 from the respective left and right side inner walls 112, 118 to assist with guiding the liquid chamber 300 into position in the liquid chamber bay 108 as will be described in detail below.

The main housing lower chassis 202 is attachable to the upper chassis 102, either by suitable fasteners or integrated attachment features such as clips for example. The main housing lower chassis 202 comprises a substantially vertical left side outer wall 210 that is oriented in a front-to-rear direction of the main housing 100 and is contiguous with the left side outer wall 110 of the upper chassis 102, and a substantially vertical right side outer wall 216 that is oriented in a front-to-rear direction of the main housing 100 and is contiguous with the right side outer wall 116 of the upper chassis 102. The main housing lower chassis 202 further comprises a substantially vertical rear outer wall 122 that is contiguous with the rear outer wall of the upper chassis 102.

An underside of the lower housing chassis 202 comprises a bottom wall. A motor recess for receipt of a removable motor and/or sensor module is provided in the lower chassis 202. A recess opening may be provided in the bottom wall to enable the motor and/or sensor module to be inserted in the recess. The motor and/or sensor module may be removable or non-removable.

Figure 3:
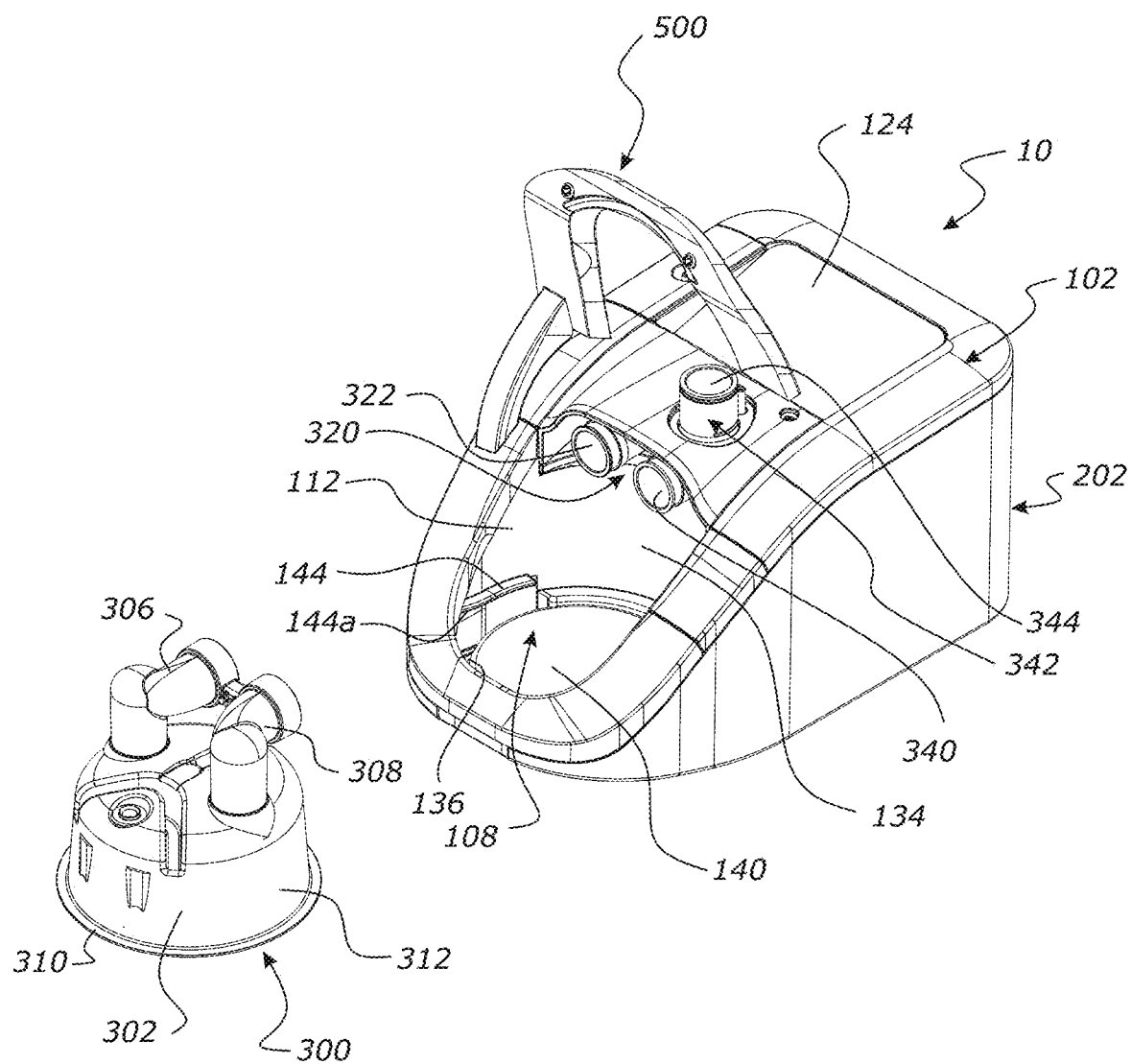
FIG. 3 shows the apparatus with the liquid chamber removed from the liquid chamber bay.

With reference to FIG. 3, the removable liquid chamber 300 comprises an outer housing 302 defining a liquid reservoir, a liquid chamber gases inlet port 306 in fluid communication with the liquid reservoir, and a liquid chamber gases outlet port 308 in fluid communication with the liquid reservoir. A baffle may be provided internally in the liquid reservoir to define a flow path of gases through the liquid chamber 300. A lower edge of the liquid chamber 300 comprises an outwardly directed annular flange 310 which interacts with the guide rails 144, 146 in the liquid chamber bay 108 for locating and retaining the liquid chamber 300 in the liquid chamber bay 108. The flange 310 extends outwardly from the base of a peripheral wall 312 of the liquid chamber 300. A bottom wall of the liquid chamber 300 is heat conducting and is adapted for resting on the heater plate 140 for heating liquid in the liquid chamber 300.

The apparatus 10 comprises a connection manifold arrangement 320 for fluid coupling of the liquid chamber 300 to the apparatus 10. The liquid chamber 300 can be fluidly coupled to the apparatus 10 in a linear slide-on motion in a rearward direction of the liquid chamber 300 into the liquid chamber bay 108, from a position at the front of the housing 100 in a direction toward the rear of the housing 100. The connection manifold arrangement 320 comprises a manifold gases outlet port 322 that is in fluid communication, via a fixed L shaped elbow 321, with a gasflow passage from the motor and/or sensor module. The fixed L shaped elbow 321 receives gases from the outlet of the blower of the motor and/or sensor module, and connects to the inlet port 306 of the liquid chamber bay 300. The lower portion of the elbow extends downwardly into the interior of the gasflow passage tube 264 (FIG. 43), to receive gases from the motor and/or sensor module.

The connection manifold arrangement 320 further comprises a humidified gases return port 340 that is embodied in a removable elbow 342. The removable elbow 342 is L-shaped, and further comprises a patient outlet port 344 for coupling to the patient breathing conduit 16 to deliver gases to the patient interface 17. The manifold gases outlet port 322, manifold gases inlet port 340, and patient outlet port 344 each comprise soft seals such as O-ring seals or T-seals (not shown) to provide a sealed gases passageway between the apparatus 10, the liquid chamber 300, and the patient breathing conduit 16.

The liquid chamber gases inlet port 306 is complementary with the connection manifold gases outlet port 322, and the liquid chamber gases outlet port 308 is complementary with the connection manifold gases inlet port 340. The axes of those ports are preferably parallel to enable the liquid chamber 300 to be inserted into the liquid chamber bay 108 in a linear movement.

The apparatus 10 has air and oxygen (or alternative auxiliary gas) inlets in fluid communication with the motor to enable the motor to deliver air, oxygen, or a suitable mixture thereof to the liquid chamber 300 and thereby to the patient.

Various aspects of the device will now be described in more detail.

In addition to the features described above, the apparatus has a component coupling that substantially inhibits a component (such as the removable elbow 342) from moving relative to the housing in a first direction, and a cover coupling that substantially inhibits a cover 5105a, 15105a from moving relative to the housing 100 in a second direction. The housing 100 and cover 5105a, 15105a may have a magnetic coupling, complementary locating features, or both magnetic coupling and complementary locating features.

In some embodiments having complementary locating features, the locating features of the housing and the cover may be interlocking features adapted to form an interlock. In other embodiments having complementary locating features, the locating features of the housing and the cover may not form an interlock.

In some embodiments the first and second direction are substantially perpendicular. For example, the first direction is substantially vertical and the second direction is substantially horizontal. The first direction may be about 75°, about 80°, about 85°, about 90°, about 95°, about 100°, or about 105°. The second direction may be about 15°, about 10°, about 5°, exactly horizontal, about −5°, about 110°, or about −15°.

With reference to the embodiment of the cover and screen carrier shown in FIGS. 5 to 9, the apparatus 10 has a magnetic coupling system arranged to magnetically couple a cover to a component of the housing 100. The component of the housing 100 is the screen carrier 3102, but may be any other suitable component of the housing 100. Each of the housing 100 and cover 5105a having complementary locating features that are adapted to locate and align the cover 5105a and the apparatus 10 relative to each other to allow for said magnetic coupling. The locating features of the housing and the cover are interlocking features adapted to form an interlock. The interlock is an engagement between the cover 5105a and housing 100 that align the housing and cover in a predetermined orientation and maintain that orientation. The interlock prevents the housing and cover moving relative to each other in at least one direction, but allow movement in another direction. In some embodiments, the locating features may not be adapted to form an interlock.

Figure 8:
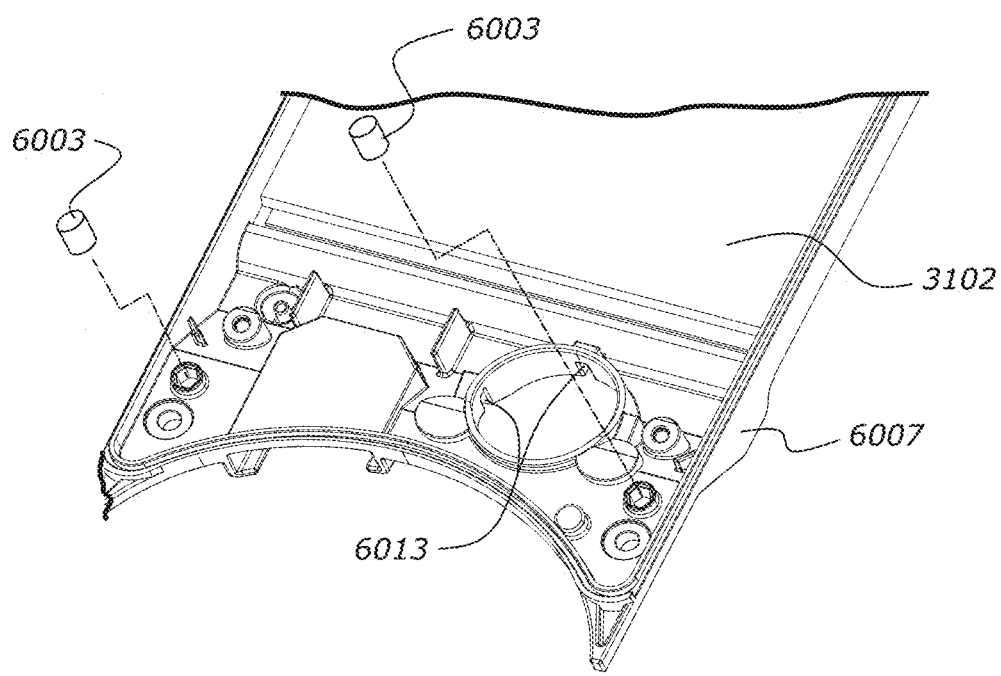
FIG. 8 is a perspective view from below of the screen carrier of FIG. 6.

The magnetic coupling system has at least one magnet 6003 associated with the screen carrier 3102 and at least one other magnet 6001 associated with the cover 5105a. In the embodiment shown, the magnetic coupling system comprises multiple magnets 6001, 6003 associated with each of the housing 100 and cover 5105a. The magnets 6001, 6003 are attached by interference fit and/or adhesive. In particular, the magnets 6001, 6003 are attached to upstands or supports 6005 and are received by the apertures 6006 provided by the supports 6005. The apertures 6006 of the supports 6005 may have a reduced diameter, or platform, located away from an end of the support 6005 to prevent the magnets 6001, 6003 from being inserted too far, and to ensure the magnets 6001, 6003 are located. The supports 6005 of the cover 5105a have internal ribs or other projections that grip the magnets 6001 as they are inserted into the supports and provide an interference fit. FIG. 8 shows the support having a generally hexagonal cross-section for receiving the magnets 6003. The support 6005 may have other shaped cross-sections for receiving the magnets 6003 with an interference fit for example a quadrilateral or octagonal.

In an alternative embodiment, the magnetic coupling system may comprise at least one magnet 6003 associated with one of the screen carrier 3102 or cover and at least one ferrous part associated with the other of the housing 100 or cover.

The magnets 6001, 6003 are provided to the cover 5105a and screen carrier 3102 such that they attract when the cover 5105a is coupled to the screen carrier 3102 in a predetermined orientation of the cover 5105a relative to the screen carrier 3102. The magnets 6001, 6003 also repel when the cover 5105a is offered to the screen carrier 3102 in at least one orientation other than said predetermined orientation. For example in a predetermined orientation the magnets 6001 provided to the cover 5105a may present an opposing magnetic pole (for example north) to the magnetic pole (for example south) of a magnet 6003 provided to the screen carrier 3102, such that the cover 5105a and screen carrier 3102 are attracted to each other. Alternatively, or additionally in an orientation other than the predetermined orientation the magnets 6001 provided to the cover 5105a may present the same magnetic pole to the magnetic pole of a magnet 6003 provided to the screen carrier 3102, such that the cover 5105a and screen carrier 3102 are repelled from each other (for example both poles could be north poles).

Figure 7:
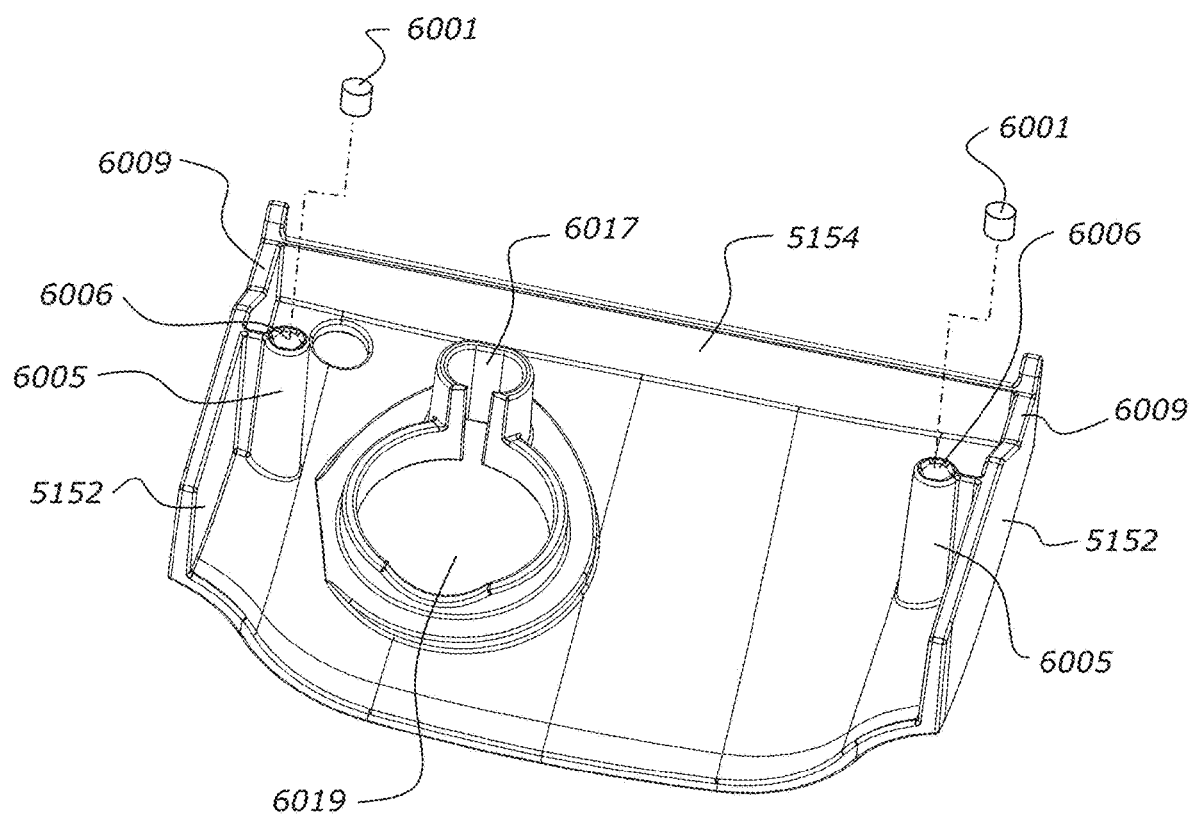
FIG. 7 is a perspective view from below of the cover of FIG. 5.

The magnets 6001 may be embedded in the cover 5105a and covered by a surface of the cover 5105a, however in the embodiment as shown in FIG. 7 the magnets 6001 are not covered by a surface of the cover 5105a. The magnets 6003 are embedded in the screen carrier 3102 and covered by a surface of the screen carrier 3102. The material covering the magnets is relatively thin so that the material does not significantly affect the strength of the bond between the magnet(s) 6001 of the cover 5105a and the magnet(s) 6003 of the screen carrier 3102. Covering the magnets 6001, 6003 with the material provides aesthetic benefits and provides a relatively easy cleaning surface. The magnetic coupling system provide easy locating of the cover 5105a to the screen carrier 3102 for a user and also provide the user with tactile feedback that the cover 5105a is positioned correctly.

The locating features of one of the cover 5105a or screen carrier 3102 comprise at least one projection 6007 and the locating features of the other of the cover 5105a or screen carrier 3102 comprise at least one recess 6009. The at least one projection and the at least one recess form the interlock. The interlocking features prevent relative movement between the cover and the housing 100 in an axis substantially parallel to a direction in which the elbow is removed.

In the embodiment shown, the cover 5105a comprises the recesses 6009 (one in each side wall 5152) and the screen carrier 3102 comprises the projection 6007. The projection 6007 and recesses 6009 prevent, or at least substantially inhibit, the cover from moving relative to the screen carrier 3102 (or housing or the apparatus) for example when the chamber is removed from the apparatus 10—the removable elbow is held beneath the cover 5105a as described below and is also prevented, or at least substantially inhibited, from being removed when the chamber is removed.

Figure 6:
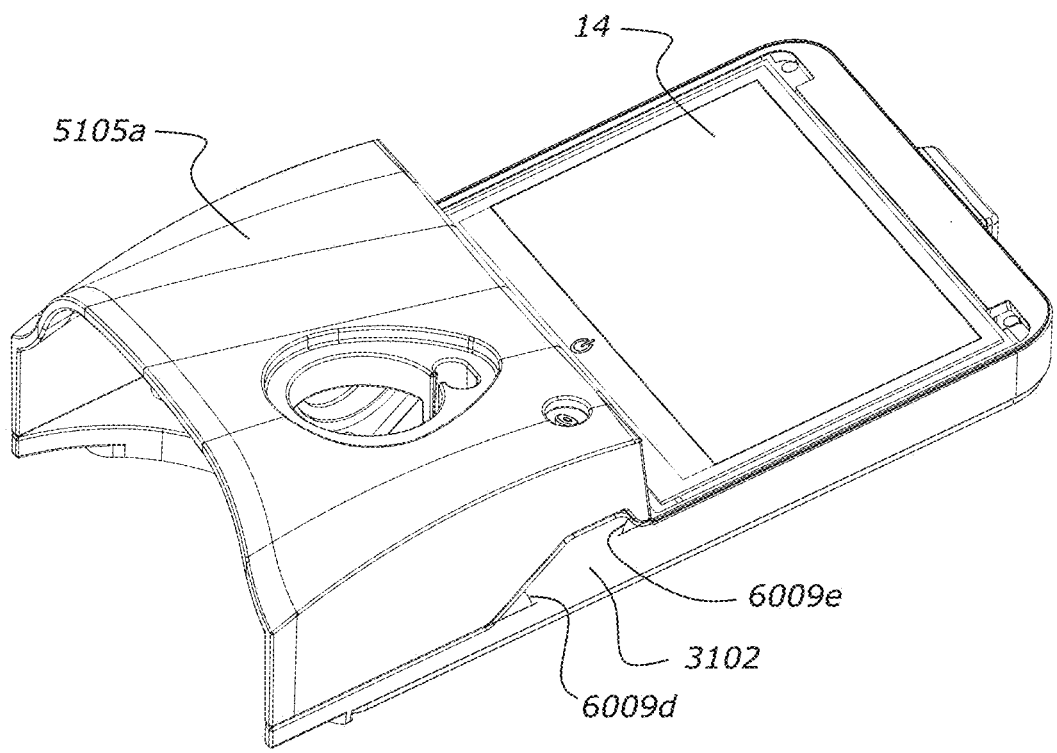
FIG. 6 is a perspective view of the cover of FIG. 5 and one embodiment of a screen carrier assembled together.

The recesses 6009 comprise angled rear and front faces 6009a, 6009c with a generally flat portion 6009b between. The projection comprises angled rear and front faces 6007a, 6007c that are complementary to the angled rear and front faces of the recess with a generally flat portion 6007b between. As shown in FIG. 6, the rear faces 6007a, 6009a can define an angle 6009e and the front faces 6007c, 6009c can define an angle 6009d. The angle 6009d, 6009e is measured with reference to a horizontal axis and may be between a nearly horizontal angle to a generally vertical angle. For example, the angle 6009d, 6009e may be between about 5 degrees to about 90 degrees, about 10 degrees to about 85 degrees, about 15 degrees to about 80 degrees, about 20 degrees to about 75 degrees, about 25 degrees to about 70 degrees, about 30 degrees to about 65 degrees, about 35 degrees to about 60 degrees, about 40 degrees to about 55 degrees, about 45 degrees to about 50 degrees. The embodiment shown has one projection 6007 in the form of a ridge that extends across the screen carrier 3102. In an alternative embodiment, the screen carrier 3102 or other component of the housing 100 may have more than one projection 6007.

Figure 9:
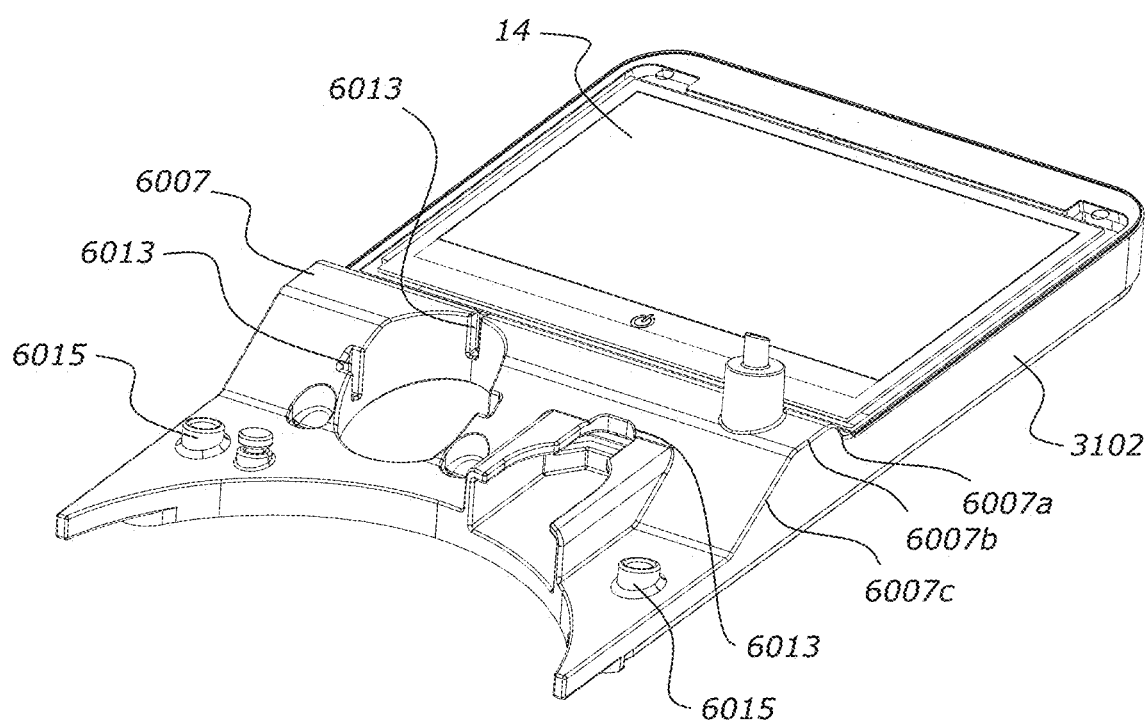
FIG. 9 is a perspective view from above of the screen carrier of FIG. 6.

FIG. 9 shows the rear face 6007a of projection 6007 is of a shorter length than the length of the front face 6007c of projection 6007. This may assist in the orientation of the cover 5105a and the screen carrier 3102, as there is only one orientation in which the cover 5105a can engage with top surface of the carrier. The recesses and projection may have other asymmetrical profiles, such as a curved profile. It will be appreciated that the front face 6007c of the projection 6007 may be shorter than the length of the rear face 6007a of projection 6007.

FIG. 9 also shows that screen carrier having bosses 6015. The bosses 6015 may allow for the passage of a fastener to couple the screen carrier 3102 to part of the apparatus. The bosses 6015 may stand proud, or be recessed from a surface of the screen carrier 3102. Such a configuration may allow for prevention of the accumulation of material, and allow for easy cleaning of the surface of the screen carrier 3102.

The locating interlocking features may be adapted to prevent relative movement between the cover 5105a and the housing 100. In particular, the locating features comprise the side walls 5152 of the cover 5105a. The locating features may comprise a back wall 5154 and may additionally or alternatively comprise a front wall of the cover 5105a. The lower surface of one or more of the walls may also be a locating feature that interacts with a corresponding surface of the housing. The back wall 5154 is recessed from an edge of the cover 5105a. The front wall, if provided, may also be recessed from an edge of the cover 5105a. This helps ensure better engagement between the cover 5105a and the screen carrier, and acts as a barrier to water ingress. Once engaged, the cover 5105a cannot move, or is at least substantially inhibited from moving relative to the housing 100. A recessed back wall 5154 provides for a region of the cover 5105a which can be grasped by a user, and may help in the removal and/or engagement of the cover from or to the screen carrier 3102.

Figure 2:
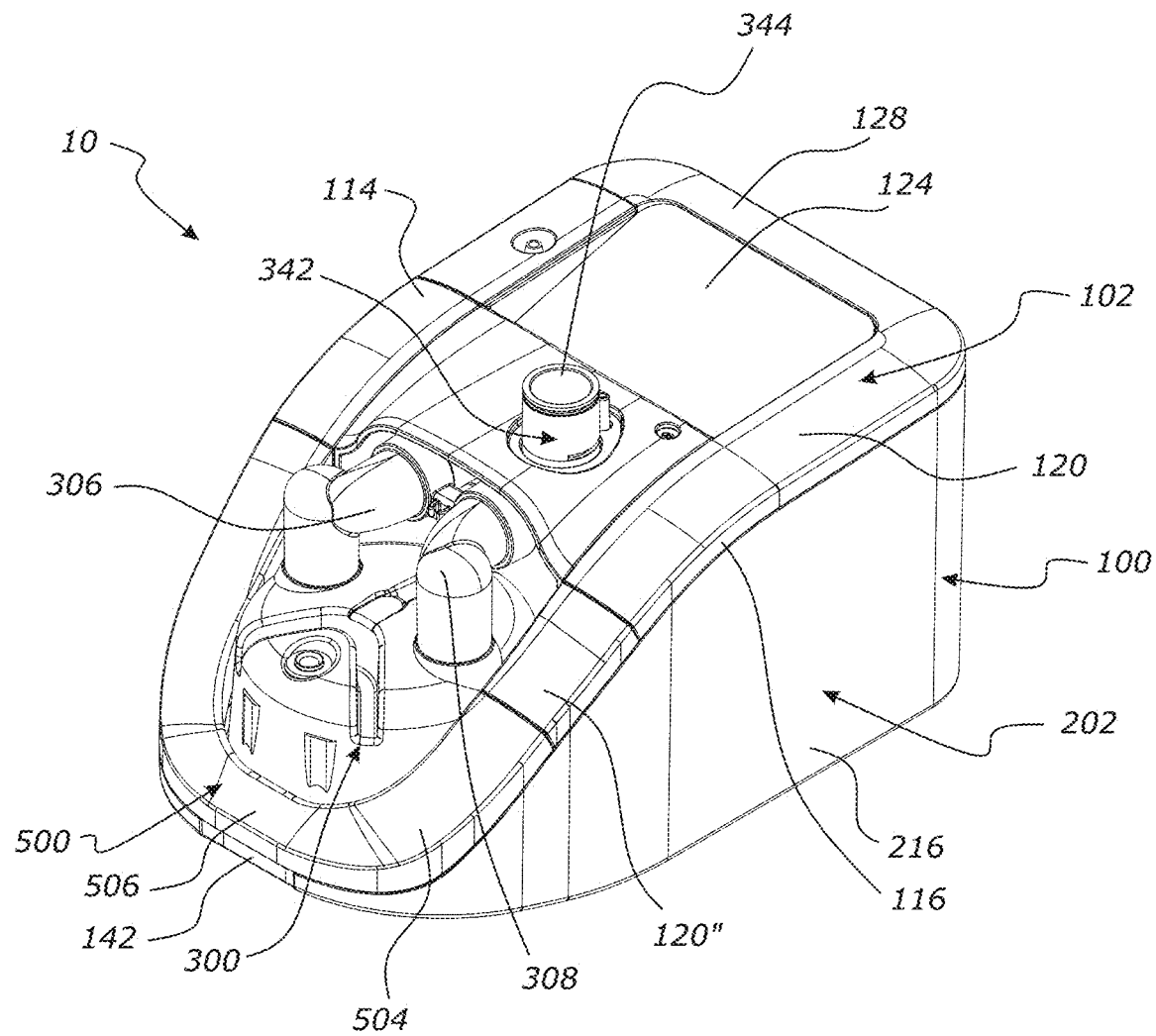
FIG. 2 is a front, right side overhead perspective view of the flow therapy apparatus with a humidifier chamber in position and a lowered handle/lever.

With reference to FIG. 2, the cover 5105a covers, retains, assists with the retention of and/or positions a component of the apparatus. In particular, the cover 5105a covers, retains, assists with retention of, and/or positions the removable elbow 342.

It will be understood that the direction of movement that is being prevented is the direction of movement required for removing the removable elbow 342. That is, the direction of movement being prevented is substantially perpendicular to the direction of movement for attaching the cover: the cover moves vertically to attach over the elbow, and then prevents horizontal movement of the removable elbow 342.

Figure 11:
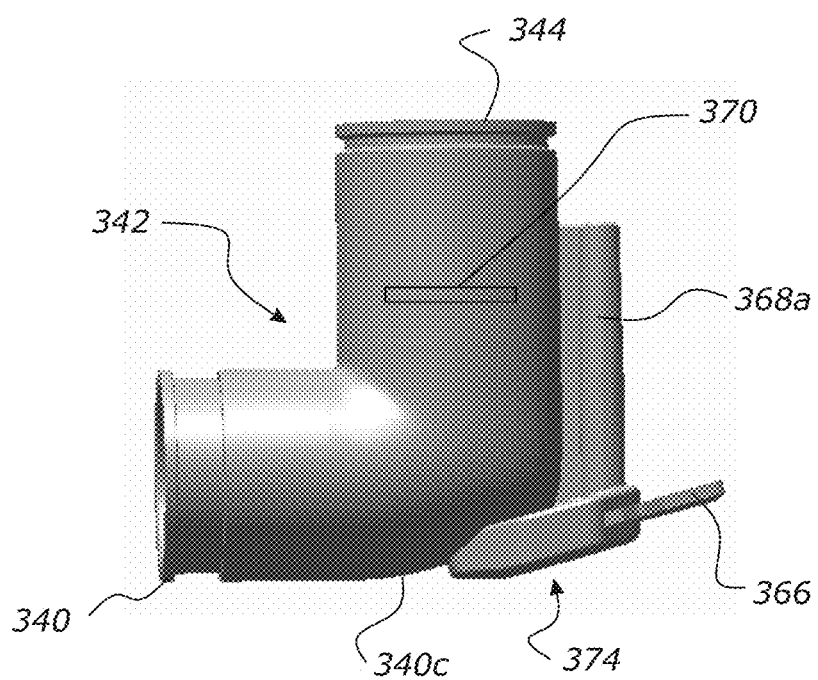
FIG. 11 shows a removable elbow.
Figure 12:
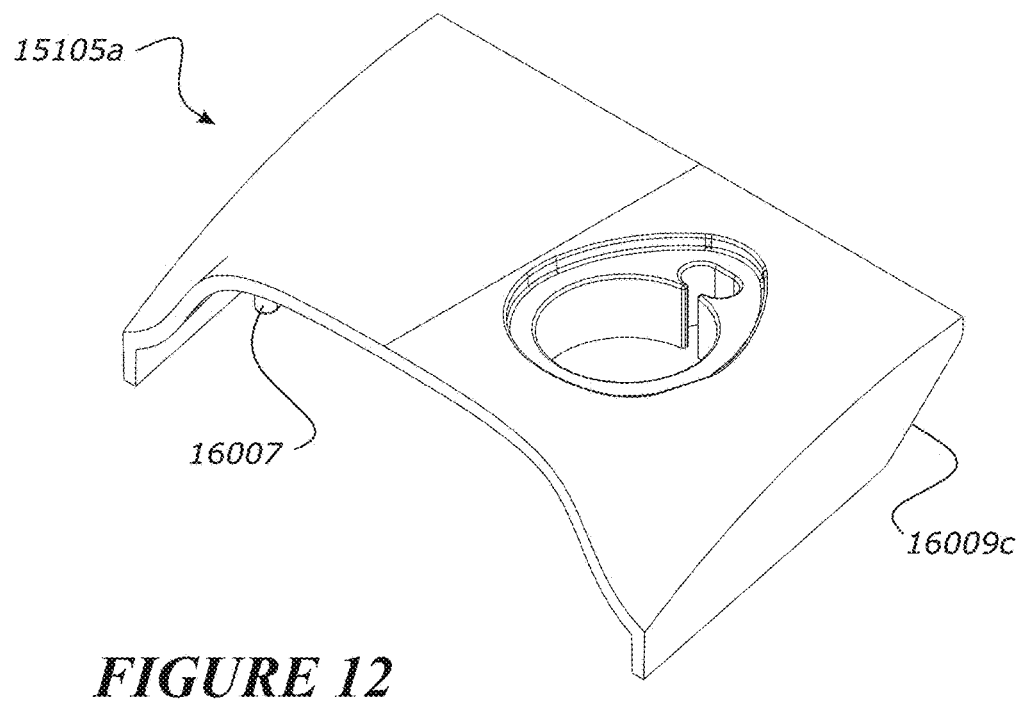
FIG. 12 is a perspective view from above of another embodiment of the cover.
Figure 13:
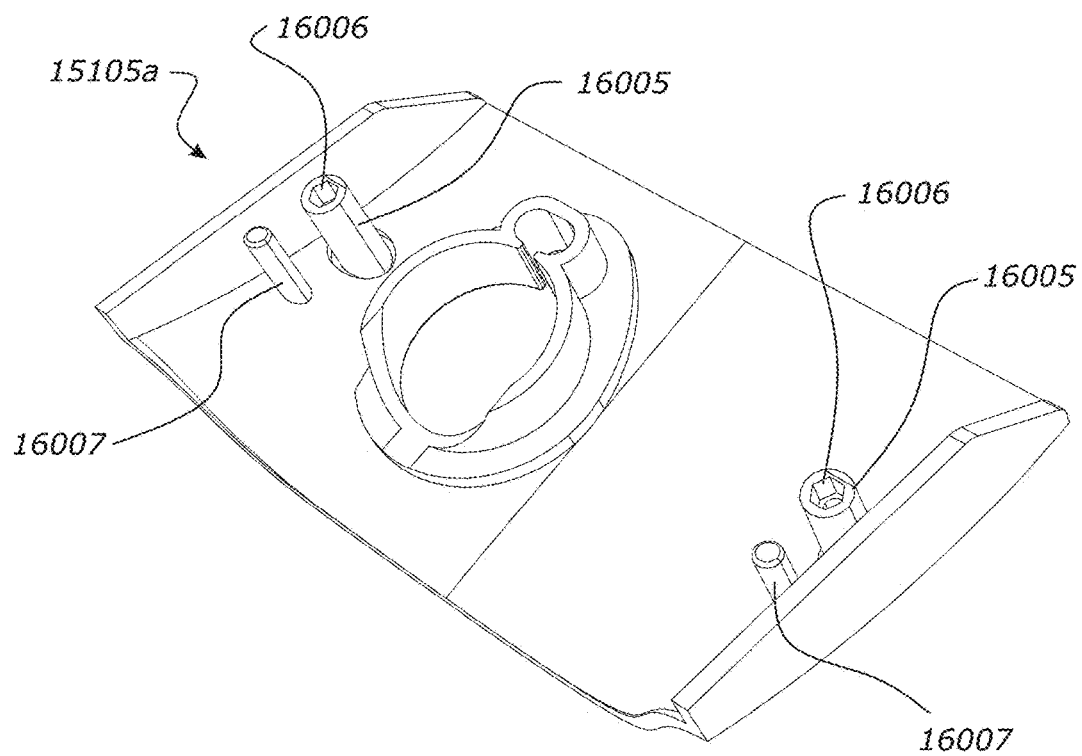
FIG. 13 is a perspective view from below of the cover of FIG. 12.
Figure 14:
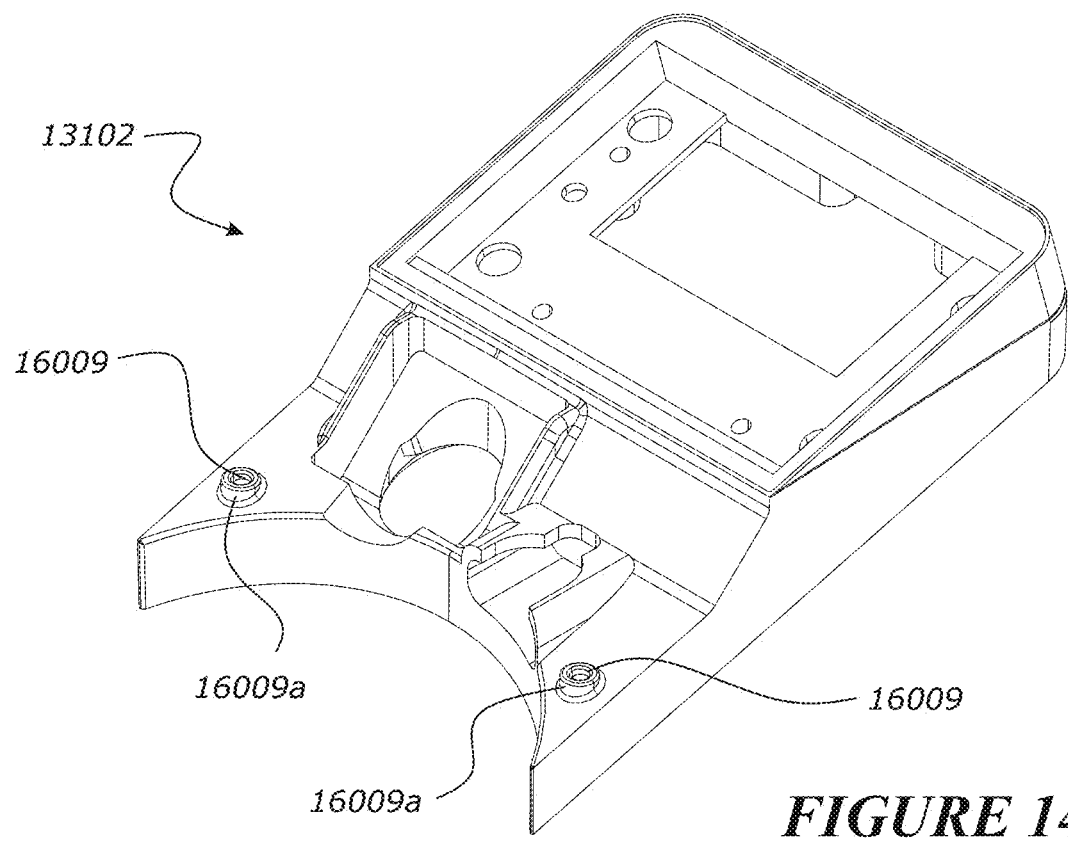
FIG. 14 is a perspective view from above of another embodiment of the screen carrier.
Figure 15:
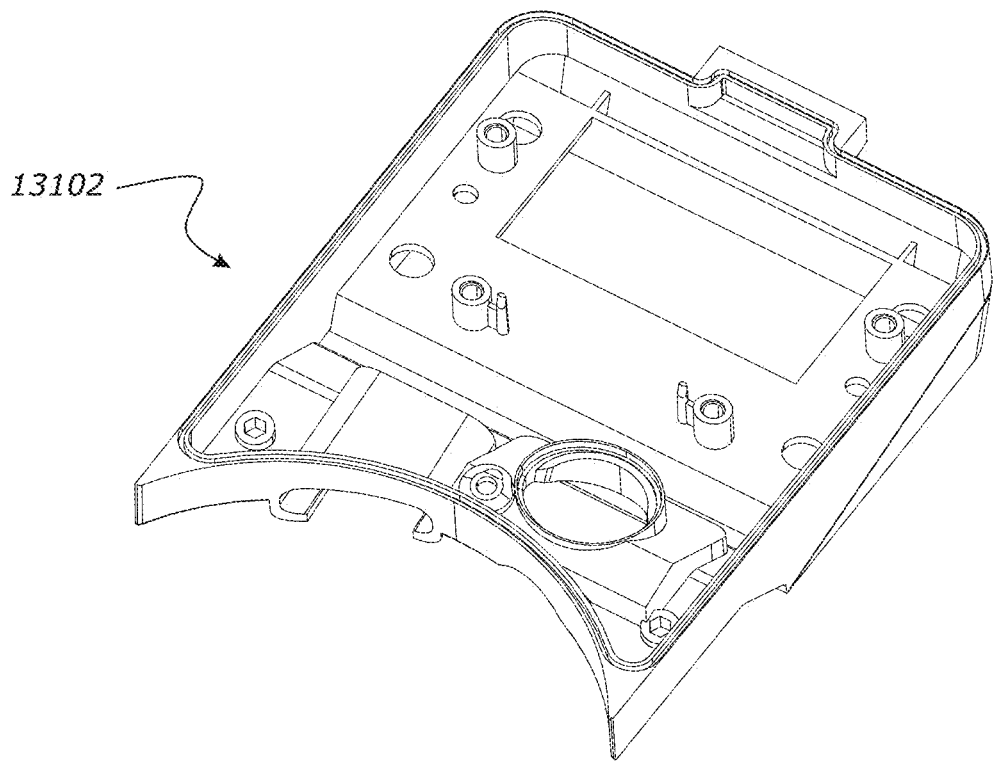
FIG. 15 is a perspective view from below of the screen carrier of FIG. 14.
Figure 16:
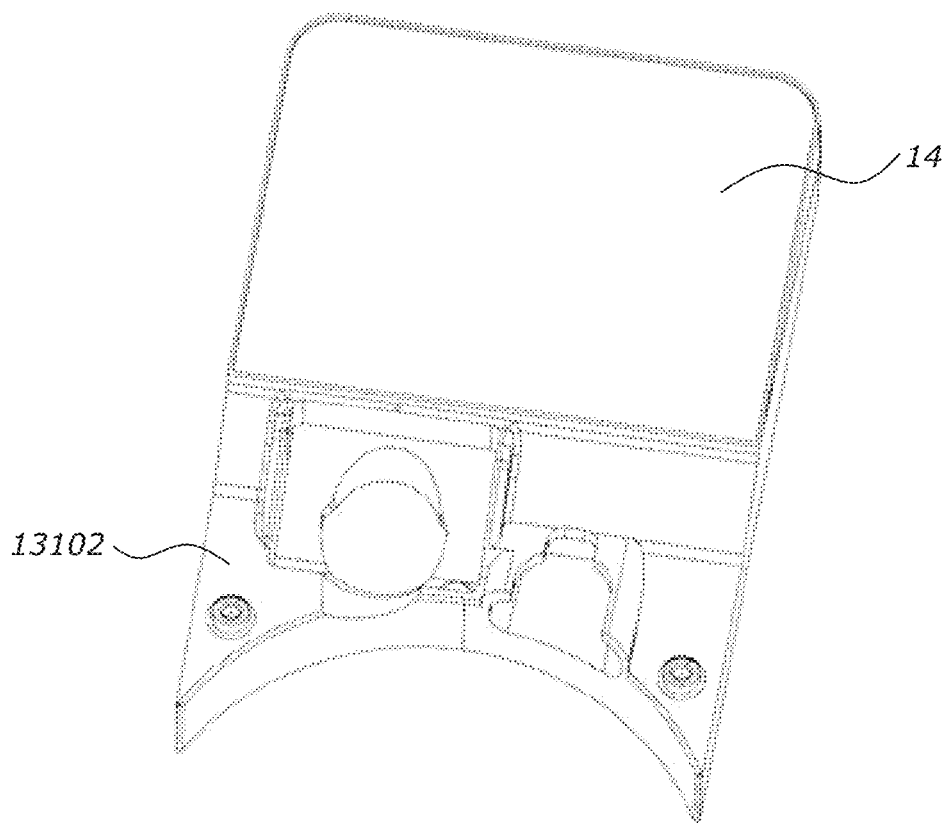
FIG. 16 is a perspective view of the cover of FIG. 12 and the screen carrier of FIG. 14 assembled together.

FIG. 11 shows the removable elbow 342 for use in the flow therapy apparatus. The elbow has an inlet port 340 and an outlet port 344. The elbow 342 has a pneumatic and/or an electrical connection. In particular, the elbow has a PCB connector 366 and a chimney portion 368a. The elbow has a plastic support portion 374 with angled edges to allow for recesses on the PCB connector 366. The base at the inner end of the horizontal limb (corresponding to the manifold gases inlet port 340) of the removable elbow has an upwardly curved region 340c prior to the bend in the elbow to assist with tooling. The elbow comprises depressions 370 on part of the gasflow outlet 344 for engagement with complementary protrusions on a sliding locking collar connected to the heated patient interface tube 16.

As described above, the elbow 342 is a removable component. The cover 5105a may alternatively cover, retain, and/or position other elements of the flow path. The cover 5105a has an aperture 6019 to allow for passage of the outlet port 344 of the elbow 342.

The cover 5105a has a lead-in feature 6017 to engage part of the elbow upon initial engagement, to ensure correct alignment between the cover 5105a, the breathing apparatus, and the removable elbow 342. The lead-in feature is a generally oval shaped aperture 6017 that connects with the aperture 6019 that receives the elbow 342. The lead-in feature engages with one or more of the features of the removable elbow for example pneumatic or electrical connection features of the removable elbow. In the embodiment shown, the lead-in feature 6017 receives the chimney portion 368a of the elbow 342. Once assembled, the cover 5105a prevents the elbow 342 from being removed in a horizontal direction.

Figure 4:
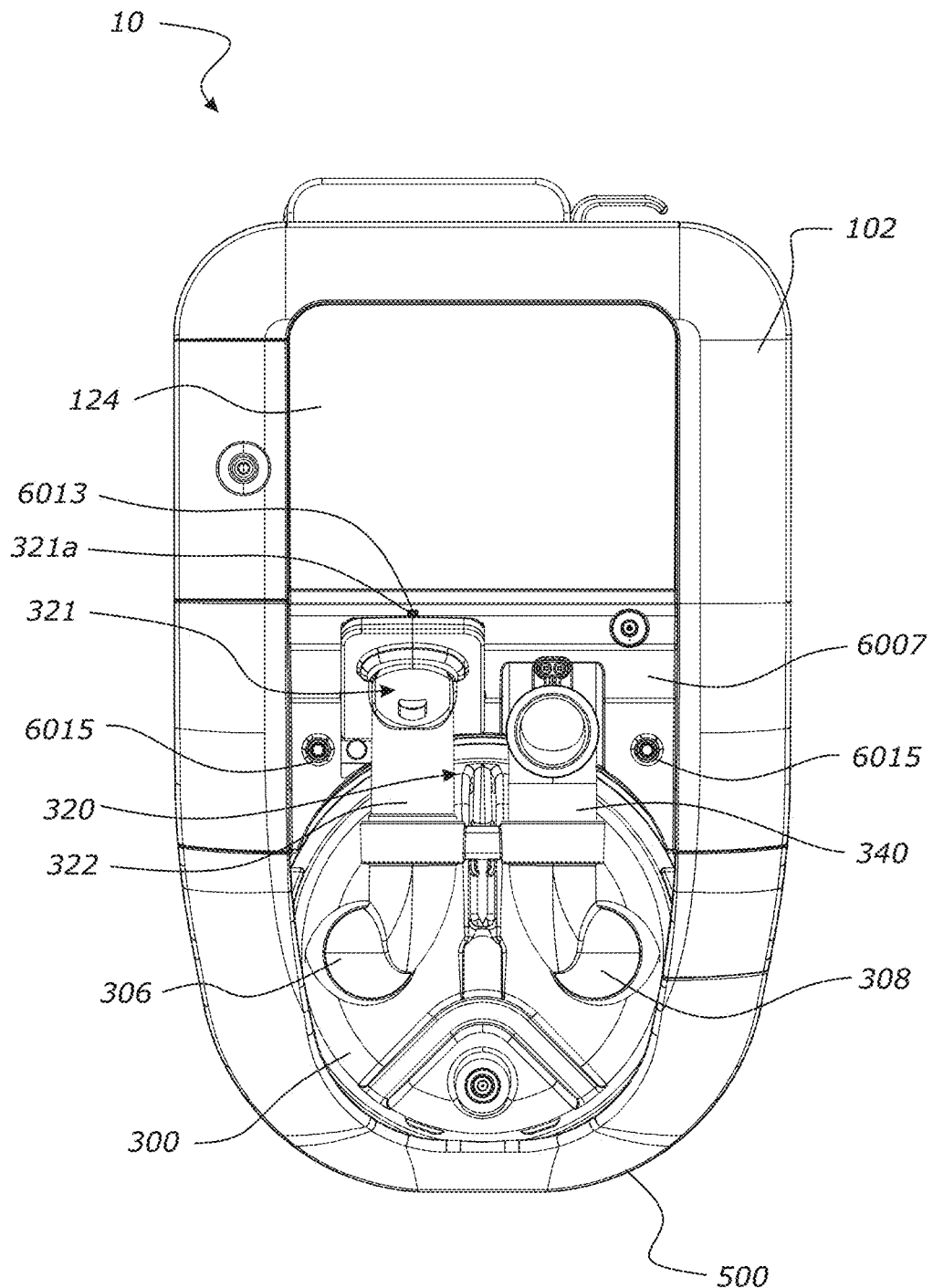
FIG. 4 is a top view of the apparatus with the cover removed.

The screen carrier 3102 also has lead-in features 6013 to engage part of the fixed elbow 321 upon initial engagement, to ensure correct alignment between the screen carrier 3102, the breathing apparatus, and the fixed elbow 321. The lead-in features are guide slots that engage with one or more of ridges 321a of the fixed elbow 321 (FIG. 4).

Figure 5:
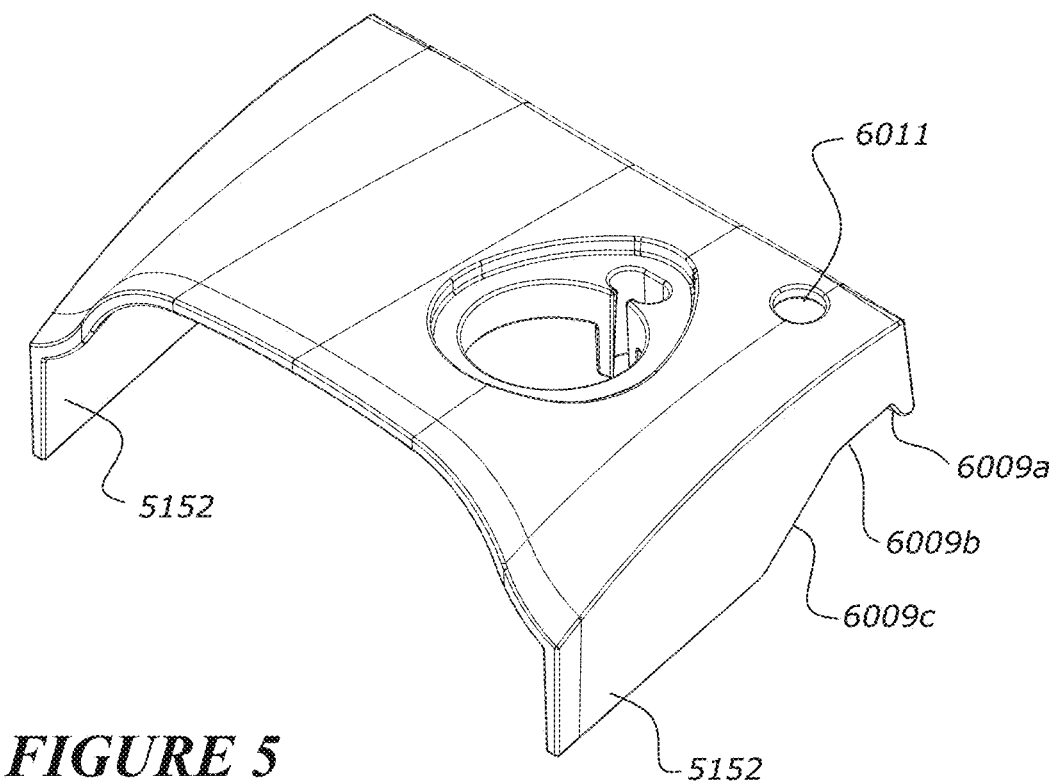
FIG. 5 is a perspective view of one embodiment of the cover.

The projection 6007 and complementary recesses 6009 associated with the screen carrier 3102 and the cover 5105a allow the cover 5105a and screen carrier 3102 to be assembled together in a predetermined orientation of the cover 5105a relative to the screen carrier 3102 and prevent the cover 5105a and screen carrier 3102 being assembled together when the cover 5105a is offered to the screen carrier 3102 in at least one orientation other than said predetermined orientation. FIG. 5 shows that the side walls 5152 of the cover 5105a are asymmetrical about a transverse axis.

When the removable elbow 342 is coupled to the housing 100, it can only be removed horizontally, and therefore the coupling with the housing 100 inhibits motion in the vertical direction. If a vertical force is applied to the removable elbow 342 (such as when the tube is removed) then the elbow coupling will prevent the removable elbow 342 from being removed.

Due to the removable elbow 342 passing vertically through the cover 5105a, the cover 5105a and the removable elbow 342 are prevented from moving relative to each other in a horizontal direction.

When the cover 5105a is coupled to the housing 100 with an interlock it can only be removed vertically, and therefore inhibits motion in the horizontal direction. If a horizontal force is applied to the removable elbow 342 (such as when the chamber is removed) then the configuration of the cover coupling to the housing 100 over the removable elbow 342 prevents the elbow from being removed.

When the cover 5105a couples to the housing 100 with a magnetic coupling, then the magnets inhibit (but may not fully prevent) motion in a horizontal direction. In this configuration, the retaining force of the elbow connection would also inhibit (but may not fully prevent) motion in the horizontal direction. If a horizontal force is applied to the removable elbow 342 (such as when the chamber 300 is removed) then the configuration of the cover coupling to the housing 100 over the removable elbow 342 inhibits this force and acts as a retaining feature. Additionally, the retaining force of the removable elbow 342 would also inhibit this force, and would also act as a retaining feature. One or a combination of the forces from these retaining features would be enough to prevent the removable elbow 342 from being removed.

FIG. 5 shows the cover 5105a comprises an aperture 6011 extending through the top of the cover 5105a. This aperture is an optional feature and the cover 5105a may comprise additional apertures, if required. The aperture may provide for connection to a port or other connection of the screen carrier 3102 through the cover 5105a.

Figure 10:
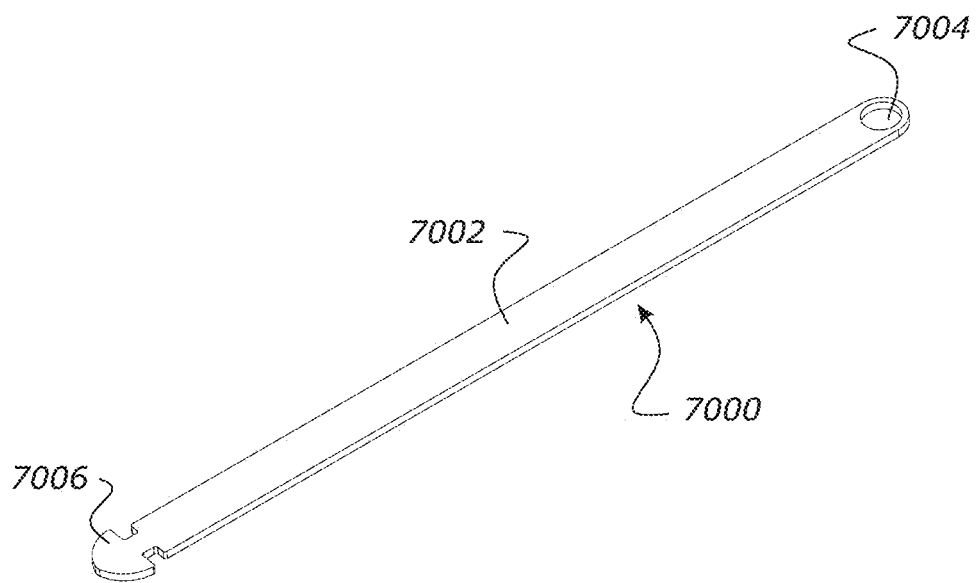
FIG. 10 is a perspective view of an optional tether.

The cover 5105a may be coupled to the screen carrier 3102, and thereby to the main housing, by a flexible tether 7000 shown in FIG. 10. The tether comprises an elongate body 7002, an aperture 7004 at or toward a first end of the tether, and enlarged head 7006 at or toward an opposite second end of the tether. The tether 7000 is coupled to the cover 5105a by inserting the enlarged head 7006 through a slot (not shown) in the cover 5105a. The enlarged head inhibits removal of the tether from the cover 5105a. The tether 7000 is coupled to the carrier 3102 by inserting the first end of the tether between the carrier 3102 and the upper chassis 102 so its aperture 7004 is aligned with the respective aperture, and is maintained in position by the fastener that is used to fasten the carrier 3102 to the upper-chassis 102. The tether may be manufactured from a suitable resilient and robust material, such as TPU for example. The cover 5105a may pivot at one end relative to the carrier 3102. The cover 5105a may comprise a hook (not shown) which one end of the tether can connect to, the screen carrier 3102 may also have a hook or other feature to which the other end of the tether can be connected. In an alternative embodiment, one end of the tether may connect to the removable elbow 342 and the other end may connect to the cover.

With reference to FIGS. 12 to 17, another embodiment of the cover and the screen carrier will now be described. Unless described below, the features and functions should be considered to be the same as those described above and like numerals are used to indicate like parts with the addition of 10000.

This embodiment has a magnetic coupling system with at least one magnet (not shown) associated with the screen carrier 13102 and at least one other magnet associated with the cover 15105a. The magnetic coupling system may comprise multiple magnets associated with each of the housing 100 and cover 15105a. Similar to the previously described embodiment, the magnets are attached to upstands or supports 16005 and are received by the apertures 16006 provided by the supports 16005.

The locating features of the housing 100 and the cover 15105a may be interlocking features adapted to form the interlock. In particular, the locating feature of one of the cover 15105a or housing 100 comprises at least one projection 16007 and the locating feature of the other of the cover 15105a or housing 100 comprises at least one recess or aperture 16009, the projection 16007 and recess 16009 forming the interlock. In this embodiment, the cover 15105a has two projections 16007 that are received by complementary recesses 16009 in the screen carrier 13102. In alternative embodiments, the cover 15105a may have one projection that is received by one recess in the screen carrier 13102, or may have three or more projections that are received in three or more complementary recesses in the screen carrier 13102. The recesses and/or projections have rounded or chamfered edges to act as lead in features when assembling the cover 15105a with the housing 100. This allows the cover 15105a to be slightly out of position when the projections first contact the recesses 16009, with the cover 15105a then moving into the correct alignment when the projections fully interlock or couple with the recesses. The recesses 16009 are formed in bosses 16009a, but may alternatively be formed in the planar surface of the screen carrier 13102. In this embodiment, the locating features also comprise the lower surface of the side walls, which is a tapered surface 16009c. The tapered surface 16009c assists with guiding the cover into place due to its interaction with the corresponding tapered surface of the housing.

As mentioned in relation to the earlier described embodiment, the locating features may comprise a back wall and may additionally or alternatively comprise a front wall of the cover, if provided.

Figure 17:
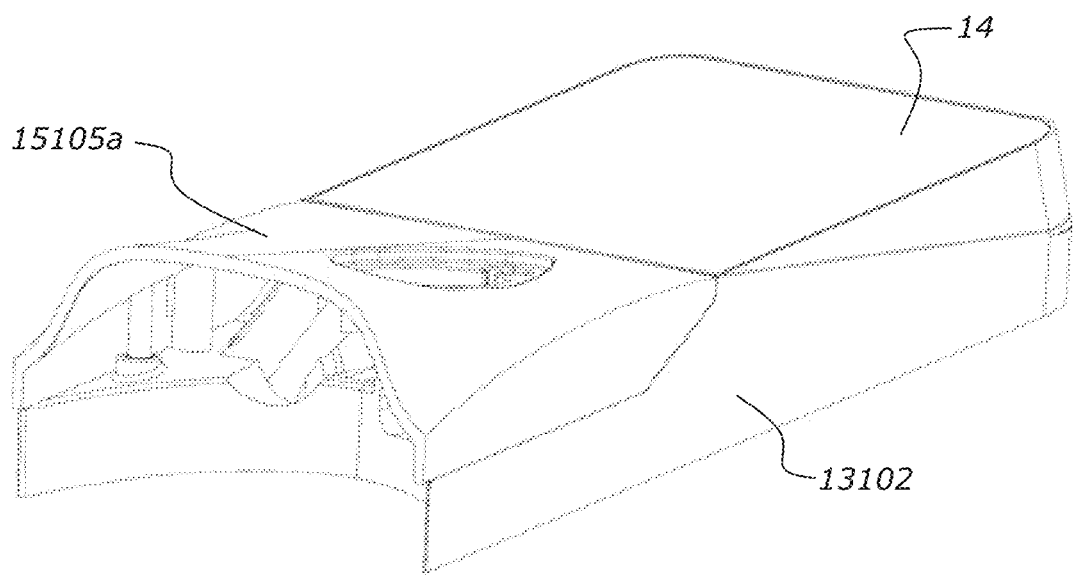
FIG. 17 is another perspective view of the cover of FIG. 12 and the screen carrier of FIG. 14 assembled together.

FIG. 17 shows the cover 15105a and screen carrier 13102 fully assembled with the projections 16007 sitting within the recesses 16009. The projections 16007 prevent, or at least substantially inhibit, movement of the cover 15105a relative to the screen carrier 13102 in any direction other than directly vertically. When assembled with the removable elbow 342, the projections 16007 prevent, or at least substantially inhibit, movement in the horizontal direction that would be required to remove the removable elbow 342. As such, the cover 15105a retains the removable elbow 342 and prevents removal of the removable elbow 342 without first removing the cover 15105a.

Figure 18:
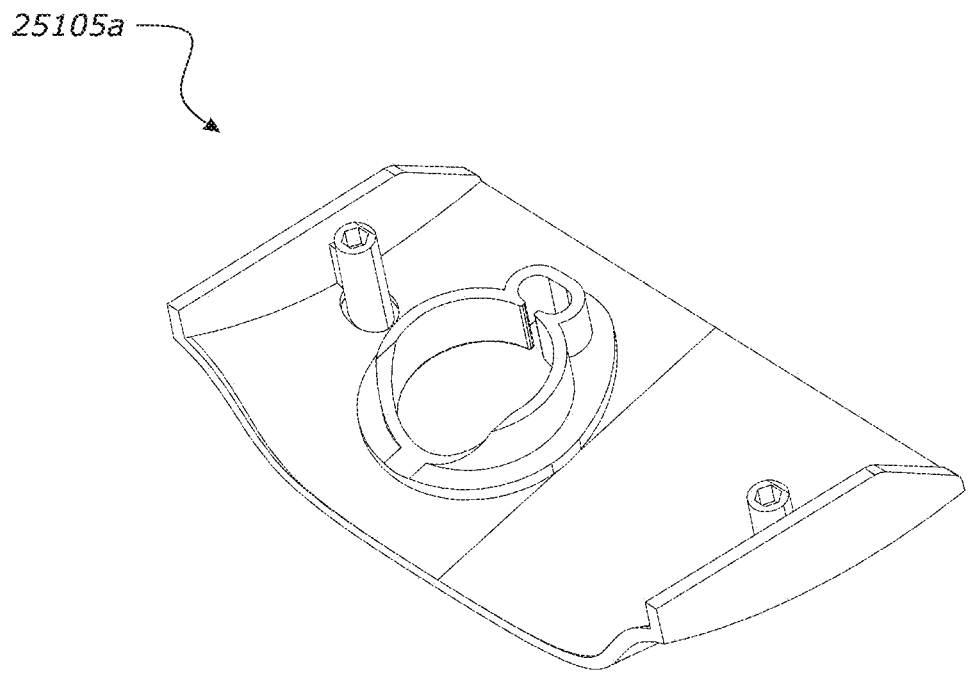
FIG. 18 is a perspective view from below of another embodiment of the cover.
Figure 19:
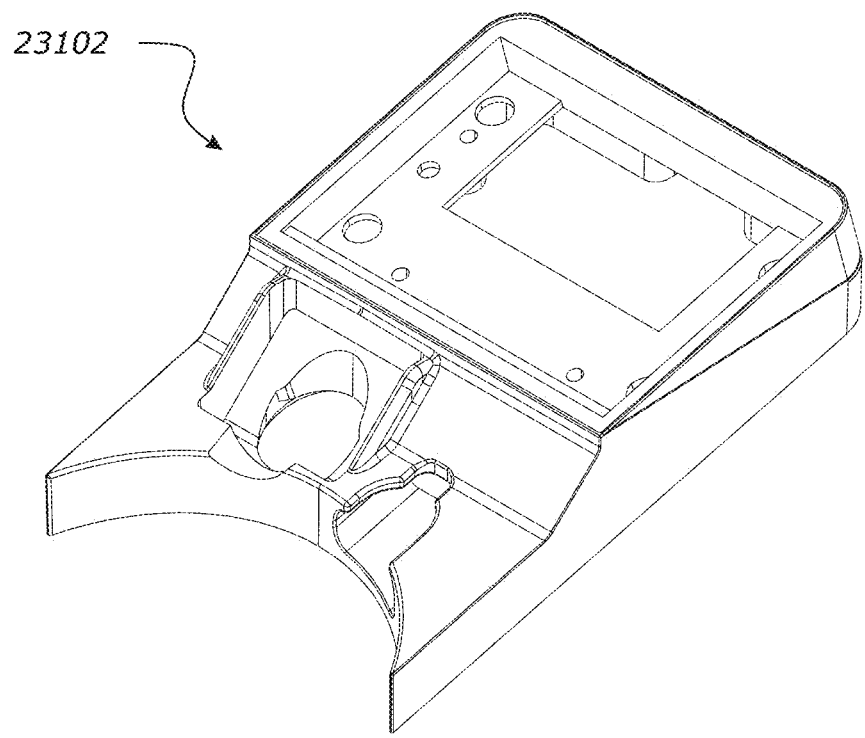
FIG. 19 is a perspective view from above of another embodiment of the screen carrier.
Figure 20:
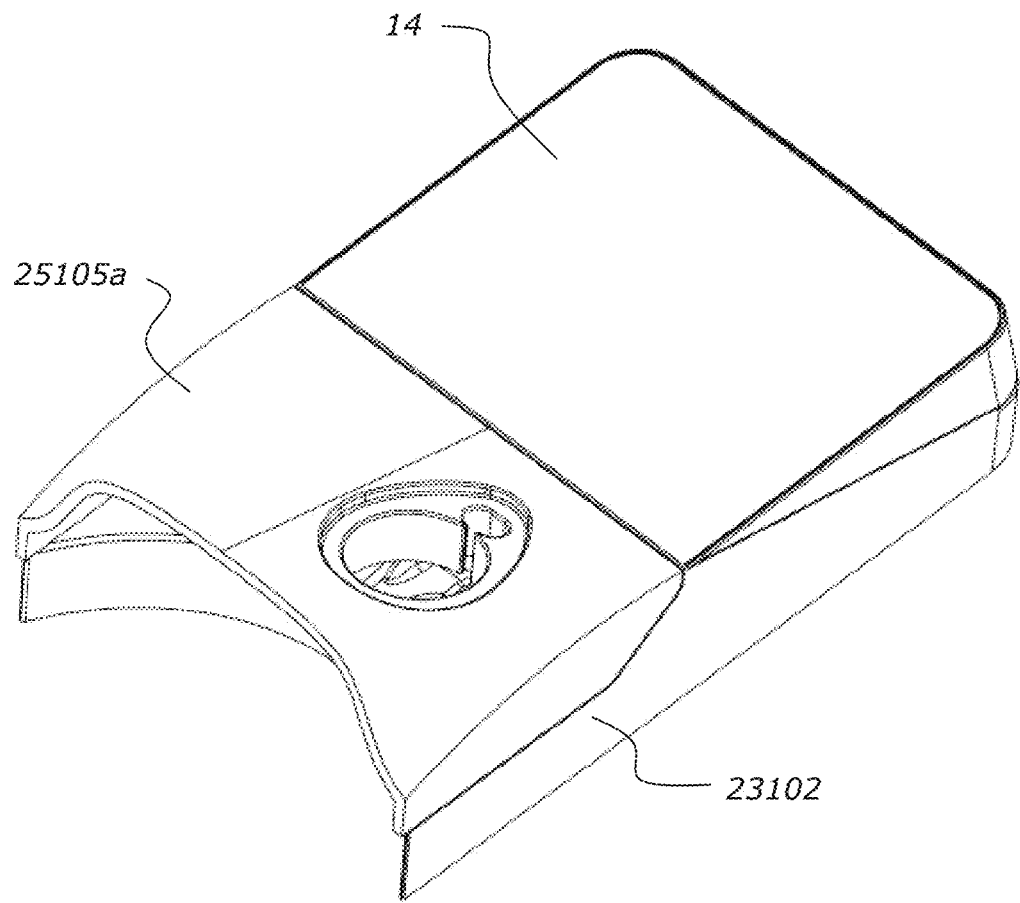
FIG. 20 is a perspective view of the cover of FIG. 18 and the screen carrier of FIG. 19 assembled together.
Figure 21:
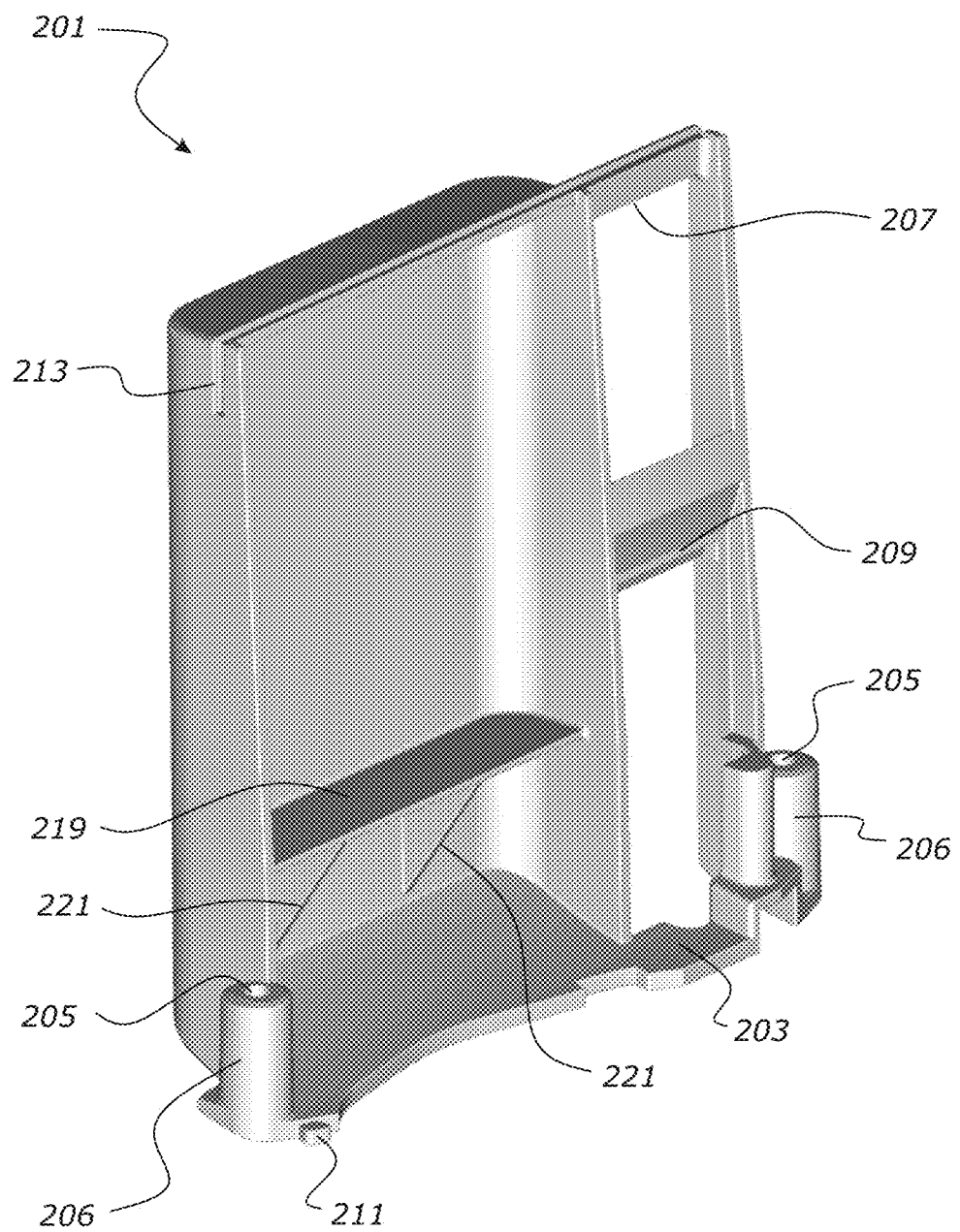
FIG. 21 is a perspective view of a battery cover.
Figure 22:
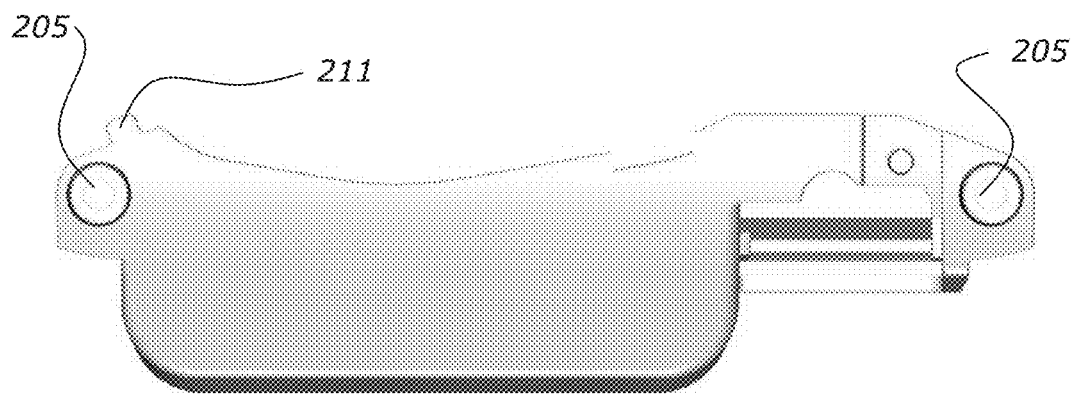
FIG. 22 is a bottom view of the battery cover of FIG. 21.
Figure 23:
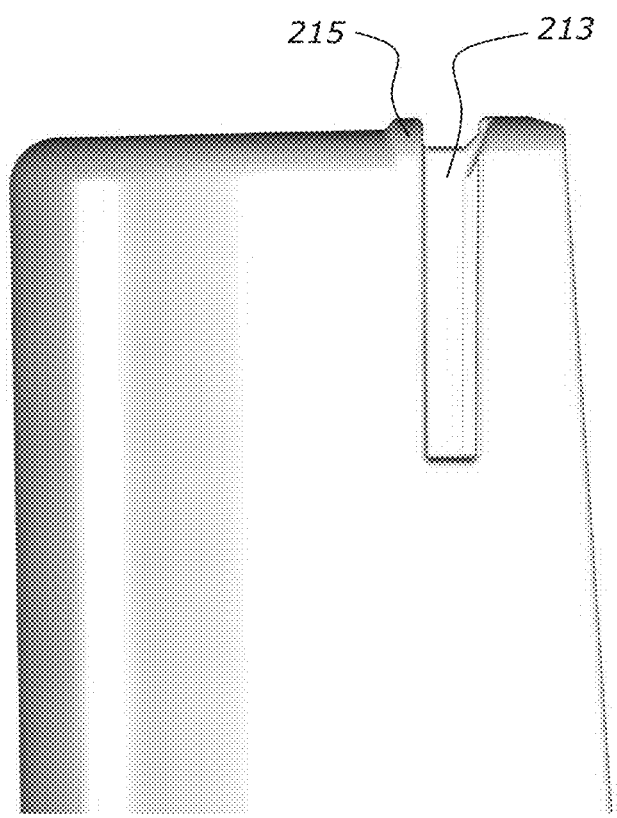
FIG. 23 is a partial side view of the battery cover of FIG. 21.

With reference to FIGS. 18 to 20, another embodiment of the cover and the screen carrier will now be described. Unless described below, the features and functions should be considered to be the same as those described in relation to FIGS. 12 to 17 and like numerals are used to indicate like parts with the addition of 10000.

In this embodiment, the cover 25105a and screen carrier 23102 have a magnetic coupling system. This embodiment does not have projections and recesses that form an interlock.

In this configuration, there is no aperture corresponding to the aperture 6011 of the previously described embodiment. Additionally, this embodiment does not have an angled rear face or a generally flat portion. While this configuration does not provide the interlocking mechanism of other embodiments, the magnetic coupling provides a retaining force that resists horizontal movement of the removable elbow 342, for example when the chamber 300 is removed. Additionally, the coupling between the removable elbow 342 and the housing 100 would also provide a retaining force that resists horizontal movement. One or more of these retaining forces is preferably greater than the force required to remove the chamber 300, such that removing the liquid chamber 300 would not pull the removable elbow 342 out of place.

In addition, the locating features may comprise a back wall and may additionally or alternatively comprise a front wall of the cover 25105a, if provided.

FIG. 20 illustrates this embodiment of the cover assembled with the screen carrier 13102.

Another feature shown in FIG. 20 is an alternative form of the screen carrier 13102. In the previously described embodiment, the screen was recessed such that no part of the screen was higher than the other components of the apparatus. In this configuration, the screen is raised such that the lower end of the screen is level with the upper surface of the screen carrier 13102, with the rest of the screen angled to extend above the other components of the apparatus. This prevents, or at least substantially inhibits, the screen from being visually obstructed by the other components of the apparatus, and allows for a user to more easily view the user interface 14 from a distance.

With reference to FIGS. 21 to 26, the apparatus 10 may have a battery (not shown) in a battery cover 201 that is coupled to the exterior back wall of the apparatus 10. The battery cover 201 has a flange 203 that overlaps the motor and/or sensor module to prevent the motor and/or sensor module from being removed before the battery is removed. The battery cover 201 may have one or more apertures 205 formed in upstands 206 on the flange 203. Fasteners could be inserted through the apertures 205 to fasten the flange 203 to the lower chassis of the apparatus 10.

The battery cover 201 may be removable in order to allow access to the battery. However, in another embodiment, the battery cover 201 may not be easily removable, but instead require disassembly of various fasteners (as described above). This would prevent the battery from being removed by a regular user, as removal of the battery cover would typically be for replacing the battery, which would only be done every couple of years by a technician. Additionally, certain electronic components may be exposed when the battery and battery cover are removed, and as such the fasteners are useful in preventing unwanted disassembly.

The battery cover 201 may have an upper horizontal edge 207 that acts as a liquid deflector for preventing water from dripping onto various electrical connections. A similar feature 209 could be incorporated below the first feature for a secondary electrical connection, such as a connector for a battery charger.

The apparatus 10 also has a valve retention tab 211 that overlaps the valve module that prevents removal of the valve module when assembled.

The cover 201 may be provided with a groove 213 and/or at least one ridge 215 around its upper edge. This groove 213 can extend down at least a portion of the side of the cover 201. The groove 213 and/or ridge could interact with a complementary shaped ridge 217 and/or groove on the housing 100 of the apparatus 10. When assembled, the interaction between the two complementary features provides a tortuous path to prevent the ingress of liquid and oxygen into the electrical components.

The battery cover may include a ledge 219 for supporting the battery at the correct height and prevent the battery from moving around during use. The ledge could be supported by one or more structural ribs 221.

The battery cover 201 could be constructed with a portion 223 that extends below the base level of the apparatus 10. This allows for a larger battery to be used, which would improve battery life and/or maximum power output. Because the extended portion may interfere with allowing the apparatus 10 to be supported on a flat surface, this configuration would likely be used when the apparatus 10 is intended to be connected to a moveable stand via a mounting feature on the side of the apparatus 10. The apparatus 10 may be mounted to a moveable stand when the apparatus 10 is required to frequently move around with the patient, and as such a larger and more powerful battery would be increasingly useful.

Figure 24:
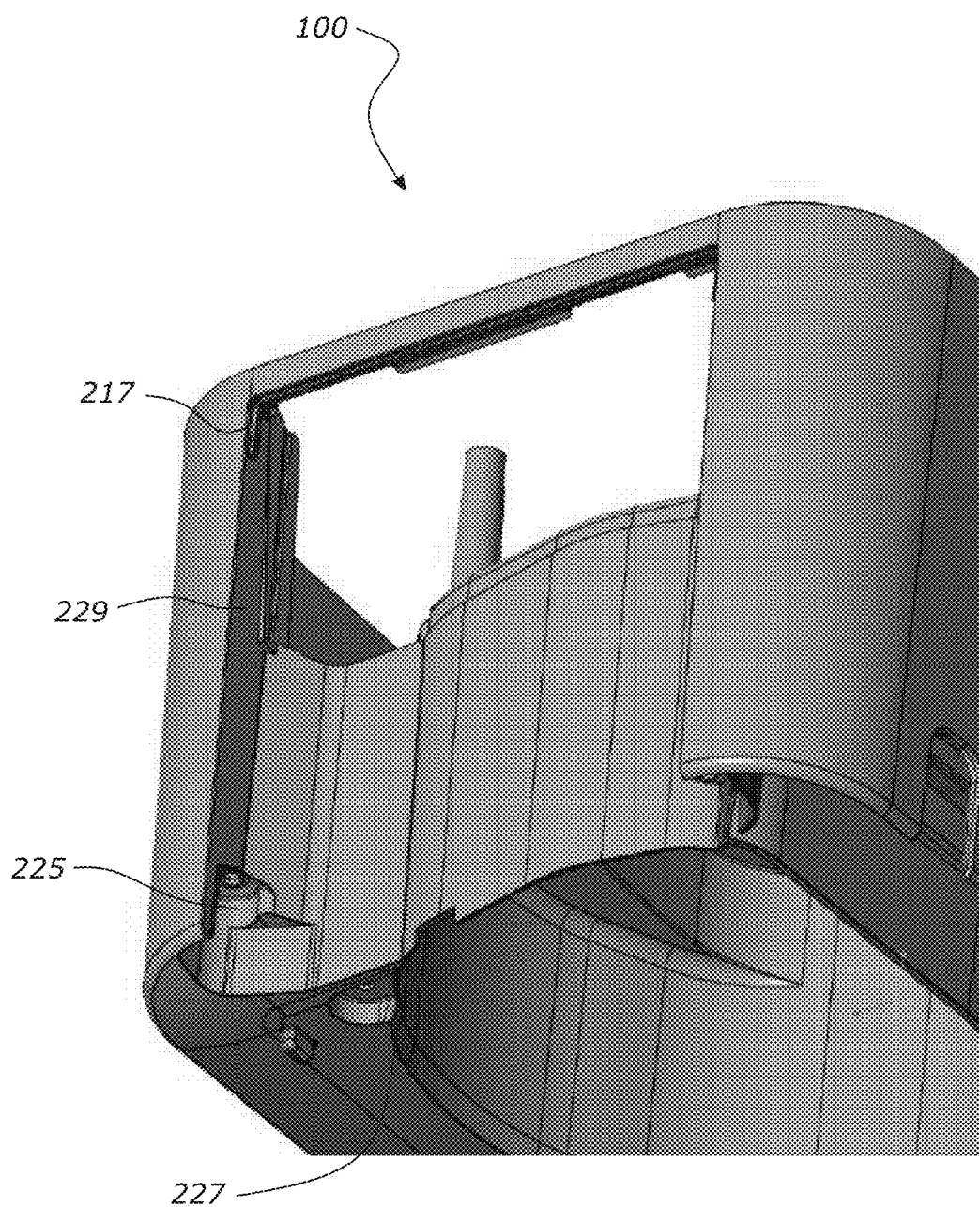
FIG. 24 is a perspective view from below of a housing.
Figure 25:
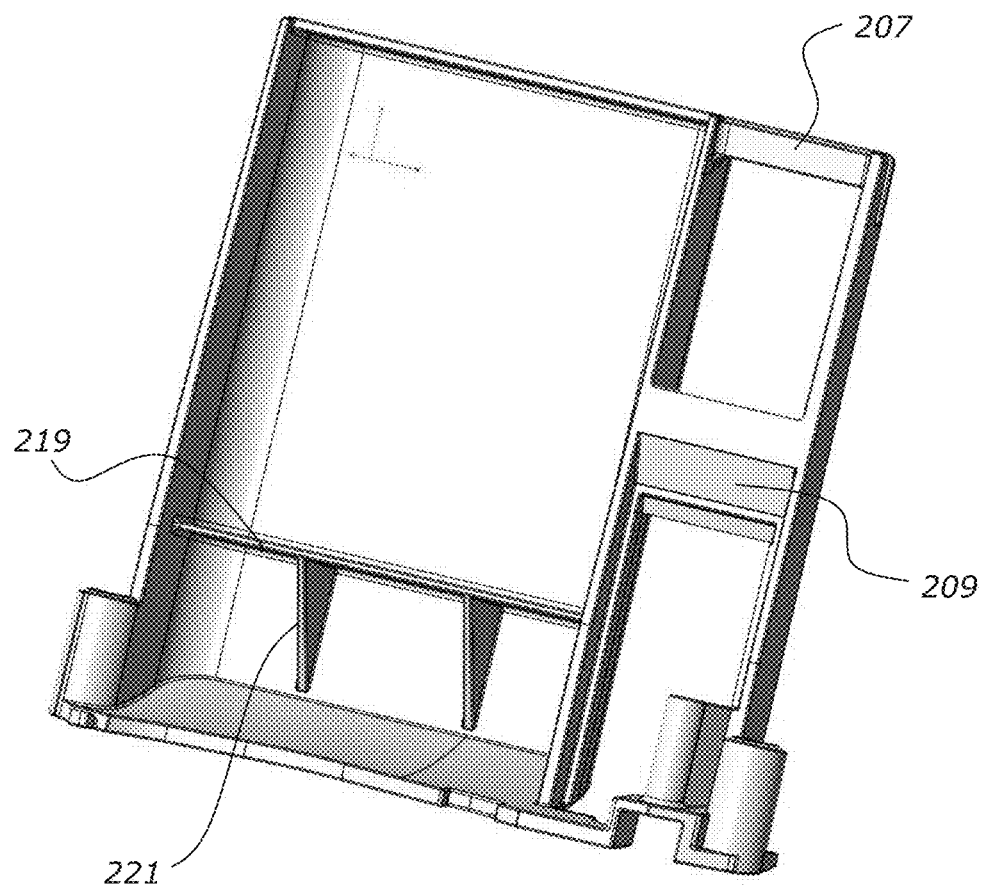
FIG. 25 is another perspective view of the battery cover.
Figure 26:
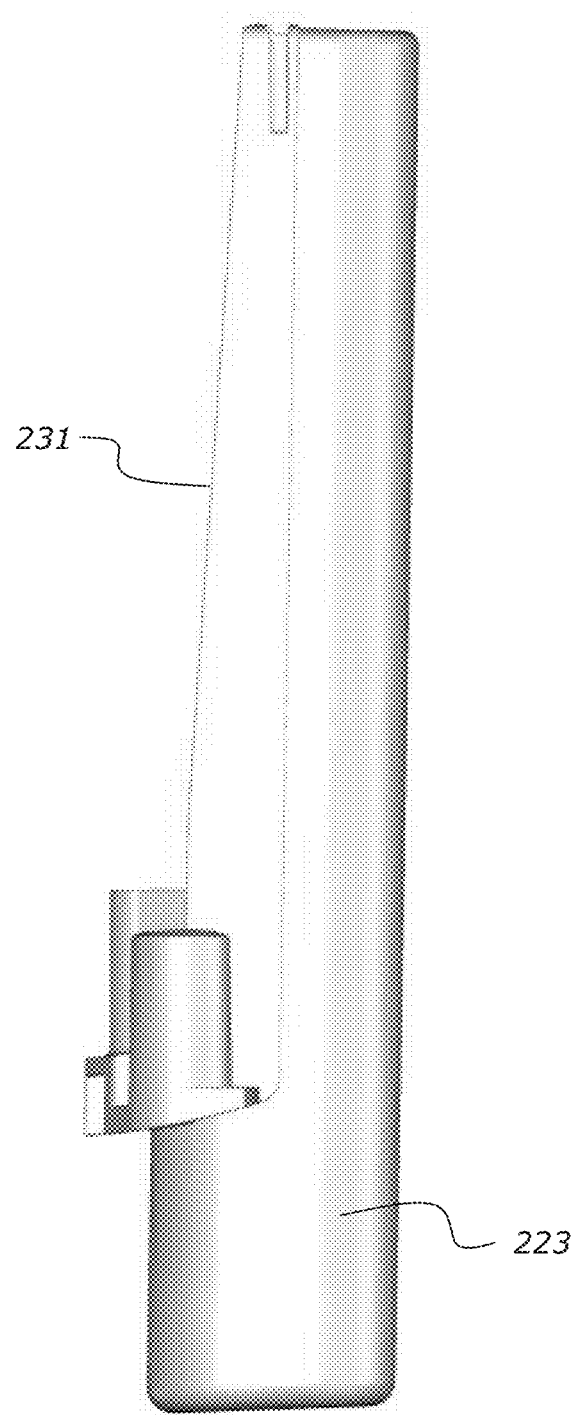
FIG. 26 is a side view of the battery cover of FIG. 21.
Figure 27:
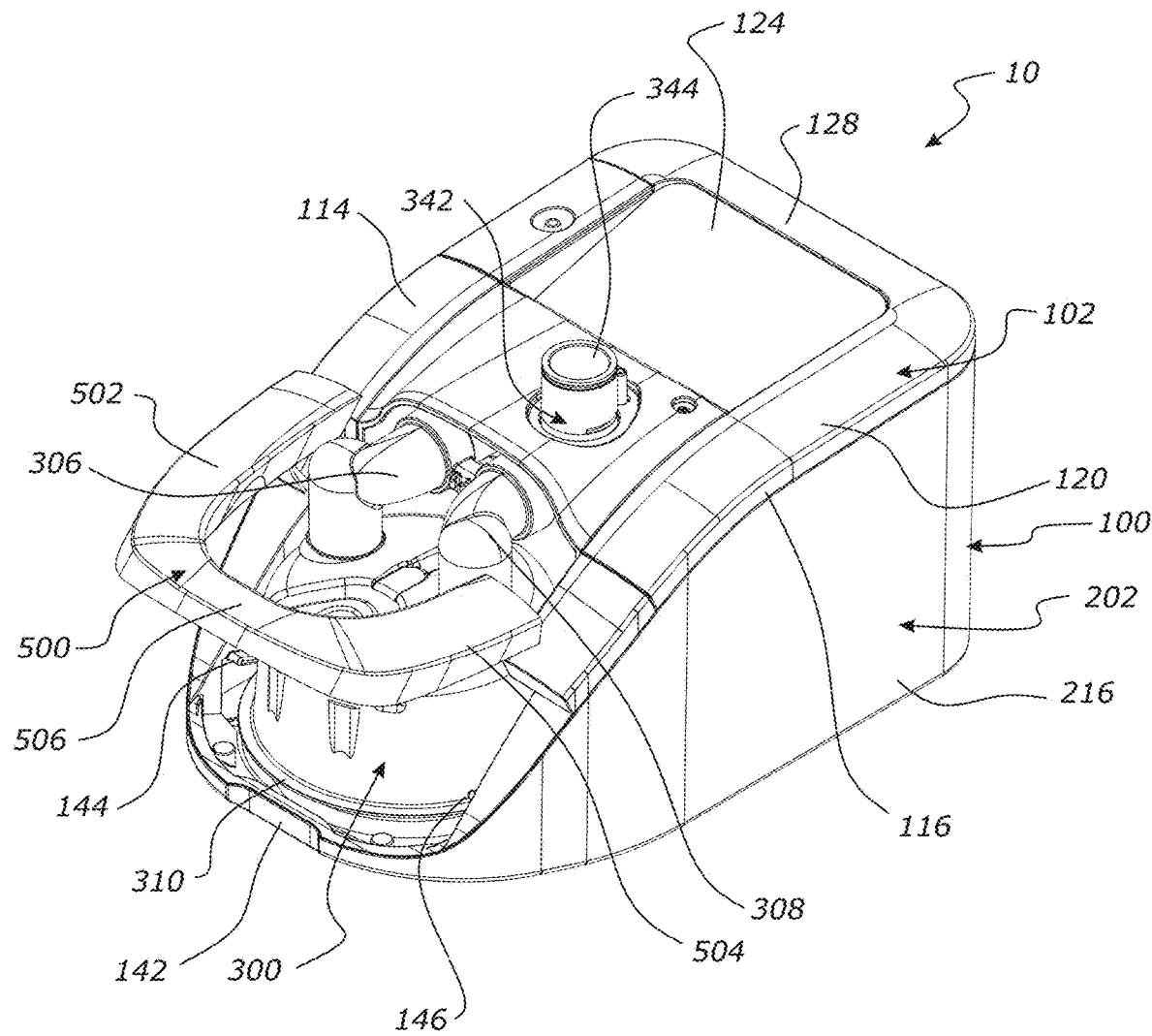
FIG. 27 is a view corresponding to FIG. 2, but with the handle/lever in a partly raised position.
Figure 28:
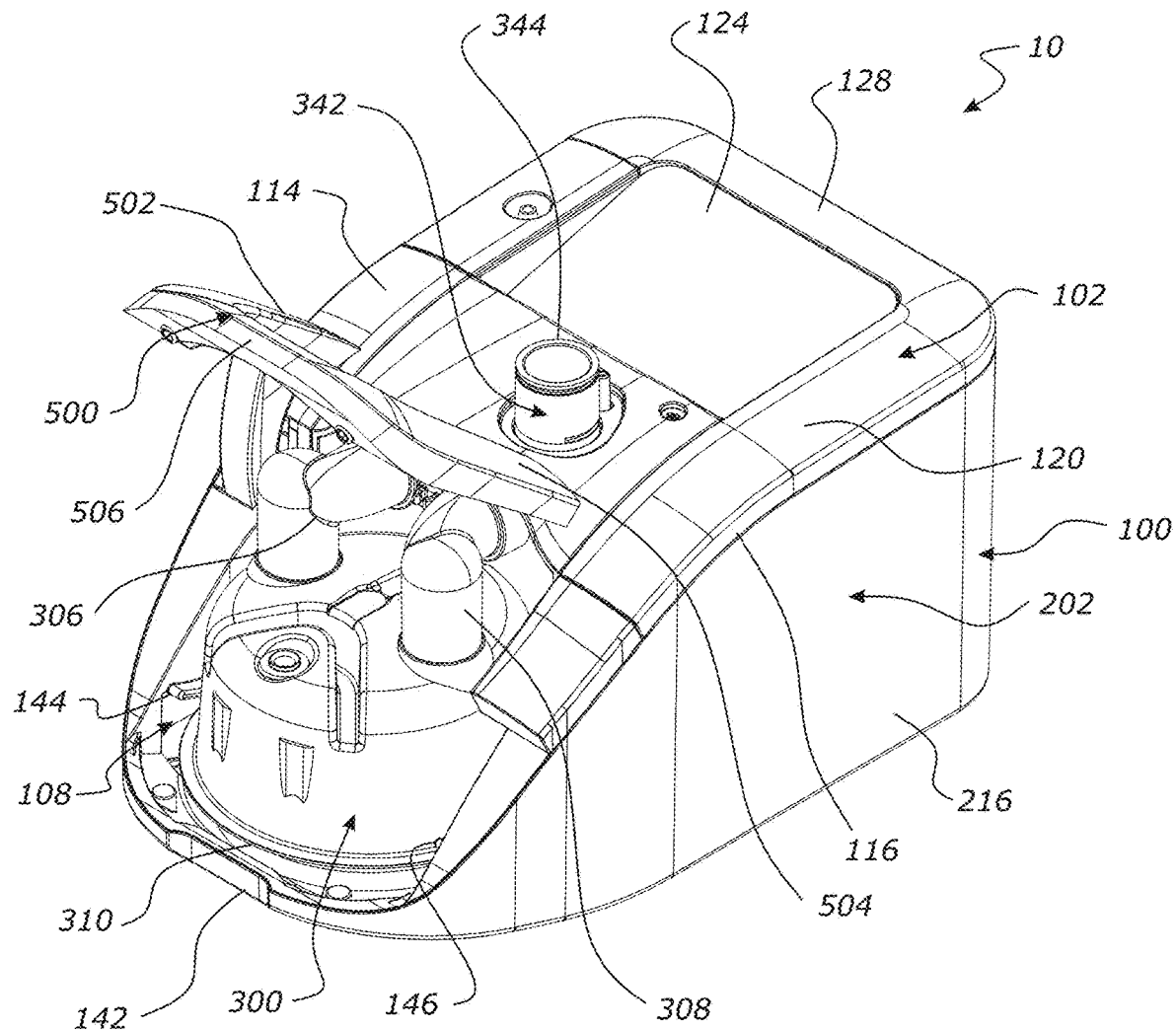
FIG. 28 is a view corresponding to FIG. 27, but with the handle/lever in a more raised position.

FIG. 24 shows the corresponding section of the apparatus 10 that the battery cover 201 couples with. The housing 100 has a complementary ridge and/or groove that interacts with the groove and/or ridge on the cover. When assembled, the interaction between the two complementary features provides a tortuous path to prevent the ingress of liquid and oxygen into the electrical components.

The housing 100 has complementary apertures 225 that surround the apertures on the battery cover to allow a fastener to be inserted through both apertures and couple the housing 100 with the battery cover. The coupling of the apertures additionally acts as a locating feature to ensure the cover is in the correct position relative to the housing 100 prior to the fastener being added. The fastener being used instead of some form of mechanical clip increases the difficulty of removing the battery cover and helps to prevent unwanted disassembly of the device.

The apparatus has a small gap 227 at the base of the housing 100 wall to allow for the tab on the battery cover to overlap the motor/sensor module.

The apparatus housing 100 may have angle features 229 on the inner surface of the wall that allow for initial receipt of the battery cover in a variable position, but then guide the battery cover into the correct position as the cover is further inserted into its final position. This could match up with a similar angled feature 231 on the cover.

Humidifier/Liquid Chamber Bay and Handle Arrangement

The liquid chamber bay 108 and handle arrangement will now be described in more detail with reference to FIGS. 2, and 27 to 48.

As discussed, the liquid chamber bay 108 comprises opposed left side and right side guide rails 144, 146 which extend toward a centre of the bay 108 from the respective left and right side inner walls 112, 118. The guide rails 144, 146 assist with guiding the liquid chamber 300 into position in the bay 108. The guide rails 144, 146 are parallel to the floor 136 of the liquid chamber 300 and/or with the upper surface of the heater plate 140, to enable the flange 310 of the liquid chamber 300 to slide therebetween.

The handle arrangement has a handle 500 for assisting with insertion and/or retention and/or removal of the liquid chamber 300 in and/or from the chamber bay 108. Different configurations may be configured for assisting with one, two, or all of insertion, retention, removal of the liquid chamber 300 in and/or from the liquid chamber bay 108. The handle is movable from a first position to a second position. In the form shown, the first position is a fully lowered or closed position (e.g. FIG. 2) and the second position is a fully raised position (e.g. FIG. 29).

The handle 500 is a single sided configuration. That is, only one side of the handle 500 is movably connected relative to the main housing 100 of the flow therapy apparatus 10, whereas there is no pivot connection of the other side of the handle 500 to the main housing. In the form shown, the left side of the handle 500 is pivotally connected relative to the main housing 100. However, in an alternative configuration, only the right side may be pivotally connected to the main housing 100. The handle 500 is pivotally and translationally connected to the main housing, so that the handle moves on a path having a varying radius relative to the main housing.

The handle 500 has a left side arm 502 that is pivotally and translationally attached relative to the left inner side wall 112 of the upper chassis 102. The left side arm 502 is configured to be substantially flush with the interconnecting wall 114 when the handle 500 is in the lowered or closed position of FIGS. 2, 31, 35, 39, 43, and 48. Rather than a right side arm, the handle 500 further comprises a right side member 504 that is shorter than the left side arm 502, and that is not pivotally attached to the right inner side wall 118 of the upper chassis 102. The right side member 504 is configured to be substantially flush with the interconnecting wall 120 when the handle 500 is in the lowered or closed position. The main housing is provided with recesses to enable the left side arm 502 and right side member 504 to be substantially flush with the interconnecting walls. In the form shown, the left side member 502 is longer than the right side member 504, so a spacer member 120" is mounted to the upper chassis 102 and sits substantially flush with the interconnecting wall 120 and the right side member 504 when the handle 500 is in the lowered or closed position. The spacer member 120" may carry a label or other indicia with information representing the device and/or its user. The left side arm 502 will not be substantially flush with the interconnecting wall 114 and the right side member 504 will not be substantially flush with the spacer member 120" when the handle is not fully closed/lowered, thereby providing a visual cue that the handle 500 is not fully closed/lowered.

A terminal part of the handle has a cross-member handle portion 506 that interconnects the forward ends of the left side arm 502 and the right side member 504 and forms an engagement region for grasping by a user's fingers. When the handle 500 is in the raised position as shown in FIGS. 29, 34, 38, and 42 for example, the cross-member 506 can act as a carrying handle for the user to lift and carry the apparatus 10. The liquid chamber 300—shown in FIG. 30 for example—can be inserted into or removed from the liquid chamber bay 108 when the handle 500 is raised. When the handle 500 is in the lowered position, it inhibits or prevents removal of the liquid chamber 300 from the liquid chamber bay 108.

Rather than having the right side member 504, the handle 500 may terminate at the right side of the cross-member 506. However, having the rearwardly directed member 504 is preferred, as it reduces the likelihood of the apparatus 10 being dropped while it is being carried.

In the closed or fully lowered position of the handle 500, the cross-member 506 is located at the front of the main housing and encloses a portion of the liquid chamber bay 108. The handle 500 and/or housing 100 may have a positive engagement feature to positively engage the handle/500 in the lowered or closed position. For example, the cross-member 506 of the handle 500 may have a recess or protrusion, and the housing may have a complementary protrusion or recess which is engaged with the recess or protrusion of the handle 500 when the handle is in the lowered position. With the handle 500 in the lowered or closed position, a portion of the cross-member 506 projects sufficiently above the floor of the liquid chamber bay 108 and above the flange 310 of the liquid chamber 300 that it prevents the liquid chamber 300 from being slid forward and removed from the liquid chamber bay 108. The liquid chamber bay 108 comprises guide rails 144, 146 to prevent the liquid chamber 300 from being lifted and removed vertically from the liquid chamber bay 108 when the handle 500 is in the lowered or closed position.

Figure 45:
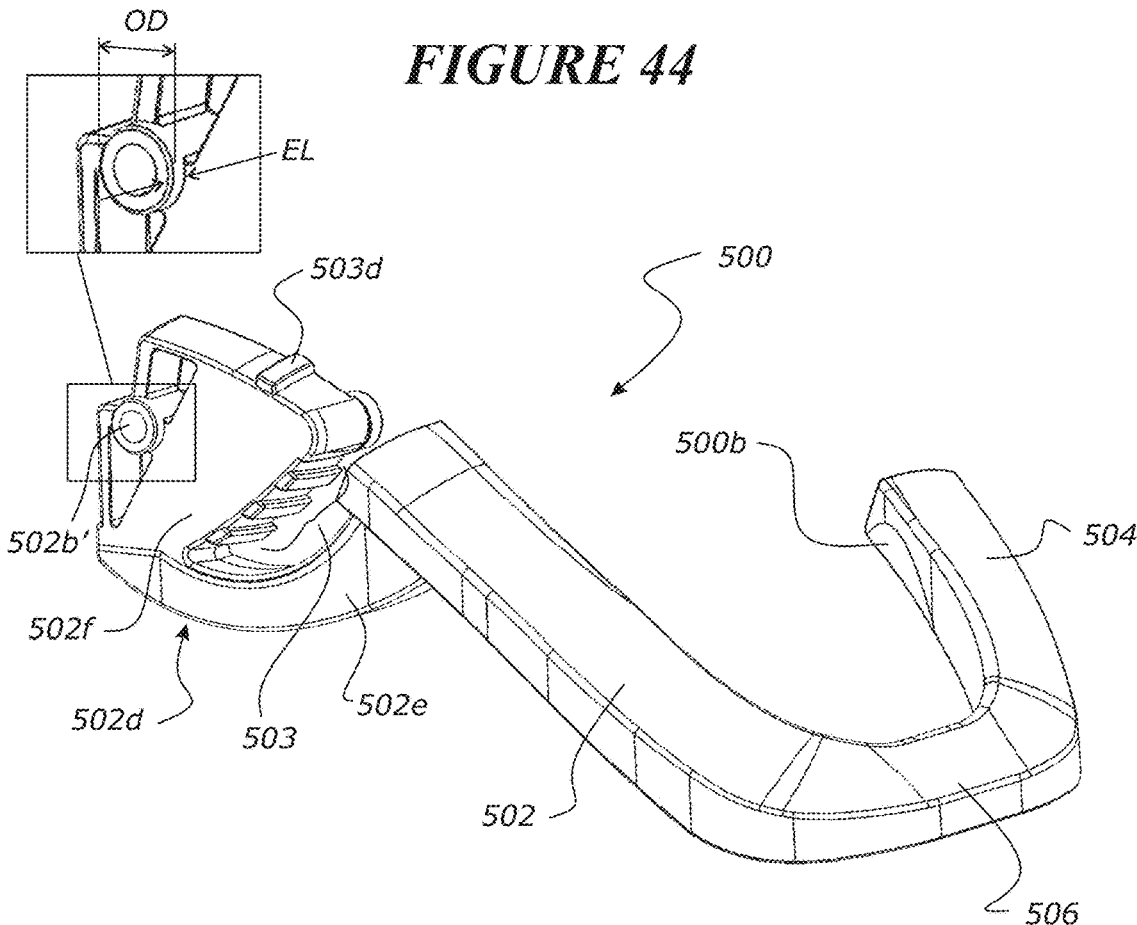
FIG. 45 is a front left side perspective view of the handle/lever.
Figure 46:
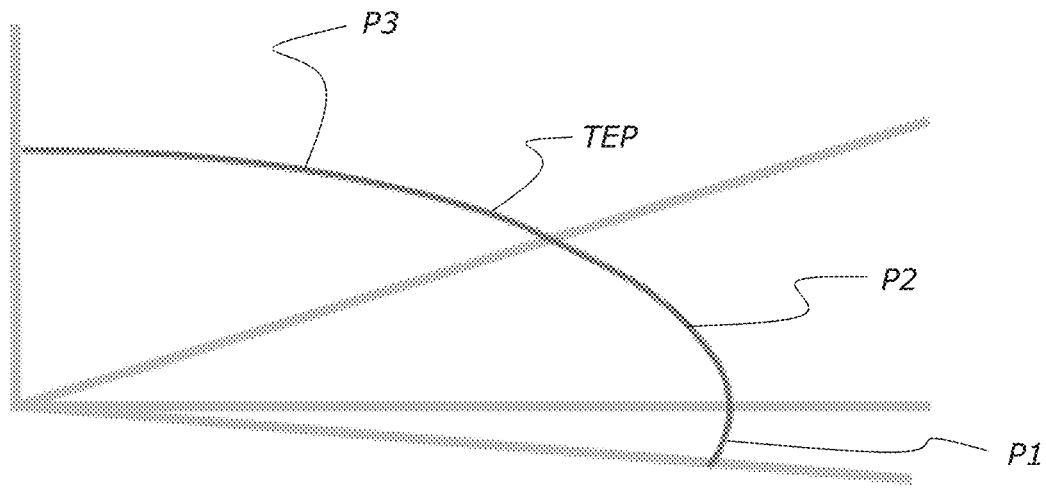
FIG. 46 is a plot showing the movement path of a terminal end of the handle/lever of the apparatus.
Figure 47:
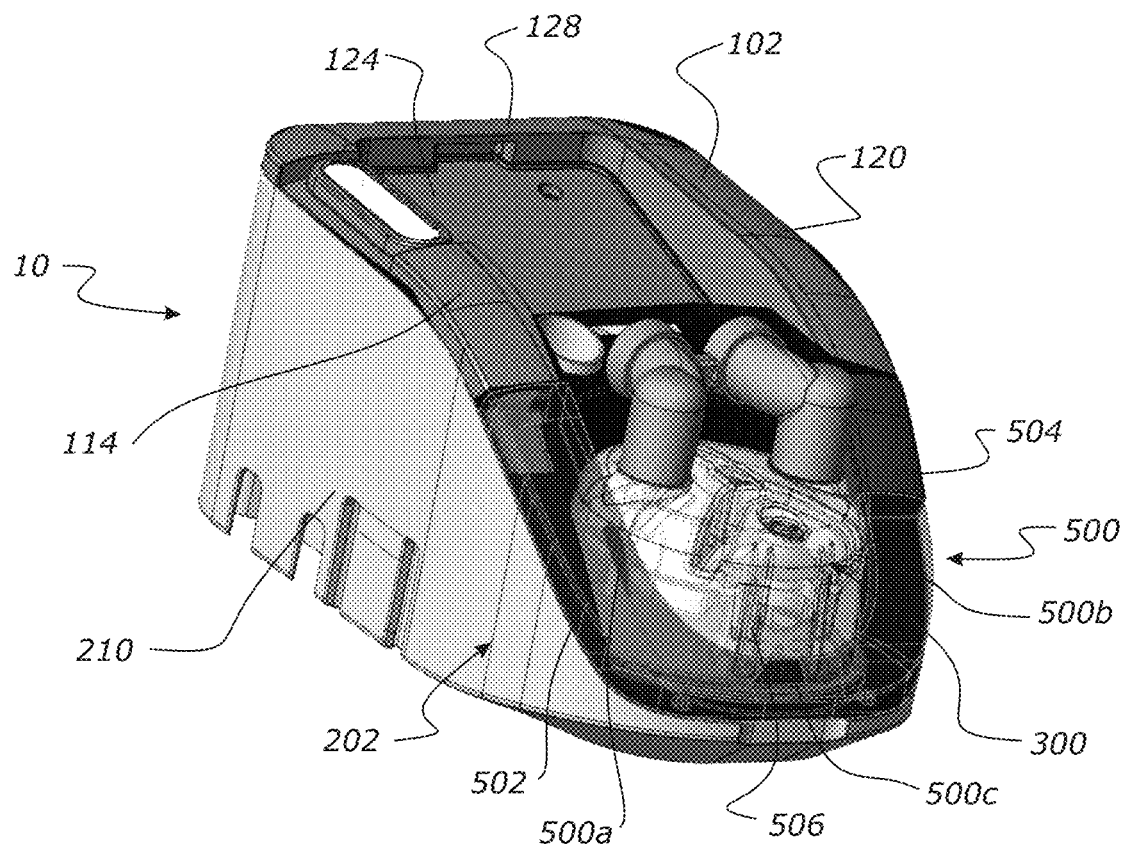
FIG. 47 is a front left side overhead perspective view showing engagement points between the lowered handle/lever and the liquid chamber.

When the liquid chamber 300 is positioned in the liquid chamber bay 108 and the handle 500 is in the lowered or closed position, engagement features 500a, 500b, 500c on the handle 500 engage with the liquid chamber 300 to assist with maintaining the sealing engagement between the ports. Referring to FIGS. 45, 46, and 48, the engagement features comprise a first engagement feature 500a in the form of a scalloped recess on the lower inner side of the left side arm 502, a second engagement feature 500b in the form of a scalloped recess on the lower inner side of the right side member 504, and a third engagement feature 500c in the form of a scalloped recess on the lower inner side of the cross-member 506. The scalloped regions 500a, 500b, 500c engage against upper edges of the liquid clamber 300. The scalloped recesses may also assist with inserting the liquid chamber 300 into the liquid chamber bay 108 by contacting the upper edges of the liquid chamber housing and pushing the upper portion of the liquid chamber further into the liquid chamber bay 108 as the handle 500 is lowered.

While three engagement features 500a, 500b, 500c are shown, fewer or more engagement features could be used. For example, only the front engagement feature 500c may be provided, or alternatively, only the side engagement features 500a, 500b may be provided. The scalloped recesses enable the handle 500 to apply force against the liquid chamber 300 when the handle 500 is in the lowered position, while enabling a close fit of the handle 500 around the liquid chamber 300 which reduces the likelihood of items inadvertently being dropped into the liquid chamber bay 108. In other configurations, engagement features may not be provided on the handle 500. Instead of being scalloped recesses, the engagement features 500a, 500b, 500c could have a different form. For example, one or more of the engagement features could comprise a protrusion that extends from part of the handle 500.

It can be seen from FIG. 2 that a substantial part of the liquid chamber 300 is exposed and visible from the front and top of the apparatus when the handle 500 is in the lowered position. The liquid chamber 300 will typically be transparent, and by having a substantial part of the liquid chamber 300 exposed and visible, a user will readily be able to see the liquid level in the liquid chamber without needing to raise the handle 500 from the lowered position.

The guide rails 144, 146 may have a curved shape and/or upwardly angled leading portions 144a (FIG. 3) to assist with easing the liquid chamber 300 into the liquid chamber bay 108. Alternatively, or additionally, the guide rails 144, 146 may be oriented to be non-parallel with a base of the chamber bay 108, and thereby with the heater plate.

FIGS. 30 to 46 show details of the pivot arrangement of the handle 500. A rearward portion of the left side arm 502 is connected to a pivot arm 502d. The pivot arm 502d comprises a forward arcuate portion 502e that extends downwardly and rearwardly from the left side arm 502 when the handle 500 is in the lowered or closed position. A rearward part of that forward arcuate portion 502e is connected to a body portion 502f that extends upwardly and forwardly therefrom when the handle is in the lowered or closed position. The body portion 502*f* has a tapered configuration with a base of the body portion being relatively small and an upper terminal portion of the body portion being relatively large. The body portion 502*f* is relatively large so as to provide additional mass to help stabilise the handle in the raised position and reduce side-to-side movement of the handle in that position.

A spacing is provided between the majority of the pivot arm 502*d* and the body portion 502*f*. An upper end of the body portion 502*f* comprises two pivot protrusions, a rear, outwardly directed, first pivot protrusion 502*b*' and a forward, inwardly directed, second pivot protrusion 502*b*". Each pivot protrusion 502*b*', 502*b*" extends from the body portion 502*f* and has an exposed axial length EL and a transverse dimension OD. The transverse dimension OD is greater than the axial length. For example, the transverse dimension OD may be at least twice the axial length EL, and may be three times or greater. An example transverse dimension OD is about 12 mm, but any other suitable transverse dimension could be used. The pivot protrusions are shown as being substantially cylindrical, but could alternatively be a different shape.

Figure 35:
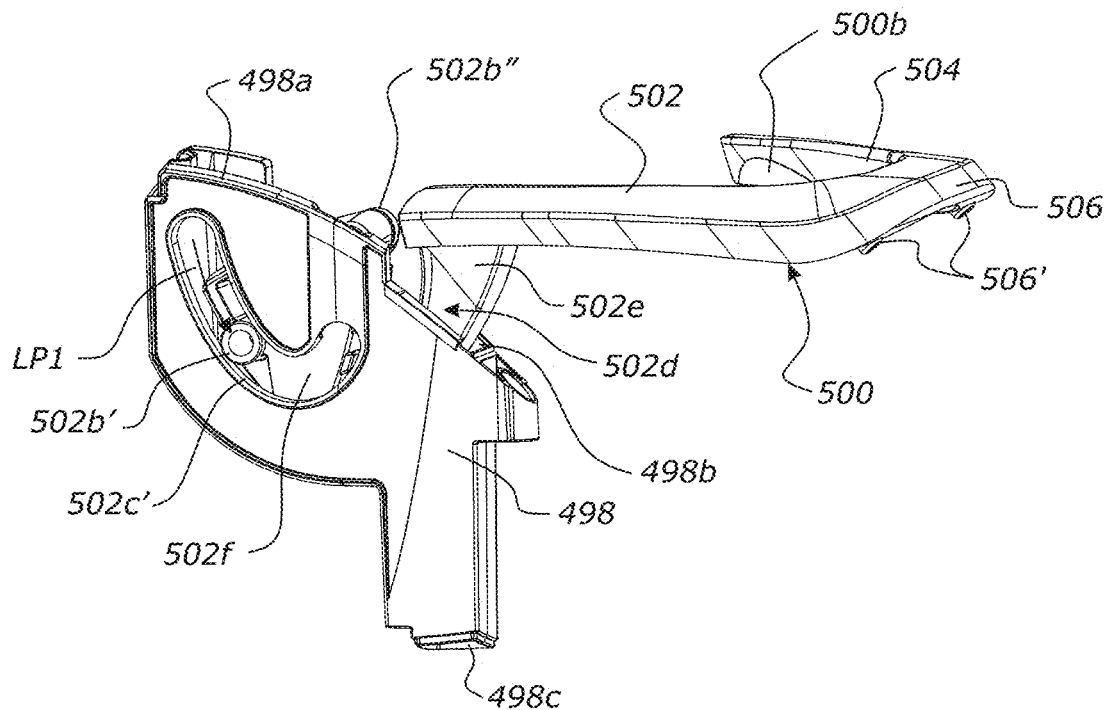
FIG. 35 is a view corresponding to FIG. 34 but with the handle/lever in the partly raised position corresponding to FIG. 27.
Figure 36:
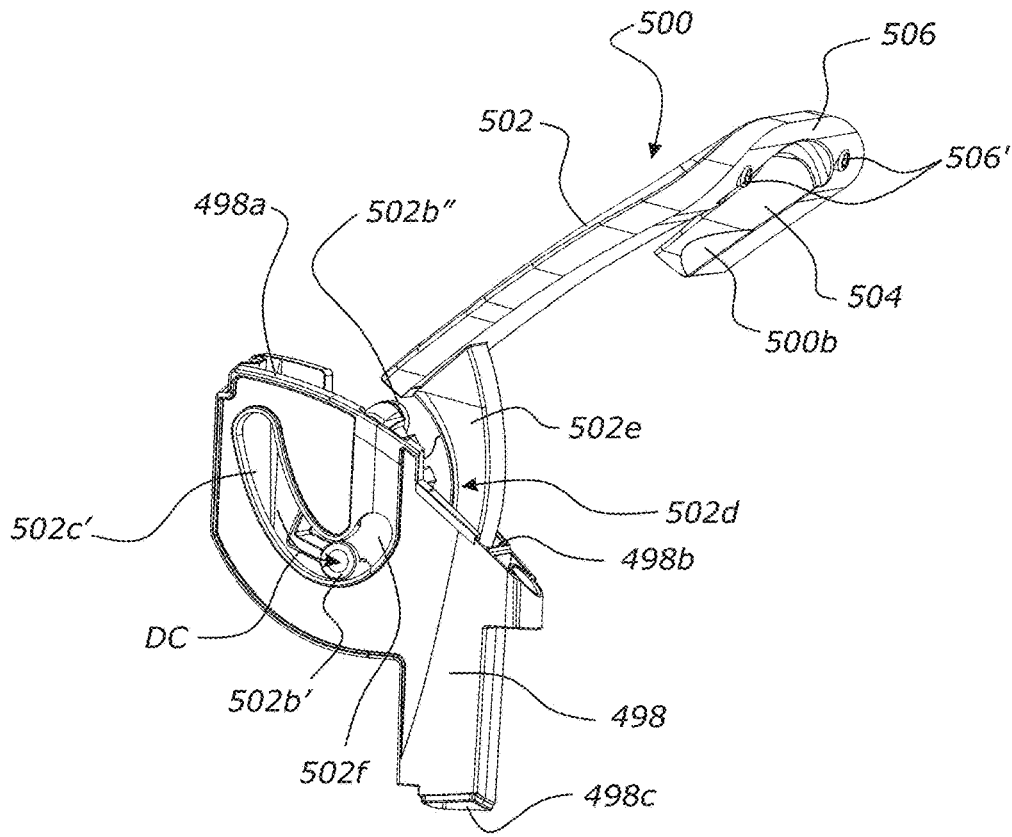
FIG. 36 is a view corresponding to FIG. 34 but with the handle/lever in the more raised position corresponding to FIG. 28.
Figure 37:
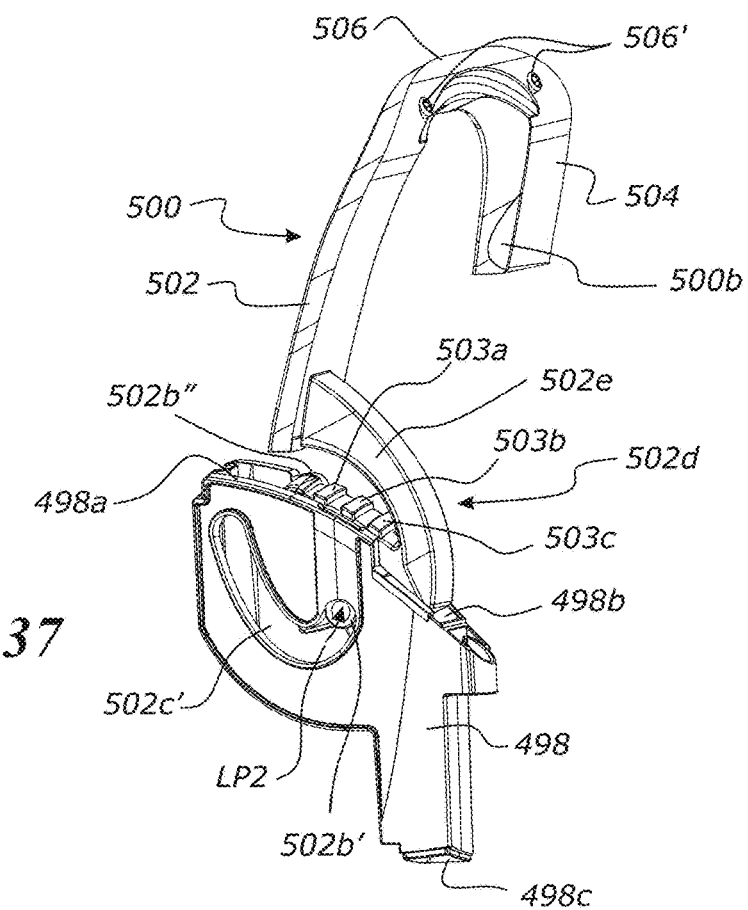
FIG. 37 is a view corresponding to FIG. 34 but with the handle/lever in the fully raised position corresponding to FIG. 29.

The rear pivot protrusion 502*b*' is received in a first pivot cavity 502*c*' which is shown in FIGS. 34 to 37. The first pivot cavity 502*c*' comprises a slot or a channel with closed ends. The first pivot cavity 502*c*' is a general J-shaped. A rearward portion of the first pivot cavity 502*c*' which corresponds to the position of the rear pivot protrusion 502*c*' when the handle is in the lowered position or is initially raised, has a downwardly and forwardly extending orientation, and is either substantially linear or has a relatively large radius of curvature. An intermediate portion of the first pivot cavity 502*c*' undergoes a direction change and has a relatively small radius of curvature. The forward portion of the first pivot cavity is upwardly and forwardly directed, is shorter than the rear portion, and is either substantially linear or has a relatively large radius of curvature. As shown in FIGS. 34 to 37, as the handle 500 is raised from the lowered position, the rear pivot protrusion 502*b*' initially follows a downward and forward substantially linear path LP1 (FIGS. 34 and 35), undergoes the direction change DC (FIG. 36), and then follows a shorter upward and forward linear path LP2 (FIG. 37). The rear pivot protrusion 502*b*' is configured to be retained in the first pivot cavity 502*c*', but to substantially freely move along the length of that pivot cavity. The ends of the first pivot cavity 502*c*' are closed so that the pivot protrusion 502*b*' cannot exit either end of the pivot cavity.

Figure 38:
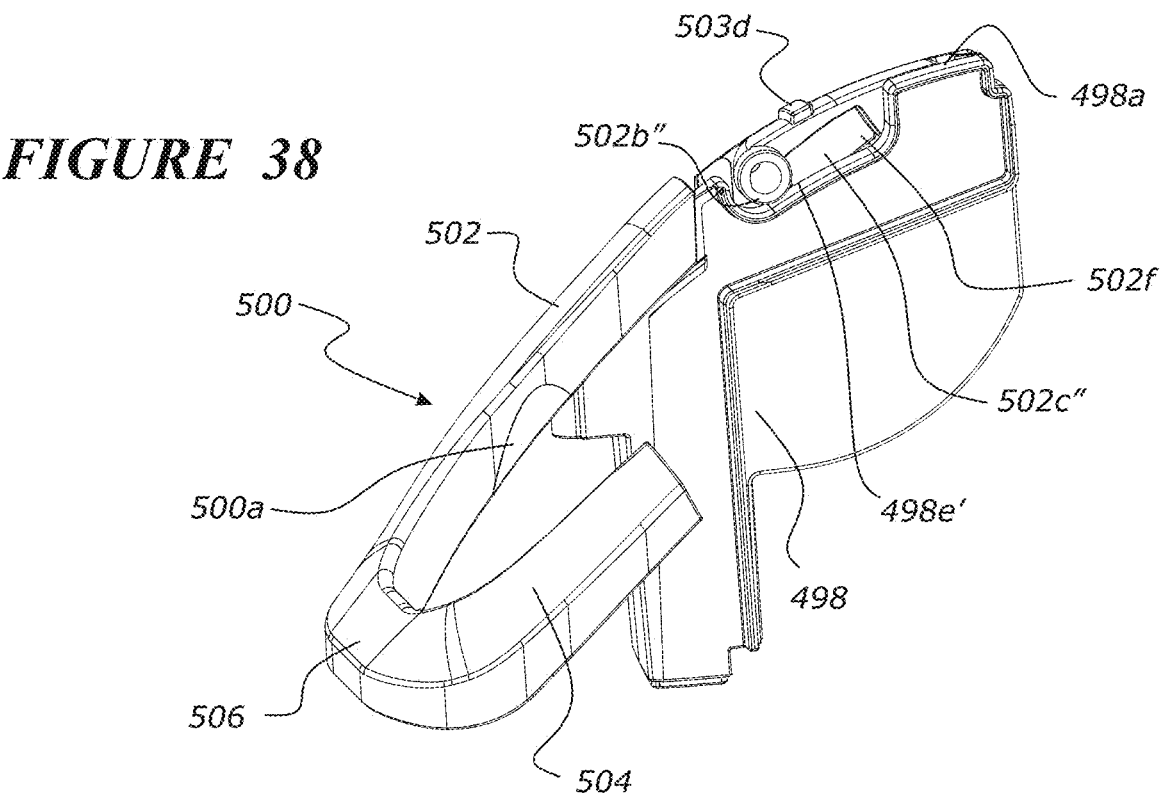
FIG. 38 is a front right perspective view of the handle retainer and the handle/lever in the lowered position corresponding to FIG. 2.
Figure 39:
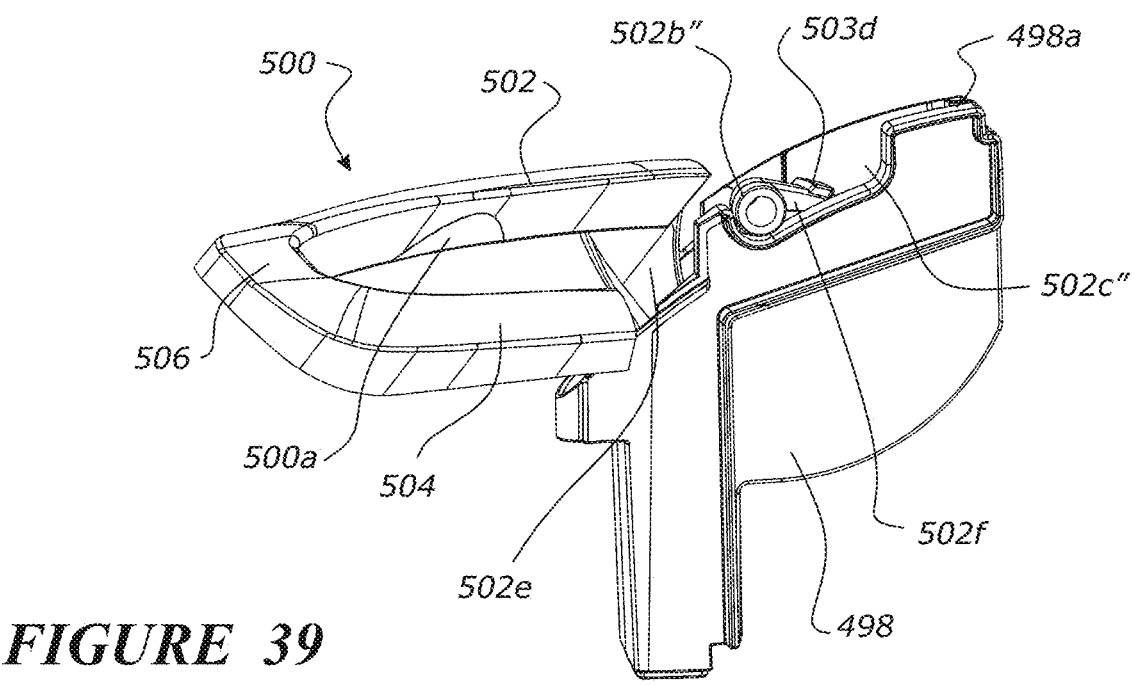
FIG. 39 is a view corresponding to FIG. 34 but with the handle/lever in the partly raised position corresponding to FIG. 27.
Figure 40:
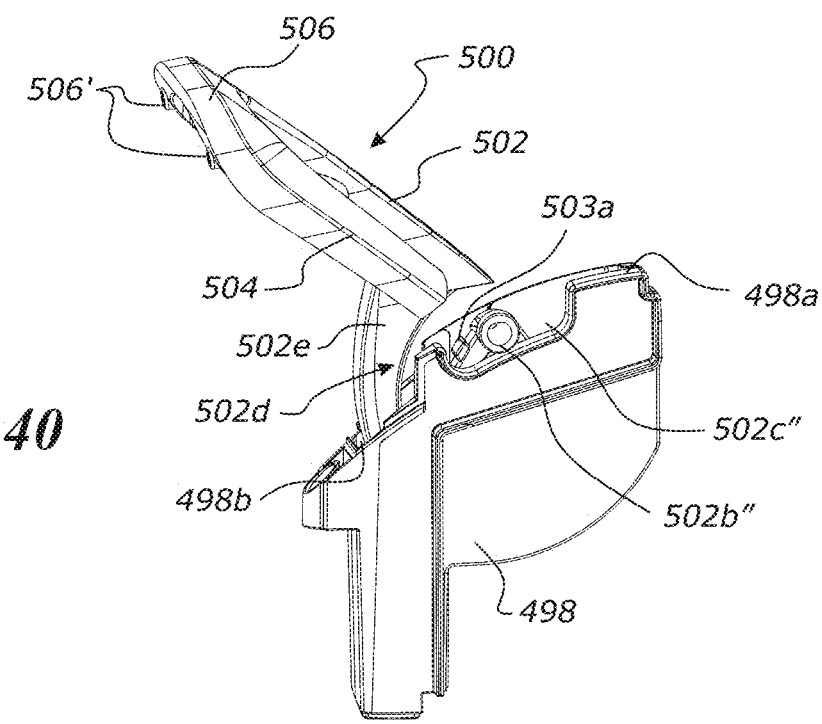
FIG. 40 is a view corresponding to FIG. 34 but with the handle/lever in the more raised position corresponding to FIG. 28.

The front pivot protrusion 502*b*" is received in a second pivot cavity 502*c*" as shown in FIGS. 38 to 41. The second pivot cavity 502*c*" comprises a slot or a channel, and is a relatively horizontal pivot cavity extending substantially in a forward-rearward direction of the apparatus. The second pivot cavity 502*c*" is either substantially linear or is generally arcuate with a large radius of curvature so that the front pivot protrusion 502*b*" follows a substantially arcuate path AP as the handle is moved between the lowered position and the raised position. In the form shown, the second pivot cavity 502*c*" substantially follows the curvature of the left side interconnecting wall 114, and has a convex curvature relative to a position above the pivot cavity. The front pivot protrusion 502*b*" is configured to be retained in the second pivot cavity 502*c*", but to substantially freely move along the length of that pivot cavity. When the handle 500 is raised from the lowered position, initially the front pivot protrusion 502*b*" does not move rearward from the front of the second pivot cavity 502*c*", despite the rear pivot protrusion 502*b*' moving downward and forward in the first pivot cavity 502*c*' (FIGS. 34, 36, 39, 40). When the rear of the pivot protrusion 502*b*' is in the direction change DC region of FIG. 36, the front pivot protrusion 502*b*" has moved rearwardly to less than halfway along the length of the second pivot cavity 502*c*" (FIG. 40). As the handle 500 is then moved to the fully raised position, the rear pivot protrusion 502*b*' moves to the position near the top of the front portion of the first pivot cavity 502*c*' shown in FIG. 37 and the forward pivot protrusion 502*b*" moves to the position at the rear of the second pivot cavity 502*c*" shown in FIG. 41.

The rear and front pivot protrusions 502*b*', 502*b*" may comprise members that are received in corresponding apertures in the body portion 502*f* of the handle. Alternatively, the pivot protrusions may be integrally formed with the body portion 502*f*.

The apparatus comprises a handle retainer 498, which is shown most clearly in FIGS. 30 to 41. The handle retainer comprises a substantially hollow body that has an upper edge 498*a* corresponding substantially in shape to the underside of the interconnecting wall 114. However, the handle retainer 498 projects further forward than a front edge of the interconnecting wall 114, so that an aperture 498*b* in the handle retainer 498 is positioned in front of the interconnecting wall 114. The shape of the aperture 498*b* corresponds substantially to that of the forward arcuate portion 502*e* of the pivot arm. The aperture 498*b* is sized so as to be only slightly larger than that of the forward arcuate portion 502*e* of the pivot arm, so that there is no space for foreign objects to be entered into the aperture when the handle is raised.

The handle retainer 498 comprises a base wall that opens into a liquid drain channel 498*c* that extends down the side of the housing. The liquid drain channel 498*c* may be in communication with a cavity in the base of the main housing, so that any liquid that enters the handle mechanism can drain through the liquid drain channel 498*c* and exit through apertures in the base of the main housing 100. The handle retainer provides a diffusion-based mechanism to remove liquid/gas. Additionally, the holes in the chassis parts for receipt of the handle retainer/handle are small and self-contained and are spaced apart from sources of gas to reduce the likelihood of gas leakage into the case of the apparatus. Apertures do not need to be punched into the walls of the chassis parts for receipt of the handle pivots.

The handle retainer 498 seals between the upper chassis 102 and the lower chassis 202 in the region of the handle retainer. In an alternative configuration, the handle retainer 498 could seal against the upper chassis 102 and/or the handle 500 to prevent liquids/gases from entering the case or the handle retainer. Face seals, convoluted path seals, and/or tongue and groove arrangements could be provided for example.

Figure 43:
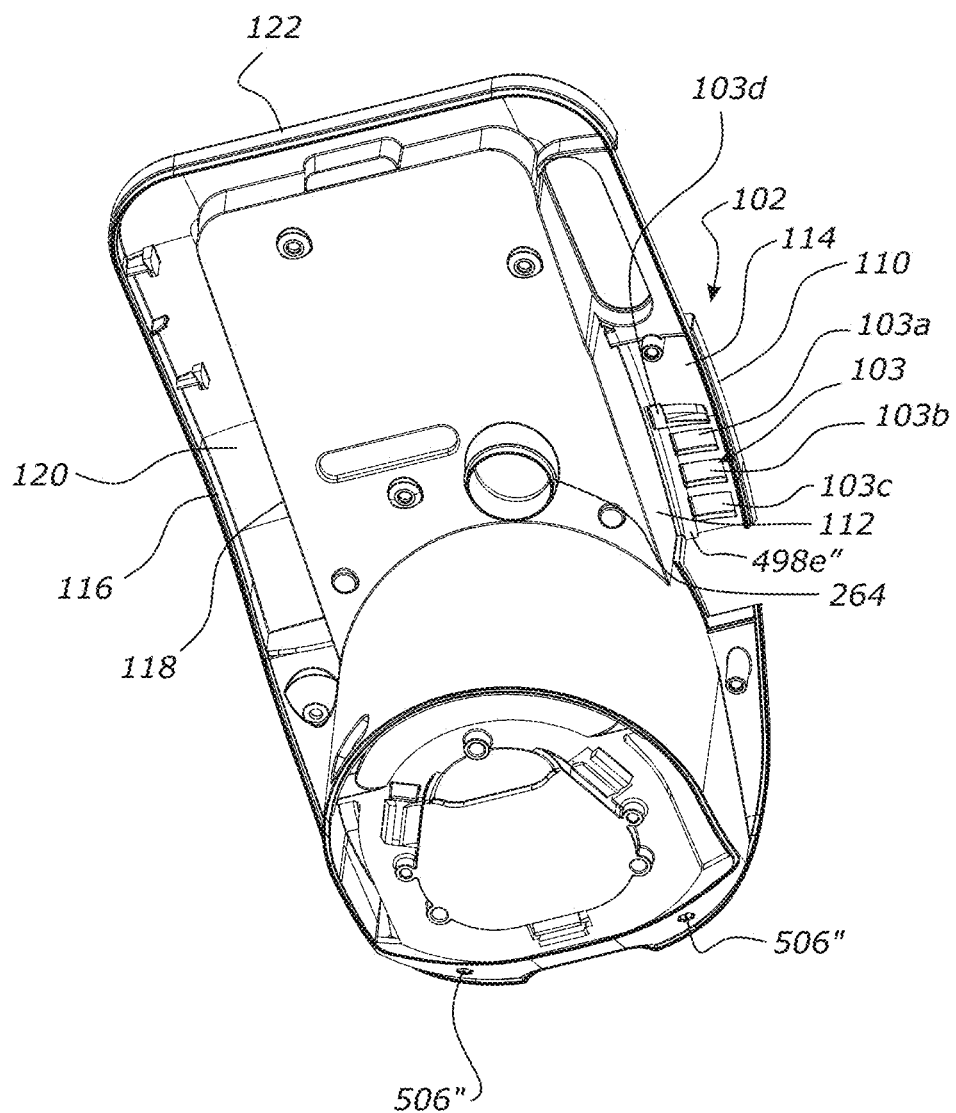
FIG. 43 is a rear left underside perspective view of the upper chassis of the apparatus.

As shown in FIG. 38, an inner portion of the right side wall of the handle retainer comprises a ledge 498*e*' that forms a base of the second pivot cavity 502*c*". As shown in FIG. 43, an underside 498*e*" of an inner wall portion of the upper chassis 102 forms an upper edge of the second pivot cavity 502*c*".

To mount the handle 500 to the apparatus, the handle 500 is positioned in the handle retainer 498 so that the second pivot protrusion 502*b*" is positioned on the ledge 498*e*' and so that the first pivot protrusion 502*b*' is positioned in the first pivot cavity 502*c*'. The handle and handle retainer can then be moved into engagement with the upper chassis part 102 such that apertures in the handle retainer are aligned with apertures in the upper chassis 102, and fasteners such as screws or the like are used to fasten the components together. Therefore, the handle retainer 498 becomes part of the main housing 100 of the apparatus when the handle retainer is fixed to the upper chassis.

Figure 44:
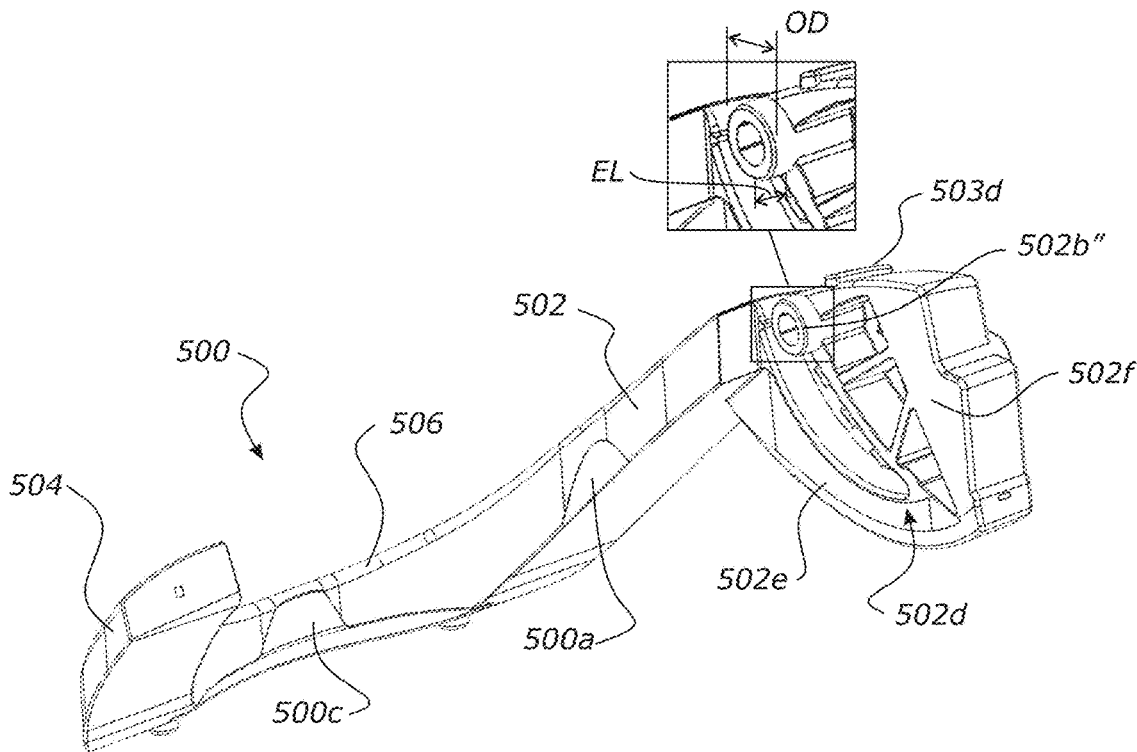
FIG. 44 is a rear right side perspective view of the handle/lever.

Movement of the pivot protrusions 502b', 502b" and the handle 500 can be split into several phases as shown in FIGS. 30 to 41 and discussed above. Those phases are represented graphically in FIG. 44. Referring to FIG. 44, the path of movement of the terminal end 506 of the handle relative to the apparatus housing is shown by curve TEP. That path has a varying radius of movement of the terminal end of the handle from a fully lowered to a fully raised position. In the form shown, the path is generally elliptical; that is, it follows the shape of a part of an ellipse. In the form shown, the path corresponds to slightly over one quarter of an ellipse. The radial lines represent a general transition point from one phase to another or indicate the beginning and ending of a phase relative to the position of the end of the handle.

Figure 31:
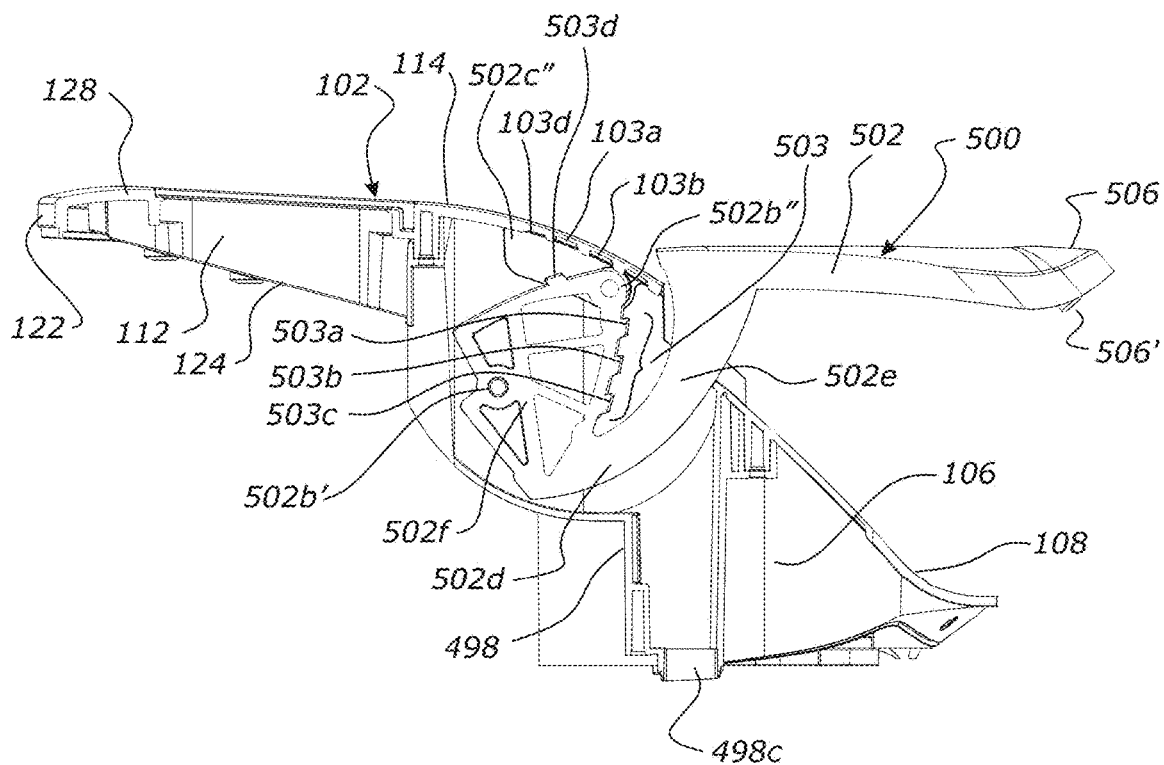
FIG. 31 is a view corresponding to FIG. 30 but with the handle/lever in the partly raised position corresponding to FIG. 27.

FIGS. 31, 35, and 39 show the handle as it has been moved away from a fully lowered position. During this first phase P1 of movement, the second pivot protrusion 502b" remains at the terminal forward end of the second pivot cavity 502c". The first pivot protrusion 502b' is caused to translate downward and forward along linear path LP1. This urges the end 506 of the handle forward and upward away from the lowered/closed position. The initial movement of the terminal end of the handle 500 is out and away from the housing so that the handle does not collide with the housing at either end.

Figure 32:
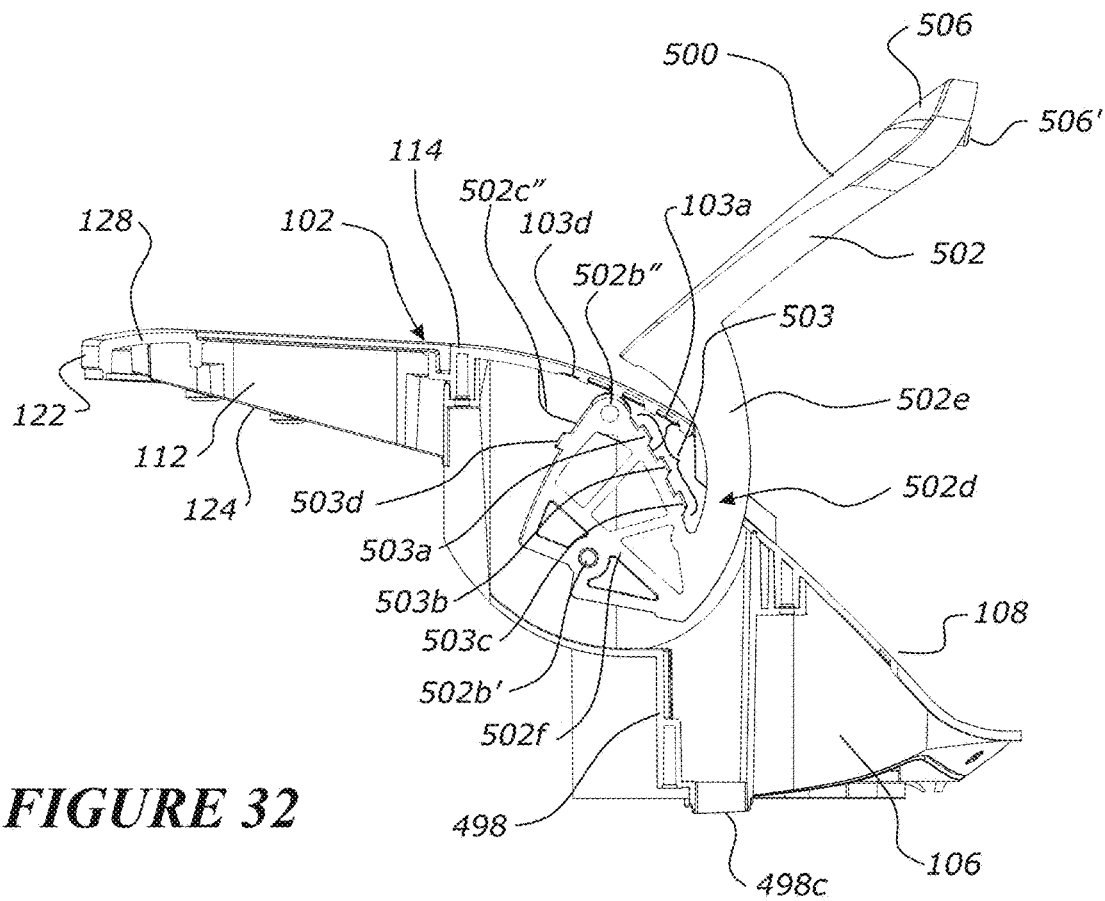
FIG. 32 is a view corresponding to FIG. 30 but with the handle/lever in the more raised position corresponding to FIG. 28.

FIGS. 32, 36, and 40 show the handle as it has been moved further away from the closed position. During this second phase P2 of movement, the first pivot protrusion 502b' has translated further downward in the first pivot cavity 502c' relative to the housing and is undergoing the direction change DC. The second pivot protrusion 502b" has started to translate rearwardly along the second pivot cavity 502c". This results in a relatively steep upward and rearward movement of the terminal end 506 of the handle relative to the housing.

Figure 33:
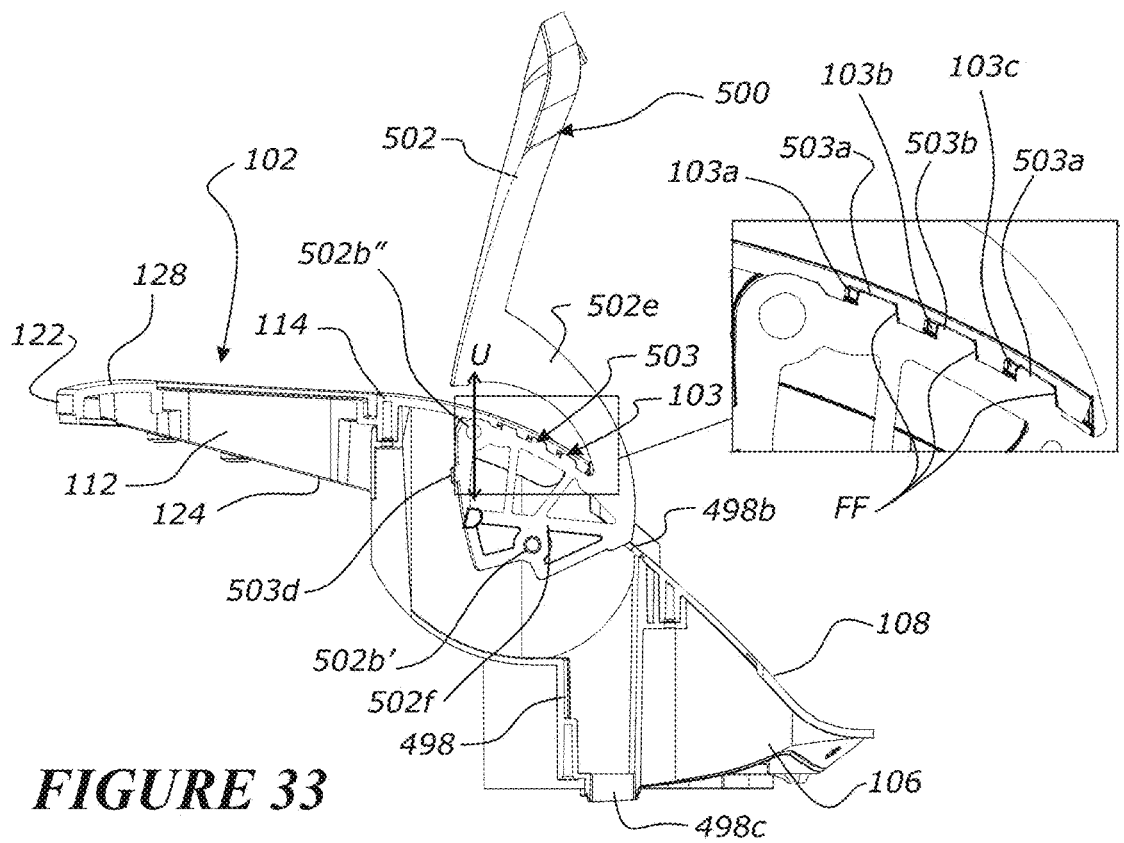
FIG. 33 is a view corresponding to FIG. 30 but with the handle/lever in the fully raised position corresponding to FIG. 29.
Figure 34:
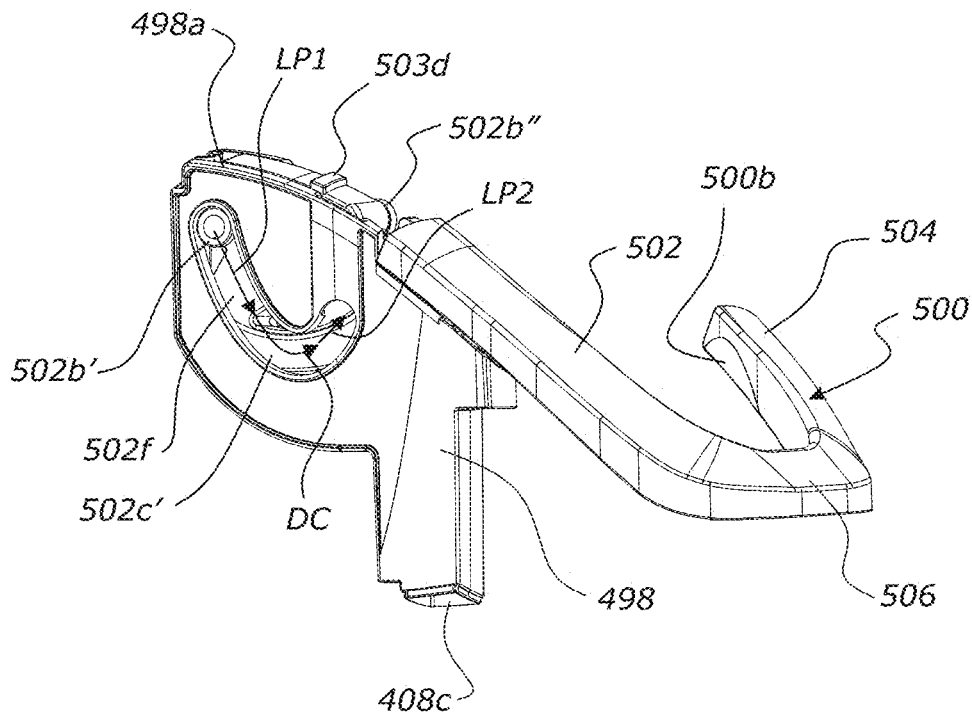
FIG. 34 is a front left perspective view of the handle retainer and the handle/lever in the lowered position corresponding to FIG. 2.
Figure 41:
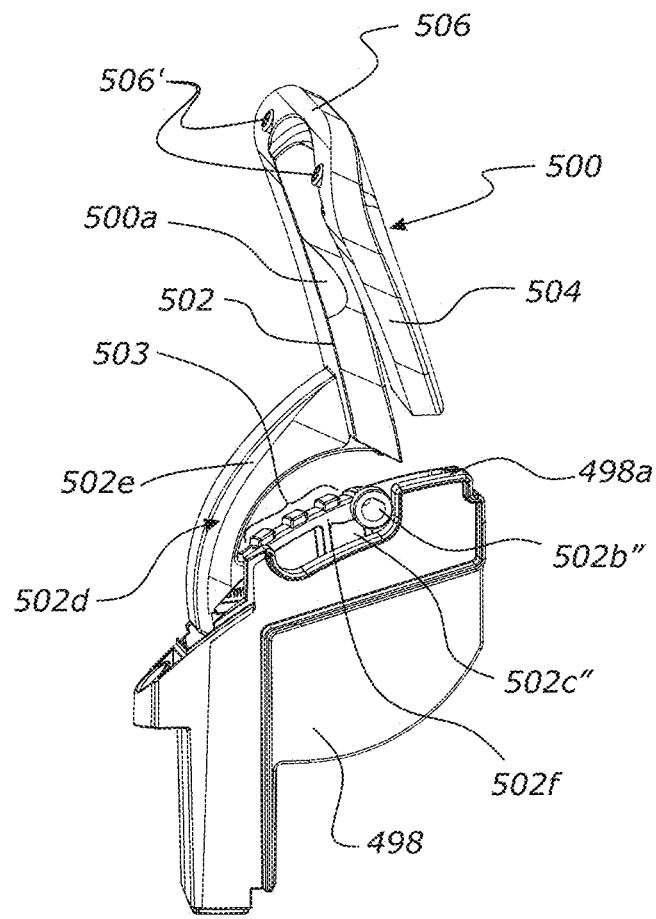
FIG. 41 is a view corresponding to FIG. 34 but with the handle/lever in the fully raised position corresponding to FIG. 29.
Figure 42:
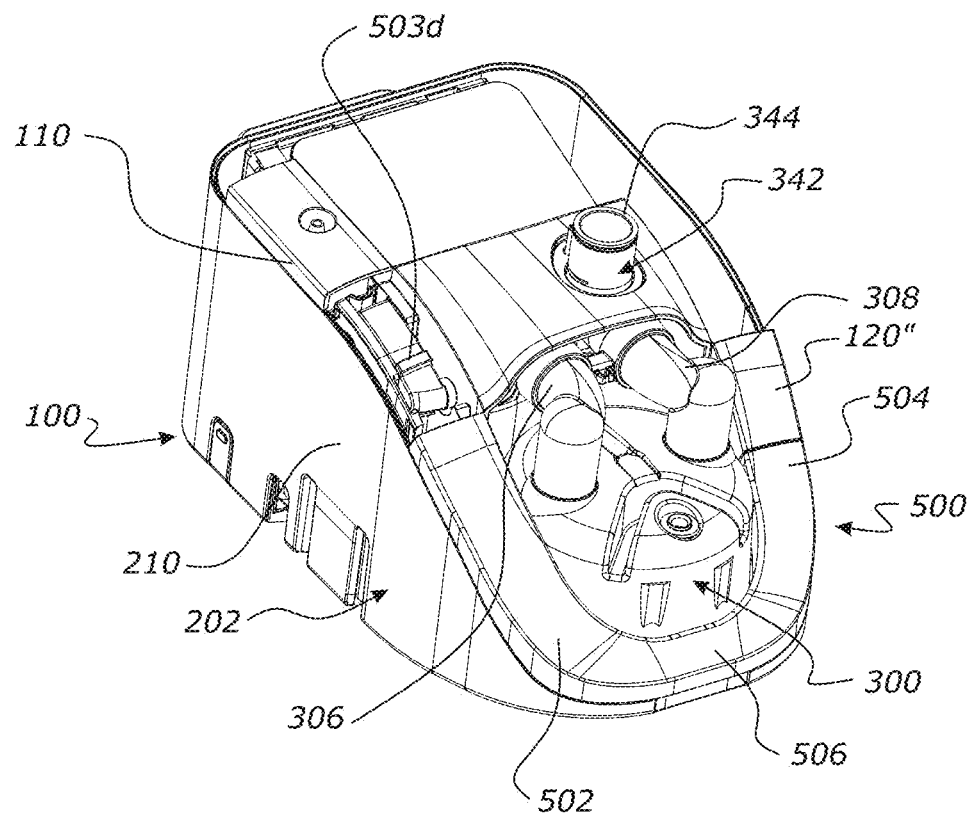
FIG. 42 is a front left overhead perspective view of the apparatus with the upper chassis part removed.

As shown in FIGS. 33, 37, and 41, at the end of the third phase P3 of movement, the second pivot protrusion 502b" has reached the rear end of the second pivot cavity 502c" and the first pivot protrusion 502b' has reached the upper forward end of the first pivot cavity 502c'.

The first pivot protrusion 502b' is fully constrained in the first pivot cavity 502c' throughout movement of the handle 500.

The handle 500 and housing 100 could have a different configuration of pivots and pivot cavities, while still providing the moment phases shown in FIG. 44.

The handle 500 is designed so that when the handle is in the fully raised position and is being used to carry the apparatus 10, the handle is located generally above the centre of gravity of the apparatus including a liquid chamber containing liquid. This reduces tilting or swinging of the apparatus as the apparatus is being carried, making the apparatus easier to carry and reducing the likelihood that liquid will enter the apparatus from the liquid chamber, and acting to keep the apparatus generally level whilst it is being carried. The apparatus may be configured so that the raised handle is over or generally over the centre of mass with a full liquid chamber inserted. The apparatus is heaviest with a full liquid chamber, and that is when liquid is most likely to spill back into the apparatus. Alternatively, the apparatus may be configured so that the raised handle is over or generally over the centre of the mass of the apparatus with a partially full liquid chamber inserted, such as a half-full liquid chamber for example.

Depending on whether the fully raised handle is positioned directly over the centre of mass of the apparatus, or close to that position, the base of the apparatus may sit substantially flat while the apparatus is being carried, or alternatively may be slightly angled while the apparatus is being carried. The force provided by the user in holding the apparatus is not offset significantly from the centre of mass. This also means that the liquid in the liquid chamber 300 remains substantially horizontal, reducing the risk of liquid flow into the gasflow path. The generally elliptical movement path of the handle 500 enables the handle to move from the fully lowered position to a fully raised position located generally above and generally in-line with the centre of mass. Additionally, the movement path is such that there is a substantially constant spacing between the handle and an upper portion of the housing, at least between a partly-raised position (FIG. 31) and fully raised position (FIG. 33) of the handle, to minimise possible pinch points between the handle and the housing.

The handle is designed so that the pivot protrusions 502b', 502b" do not carry the apparatus load when the handle is in the fully lowered position or in the fully raised position.

The housing 100 of the apparatus 10 and the handle 500 comprise complementary interlock features. In the form shown, the body portion 502f of the handle 500 comprises an interlock feature 503 and the underside of the upper chassis portion 102 comprises an interlock feature 103. The complementary interlock features 103, 503 are arranged such that when handle 500 is in the raised position and upward force is applied to the handle 500 relative to the housing 100, the interlock features 103, 503 engage with each other. When the handle 500 is in the raised position but upward force is not applied to the handle 500 relative to the housing 100, the interlock features 103, 503 are disengaged from each other.

In one configuration, the interlock features 103, 503 comprise a projection on one of the handle 500 and the housing 100, and a complementary recess on the other of the handle 500 and the housing 100. In the form shown, the interlock features comprise a plurality of projections 503a, 503b, 503c on the handle 500 that extend generally radially relative to the rear pivot protrusion 502b', and a plurality of complementary recesses 103a, 103b, 103c on the underside of the interconnecting wall 114 of the upper chassis portion 102 (FIG. 43). While three projections and recesses are shown, it will be understood that one, two, three, four, or more projections and recesses can be provided. It will also be understood that either or both components could have the projections and/or recesses.

When the handle 500 is in the fully raised position (FIGS. 33, 37, 41) and no upward force is being applied to the handle 500, the second pivot protrusion 502b" will rest on the lower wall 498e' of the second pivot cavity 502c", the first pivot protrusion 502b' will be positioned slightly below the upper end of the front of the first pivot cavity 502c', and the interlocking features 103, 503 will not be engaged with each other. When a user applies upward force to the handle 500 relative to the housing, such as by lifting the apparatus by the handle 500, the handle 500 will move upwardly relatively to the housing. A recess 103d is positioned at the rear end of the surface 498e" in the underside of the upper chassis 102 as shown in FIG. 43. That recess 103d provides sufficient clearance that the second pivot protrusion 502b" can lift upwardly U (FIG. 33) into the recess 103d away from the lower wall 498e' of the second pivot cavity 502c". At the same time, the first pivot protrusion 502b' can lift upwardly U (FIG. 37) to the top of the upper end of the front of the first pivot cavity 502c'. With that upward movement, the interlock features 103, 503 will engage with one another, so that the upper ends of the protrusions 503a, 503b, 503c contact and engage against the upper surfaces of the recesses 103a, 103b, 103c, and those ends and surfaces transfer the loading of the apparatus to the handle 500, instead of the pivot protrusions 502b', 502b" taking the load. In some configurations, the pivot protrusions 502b', 502b" will not take any of the load when the interlock features 103, 503 are engaged. In alternative configurations, the pivot protrusions 502b', 502b" will take some of the load when the interlock features 103, 503 are engaged. The engagement of the interlock features 103, 503 will inhibit rotation the handle 500 relative to the housing 100, increasing the stability of the apparatus while it is being carried, and the likelihood of the apparatus tipping while being carried. The interlock features 103, 503 also reduce the torque a user must apply to keep the apparatus 10 substantially level whilst it is carried by the handle 500.

When the apparatus 10 is rested back on a surface, the handle 500 and pivot protrusions 502b', 502b" will lower in the housing 100 under the weight of the handle 500, so that the interlock features 103, 503 disengage from each other. The second pivot protrusion 502b" moves down D (FIG. 33) out of the recess 103d, and the first pivot protrusion 502b' moves down D (FIG. 37) in the front of the first pivot cavity 503c'. After that movement, the handle can then be rotated to lower the handle to the lowered position of FIGS. 30, 34, and 38.

It can be seen in the inset to FIG. 33 that the projections 103a, 103b, 103c and the recesses 503a, 503b, 503c are provided with guide features to assist with engagement and/or disengagement of the projections 103a, 103b, 103c with the recesses 503a, 503b, 503c. In the form shown, the recesses are slightly larger than the projections. Additionally, forward faces FF of the recesses and the projections are sloped or angled so as to be non-perpendicular to the top surfaces of the projections and recesses, to assist with engagement and disengagement of the interlock features.

The projections 503a, 503b, 503c may have substantially the same width (in a transverse direction of the apparatus) as the recesses 103a, 103b, 103c to provide improved stability when the projections and recesses are engaged.

As shown in FIGS. 30 to 34, the body portion 502f of the handle 500 comprises an additional interlock feature that is arranged to engage with the interlock feature of the housing when the handle is in the lowered position. In the form shown, the additional interlock feature comprises a projection 503d that has substantially the same form as the projections 503a-d, and that engages in one of the recesses 103a when the handle is lowered (503d). That provides a positive engagement of the handle 500 and the housing 100 when the handle is lowered, reducing the likelihood of a user inadvertently lifting the handle 500 from the lowered position when the apparatus is in use. That also helps reduce the loading applied to the pivot protrusions 503b', 503b" if lateral force is applied to the handle 500 when the handle 500 is in the lowered position. The projection 503d may have substantially the same width (in a transverse direction of the apparatus) as the recess 103a, to provide improved stability when the projection 503d and recess 103a are engaged.

The handle arrangement is configured to carry the full apparatus load including a liquid chamber 300 containing liquid. The handle may comprise honeycomb or rib feature(s) or fibre reinforcement to strengthen and stiffen the handle. The handle may be made from a suitable stiff and strong material. For example, the material may be a plastic material such as polycarbonate. The handle may have a hollow core and for example be produced by gas assist injection moulding. Where the handle has a substantially hollow core the handle may be devoid, or at least have a lesser amount, of honeycomb or rib feature(s).

In the form shown, the handle 500 is pivotally and translationally connected to the housing 100. In an alternative configuration, the interlock features 103, 503 may be incorporated into a handle 500 that is only pivotally or only translationally connected to the housing 100.

In the form shown, only one side of the handle 500 is movably connected to the housing. In an alternative configuration, two sides of the handle 500 may be movably connected to the housing 100. The interlock features 103, 503 may be provided on one or both sides of the handle 500 and housing 100. Two handle retainers 498 may be provided in the housing 100 to receive the two sides of the handle 500. Alternatively, the two sides of the handle 500 may be directly movably connected to two sides of the housing 100.

The interlock features 103, 503 may be provided on different surfaces from those shown. For example, instead of being provided on the body portion 502f, the interlock features 503 could be provided on an upper surface of the arcuate portion 502e of the handle 500, or could be provided elsewhere on the handle 500. As another example, instead of being provided on the underside of the interconnecting wall 114 of the upper chassis 102, the interlock features 503 could be provided elsewhere in the housing 100.

The interlock features 103, 503 could have any suitable shape and configuration. For example, rather than having the shape shown, the projections 503 and recesses 103 could have an arcuate shape, or any suitable polygonal shape. The interlock features need not all have the same shape.

In the form shown, the first pivot protrusion 502b' and first pivot cavity 502c' are located toward an outer portion of the apparatus, and the second pivot protrusion 502b" and the second pivot cavity 502c" are located toward a centre of the apparatus. In an alternative configuration, the sides could be reversed. By having the pivot protrusions and pivot cavities on opposite sides of the handle, the handle mechanism is less likely to bind during movement of the handle 500, particularly at the intersection between the first pivot cavity 502c' and the second pivot cavity 502c". Alternatively, the pivot protrusions 502b', 502b" and the pivot cavities 502c', 502c" could be provided on one side of the device (either towards the centre or the outer side), with a more rounded edge provided at the intersection between the first and second pivot cavities to reduce the likelihood of binding.

Figure 29:
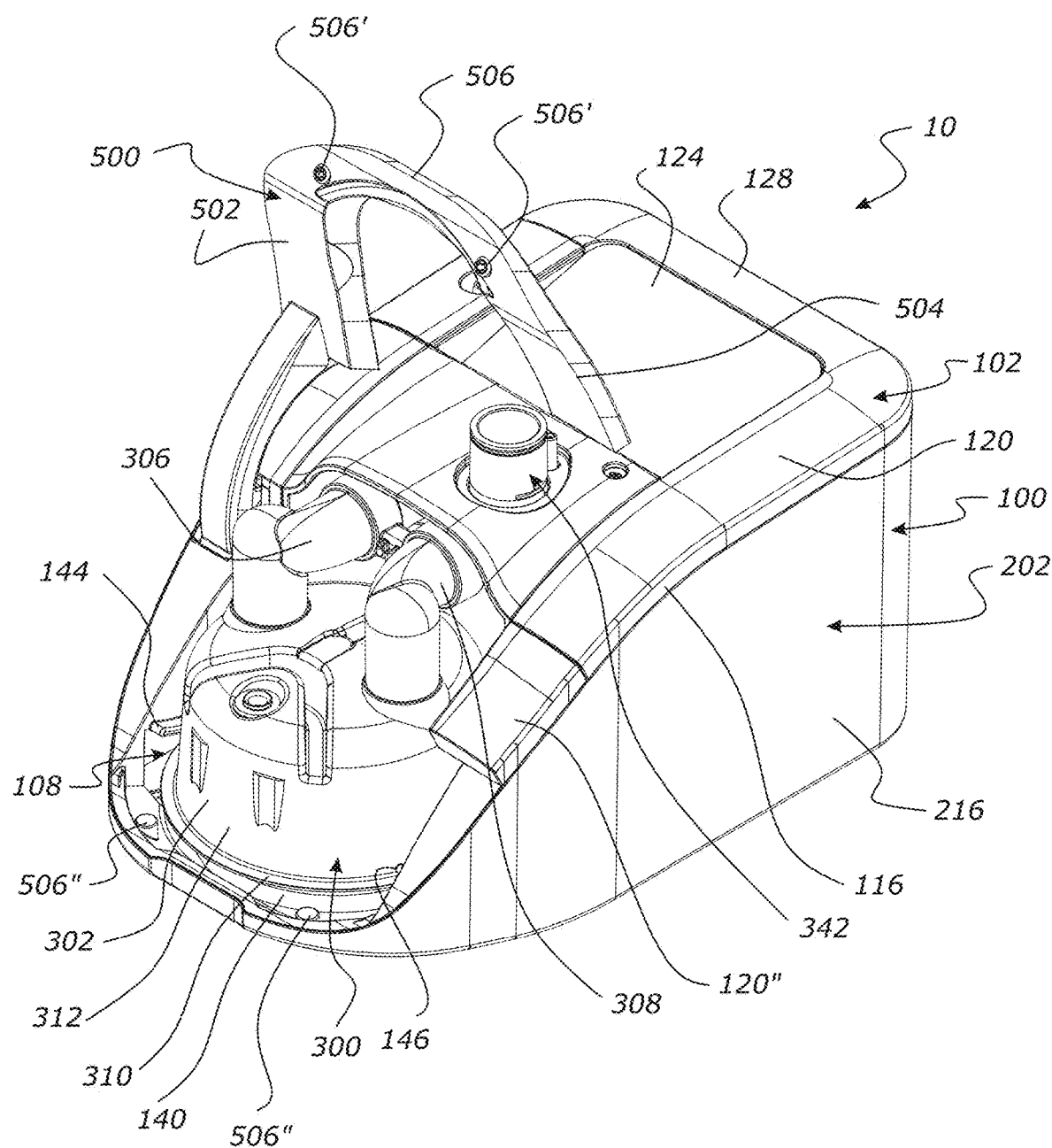
FIG. 29 is a view corresponding to FIG. 28 but with the handle/lever in a fully raised position.
Figure 30:
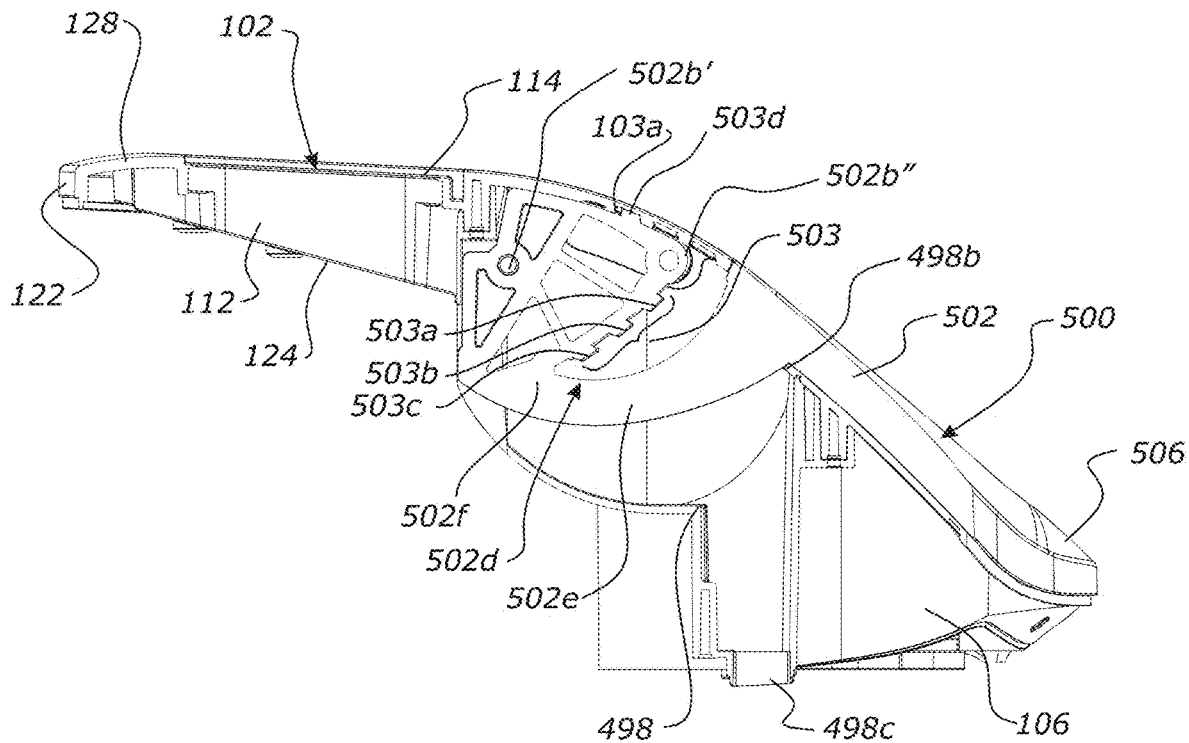
FIG. 30 is a left side partial section view showing part of the apparatus housing, the handle retainer, and the handle/lever in the lowered position corresponding to FIG. 2.

In the form shown, the interlock features 103, 503 are disengaged from each other when the handle 500 is in any one of a plurality of intermediate positions between the first, fully lowered position (FIG. 2) and the second, fully raised position (FIG. 29). That configuration means that there is a single raised position of the handle that is the optimum orientation of the handle 500 relative to the housing 100, in which the interlock features will engage when the handle is used to carry the apparatus 10. In alternative configurations, the interlock features 103, 503 may be engageable with each other when the handle 500 is in one or more of those intermediate positions, by applying upward force to the handle. The first and second pivot cavities 502c', 502c" may be modified to provide one or more additional regions into which the pivot protrusions 502b', 502b" can move to enable the handle 500 to be raised in those additional positions. When the interlock features 103, 503 comprise a plurality of members, a reduced number of the interlock feature members may be engageable when the handle 500 is in an intermediate position compared to when the handle 500 is in the second, fully raised position.

In the form shown, the first position in which the interlock features 103, 503 are engageable corresponds to a fully lowered position of the handle 500 (FIG. 2), and the second position in which the interlock features 103, 503 are engageable corresponds to a fully raised position of the handle 500 (FIG. 38). In alternative configurations, the first and/or second position are different position(s) that aren't the fully raised or fully lowered position. For example, one or both of the first and second positions could be an intermediate position between the lowered position and the raised position. As an example, the handle 500 may be moveable between the fully lowered and fully raised positions shown, but the second position in which the handle can be moved upward relative to the housing to engage the interlock features, may be in intermediate position that is close to, but short of, the fully raised position (for example, the position of the handle shown in FIG. 28). That may be beneficial if the optimum carrying angle of the apparatus 10 is one in which the apparatus is tilted rearwardly, to minimise the likelihood of the liquid chamber 300 inadvertently being released from the liquid chamber bay 108 during carrying of the apparatus. As another example, the second position may be the raised position of the handle 500 shown in FIG. 29, but the handle may be configured such that when the apparatus is resting on a support surface, the handle can be moved further rearwardly than the position shown in FIG. 29, to provide greater clearance to access the liquid chamber 300. Therefore, the first and/or second position may not be at the terminal ends of the path of travel of the handle 500 relative to the housing 100.

A surface of the handle 500 bears against a surface of the handle retainer 4498 throughout movement of the handle from the fully lowered position to the fully raised position, to support the handle and prevent it from wobbling. For example, a left side face of the body portion 502*f* of the handle may bear against the left side wall of the handle retainer throughout that movement. Alternatively, a right side face of portions 502*e*, 502*f* of the handle may bear against the right side wall of the handle retainer throughout that movement. The surfaces that bear against each other are load-bearing and remain load-bearing throughout the movement of the handle.

The arcuate portion 502*e* and body portion 502*f* are wide to deal with bending moments through the single sided handle. The length of the base of the handle (between and extending beyond the pivot protrusions 502*b'*, 502*b"*) may be made as long as possible to reduce wobbling of the handle.

As shown in FIG. 2, when the handle 500 is in the fully lowered position, the handle is flush with the upper portion of the housing. That is, a substantially continuous surface is formed around the upper sides, front, and rear of the upper chassis 102 of the housing, including the handle 500.

When forward/downward force is applied to the handle 500 to lower it from the fully raised position, the force is applied via the handle to the handle retainer 498 rather than directly to the upper or lower chassis. The force is not carried by the pivot protrusions in the pivot cavities.

In some configurations, the main housing and/or handle 500 may be provided with one or more magnets to retain the handle in the fully lowered and/or fully raised positions. For example, the handle may comprises magnet(s) and the housing may comprise magnet(s) or conductive component(s) that are attracted by the magnets, or vice versa. FIG. 29 shows recesses 506' in the underside of the handle 500 on or adjacent the cross-member 506, and corresponding recesses 506" in the upper chassis part 102 of the housing. Each recess may comprise a suitable magnet or conductive component. The apparatus may comprise one or more sensors, such as Hall Effect sensor(s) to determine whether the handle is in a lowered or raised position.

The magnets can provide a tactile and/or audible indication of engagement of the handle in the fully raised and/or lowered position. When using magnets, there is less likelihood of a liquid supply tube to the chamber being compressed and stopping liquid flow, as there may be with a mechanical latch (with which a liquid supply tube could potentially be captured between the handle and main housing, and water flow cut off and/or the tube damaged). Magnets also have the benefit of reduced wear compared to a mechanical engagement feature. Magnets also enable the handle 500 to be released and raised from the lowered position using one hand, and mean that a latch such as a fingerbar or fingerguard is not required (which would require the use of two hands; one to bias a fingerguard downward, to allow for removal of the chamber and one to physically remove the chamber).

The single-sided handle 500 enables tube(s) that connect a liquid bag to the liquid chamber 300 to be fed through the space between the right side member 504 of the handle 500 and the main housing, when the handle 500 is in the raised (or an intermediate) position.

Instead of the pivot cavities 502*c'*, 502*c"* being provided between the upper chassis part of the housing and the handle retainer 498, the pivot cavities could instead be provided in the upper chassis part 102 or between the upper and lower chassis parts 102, 202 of the housing, and the handle retainer 498 not used.

This configuration is also suitable for use with a liquid chamber 300 that is filled from a liquid bag (or other liquid reservoir).

The handle 500 may comprise one or more features, such as apertures or hooks for example, for guiding liquid tube(s) from above into the liquid chamber 300. The tube(s) will be coupled to the liquid chamber. The liquid chamber may comprise a float valve which controls flow of liquid from the tube(s) into the liquid chamber.

The handle 500 will be provided with one or more features to assist with insertion, retention, and/or removal of the liquid chamber 300 in or from the liquid chamber bay 108, such as the engagement features 500*a*, 500*b*, 500*c* for example.

By providing a handle 500 that assists with insertion and/or retention and/or removal of the liquid chamber in and/or from the liquid chamber bay, a user can readily ensure that the liquid chamber 300 is fully inserted in the liquid chamber bay 108 while still being able to easily remove the liquid chamber from the liquid chamber bay when desired. This is particularly advantageous for users with limited mobility. The handle also avoids the use of a separate fingerguard. The liquid chamber bay may have detent(s) to assist with insertion and/or retention of the liquid chamber in the liquid chamber bay, such as those described above in relation to other configurations. Those details will enable a user to readily ensure that the liquid chamber is fully inserted in the liquid chamber bay. Full or correct insertion and/or retention may be required to ensure that a satisfactory seal is obtained and maintained between the liquid chamber and other component(s) that form part of the gasflow path. Because the handle encloses a portion of the liquid chamber bay when the handle is in the closed or fully lowered position, when the handle is in the fully raised position, a large space is created between the cross-member of the handle and the housing of the apparatus including a large opening at the front of the liquid chamber bay and around the liquid chamber, allowing easy insertion and removal of the liquid chamber to and from the liquid chamber bay because a user's fingers can easily fit between housing walls and the liquid chamber.

The handle 500 may be configured so that the liquid chamber 300 can be inserted into the liquid chamber bay 108 when the handle is in the raised position. When the handle 500 is in the lowered position, the handle will act as a chamber guard to both prevent the removal of the liquid chamber 300 from the liquid chamber bay 108, and to prevent a user from touching the heater plate in the base of the liquid chamber. The handle may also minimise the likelihood of items being dropped into the liquid chamber bay 108 when the handle is in the lowered position.

Removal of the liquid chamber 300 from the liquid chamber bay 108 is a two-step procedure. First, the user lifts the handle 500 to the fully raised position. Second, the user removes the liquid chamber 300 from the liquid chamber bay 108. Each of these steps can be done with a single hand, and the force required to perform each of the steps is low. This makes the apparatus particularly suitable for home use by a user who is unwell, and easier to use than an apparatus that requires two-handed operation to release a fingerguard.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. For example, while the motor and/or sensor sub-assembly recess is described as being in the underside of the main housing, it could alternatively be in a rear, side, front, or top of the housing. With such a variant, the air and/or oxygen inlets may also be positioned differently as required.

As another example, rather than the liquid chamber and liquid chamber bay being configured so that the liquid chamber is inserted into and removed from the liquid chamber bay from a front of the housing, the configuration could be such that the liquid chamber is inserted into and removed from the liquid chamber bay from a side, rear, or top of the housing.

The features are described with reference to a flow therapy apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy).

Alternatively, one, some, or all of the features may be provided in an apparatus for a different purpose. The apparatus may be a high flow therapy apparatus, or may be a low flow therapy apparatus. For example, the features may be provided in an apparatus for providing continuous positive airway pressure (CPAP), which may deliver gases (humidified or otherwise) at lower flow rates.

One or some of the features may alternatively be provided in an apparatus that does not require a humidifier and therefore does not require the liquid chamber 300 or liquid chamber bay 108 features.

The 'flow therapy apparatus' language is intended to cover all such variants.

Reference to any prior art in this specification is not, and should not be taken as, an acknowledgement or any form of suggestion that that prior art forms part of the common general knowledge in the field of endeavour in any country in the world.

Where reference is used herein to directional terms such as "up", "down", "forward", "rearward", "horizontal", "vertical" etc, those terms refer to when the apparatus is in a typical in-use position, and are used to show and/or describe relative directions or orientations.

The invention claimed is:

1. An apparatus for delivering a humidified flow of gas, the apparatus comprising a housing, the housing receiving a humidification chamber, a cover that is connectable to the housing, a battery chamber defined by the cover and the housing, an upper surface of the cover comprising at least one of a cover groove and a cover ridge, the housing comprising a mating surface that adjoins the upper surface of the cover, the mating surface comprising at least one of a housing groove and a housing ridge that is configured to mate with the at least one of the cover groove and the cover ridge of the upper surface of the cover, mating the at least one of the cover groove and the cover ridge of the upper surface of the cover and the at least one of the housing groove and the housing ridge of the mating surface of the housing defines a tortuous path when the cover is installed, the tortuous path limiting an ingress of liquid and oxygen into the battery chamber, and one or more fasteners securing the cover to the housing, the one or more fasteners extending upward when the apparatus is positioned for use.

2. The apparatus of claim 1, wherein the upper surface of the cover defines an upper horizontal edge.

3. The apparatus of claim 1, wherein the cover comprises a flange, the flange being located on a side wall of the cover, the flange comprising one or more locating features, wherein the one or more locating features of the cover are adapted to align to one or more complementary locating features on the housing.

4. The apparatus of claim 3, wherein the flange of the cover comprises a valve retention tab, the valve retention tab being sized and positioned to overlap with at least one of a motor module and a sensor module such that the cover would need to be removed before the at least one of the motor module and the sensor module.

5. The apparatus of claim 3, wherein one of the one or more locating features of the cover and the one or more complementary locating features of the housing comprise at least one projection and the one or more locating features of another of the cover and the housing comprises at least one corresponding recess, the at least one projection and the at least one corresponding recess defining an interlock between the housing and the cover.

6. The apparatus of claim 3, wherein the one or more locating features of the cover and the one or more complementary locating features of the housing are configured to receive one or more fastener.

7. The apparatus of claim 1, wherein the cover may include a ledge on an inner surface of the cover.

8. The apparatus of claim 7, wherein the ledge is supported by one or more structural ribs.

9. An apparatus for delivering a humidified flow of gas, the apparatus comprising a housing, the housing receiving a humidification chamber, a cover that is connectable to the housing, a battery chamber defined by the cover and the housing, each of the housing and cover having complementary locating features, the complementary locating features being adapted to locate and align the cover and the housing relative to each other, each of the housing and the cover having complementary structures that define a means for creating a tortuous path to limit ingress of liquid and oxygen into the battery chamber from outside of the housing and the cover.

10. The apparatus of claim 9, wherein one of the complementary locating features of the cover and the housing comprises a projection and another of the complementary locating features of the cover and the housing comprises a recess, the projection and the recess defining an interlock.

11. The apparatus of claim 10, wherein the complementary locating features of the housing and the cover are configured to receive a fastener, the fastener extending upward into the housing and the cover.

12. The apparatus of claim 11, wherein the fastener does not intersect with surfaces comprising the means for creating the tortuous path to limit ingress of liquid and oxygen into the battery chamber from outside of the housing and the cover.

13. The apparatus of claim 9, wherein the complementary locating features are disposed along side walls of the cover or at least one side wall and a back wall of the cover.

14. The apparatus of claim 9, wherein the cover comprises a ledge positioned within the cover, the ledge being sized and configured to support a battery.

15. The apparatus of claim 14, wherein the ledge is supported by one or more structural ribs.

16. The apparatus of claim 9, the housing comprising an exterior back wall, the cover being positioned at the exterior back wall of the housing.

17. The apparatus of claim 9, wherein the cover comprises a valve retention tab, the valve retention tab being sized and positioned to overlap with at least one of a motor module and a sensor module of the housing such that the cover would need to be removed from the housing before the at least one of the motor module and the sensor module.

18. The apparatus of claim 9, wherein the cover comprises one or more liquid deflectors, the one or more liquid deflectors extending inwardly and being sized and configured to protect electrical connections.

* * * * *